United States Patent [19]
Mockros et al.

[11] Patent Number: 5,957,950
[45] Date of Patent: Sep. 28, 1999

[54] VASCULAR ACOUSTIC EMISSION ANALYSIS IN A BALLOON ANGIOPLASTY SYSTEM

[75] Inventors: Lyle F. Mockros, Glenview; John M. Fildes, Batavia, both of Ill.; Krishnan B. Chandran, Iowa City, Iowa; Michael J. Vonesh, Flagstaff, Ariz.; David D. McPherson, Chicago, Ill.; Ashwin Nagaraj, Evanston, Ill.; Charles Davidson, Winnetka, Ill.

[73] Assignee: Northwestern University Medical School, Chicago, Ill.

[21] Appl. No.: 08/874,880

[22] Filed: Jun. 13, 1997

Related U.S. Application Data

[63] Continuation of application No. 08/786,483, Jan. 21, 1997.
[51] Int. Cl.[6] .................................................. A61M 25/10
[52] U.S. Cl. ............................................ 606/194; 600/586
[58] Field of Search ................................... 606/194, 108; 604/96; 600/470, 586

[56] References Cited

U.S. PATENT DOCUMENTS

| | | | |
|---|---|---|---|
| 5,226,430 | 7/1993 | Spears et al. | 606/194 |
| 5,421,338 | 6/1995 | Crowley et al. | 604/98 X |

*Primary Examiner*—Michael H. Thaler
*Attorney, Agent, or Firm*—Michael D. Rechtin; Foley & Lardner

[57] ABSTRACT

A system and method for performing balloon angioplasty treatment on a patient. The system includes a catheter for insertion into an artery of the patient, a balloon coupled to the catheter with the balloon expandable by fluid passed through the catheter in order to apply pressure to plaque lesions deposited on vascular tissue of the artery. The balloon includes a PVDF piezoelectric transducer for sensing acoustic emission signals generated by deformation of the plaque lesions and the vascular tissue. The acoustic emission signals can be analyzed by frequency analysis, time domain analysis and wavelet analysis followed by neural net correlation evaluation.

22 Claims, 63 Drawing Sheets

FIG. 1A
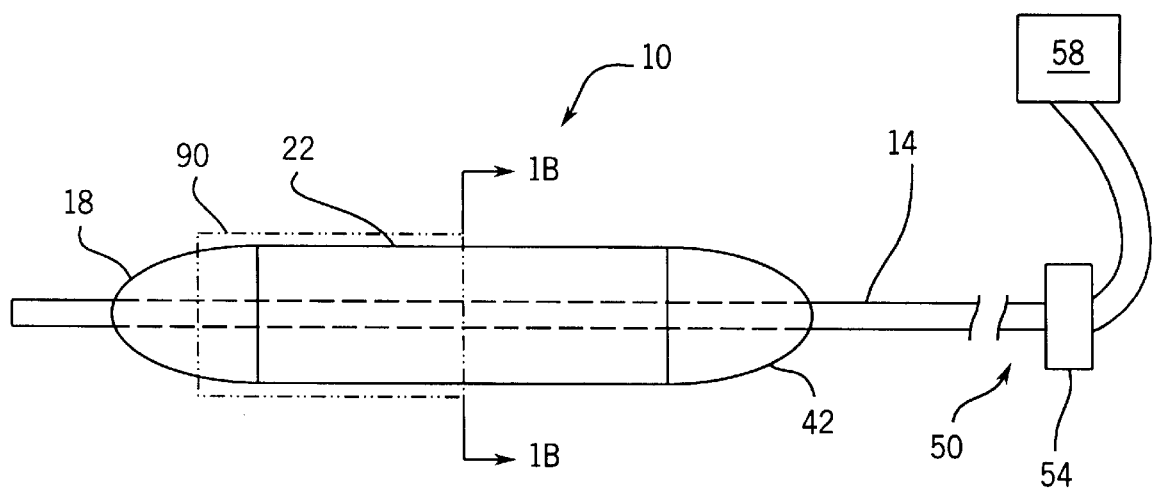
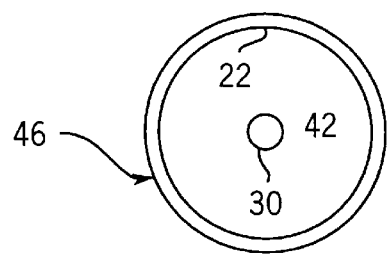
FIG. 1B

FIG. 3A
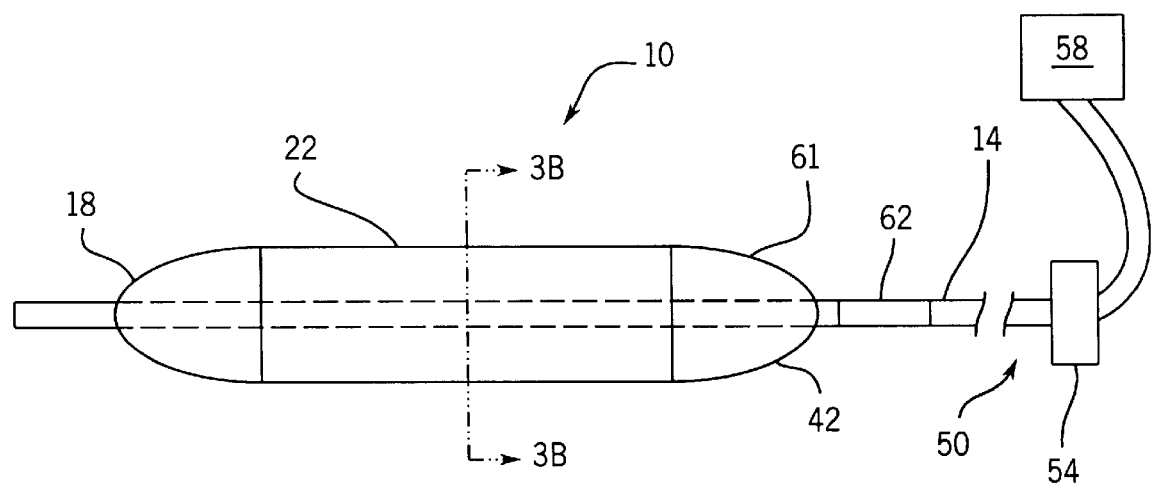
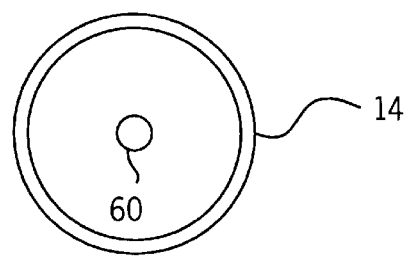
FIG. 3B

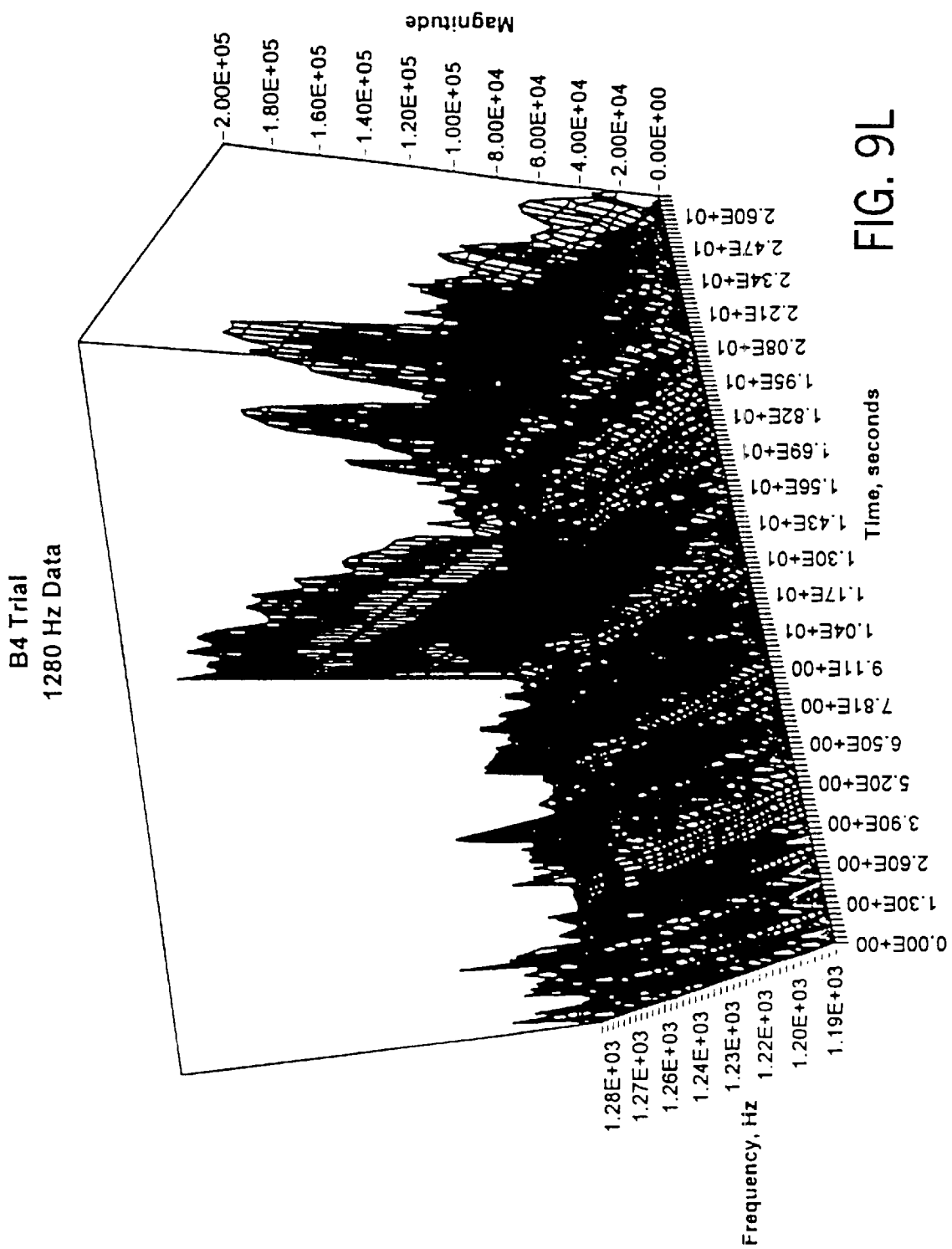

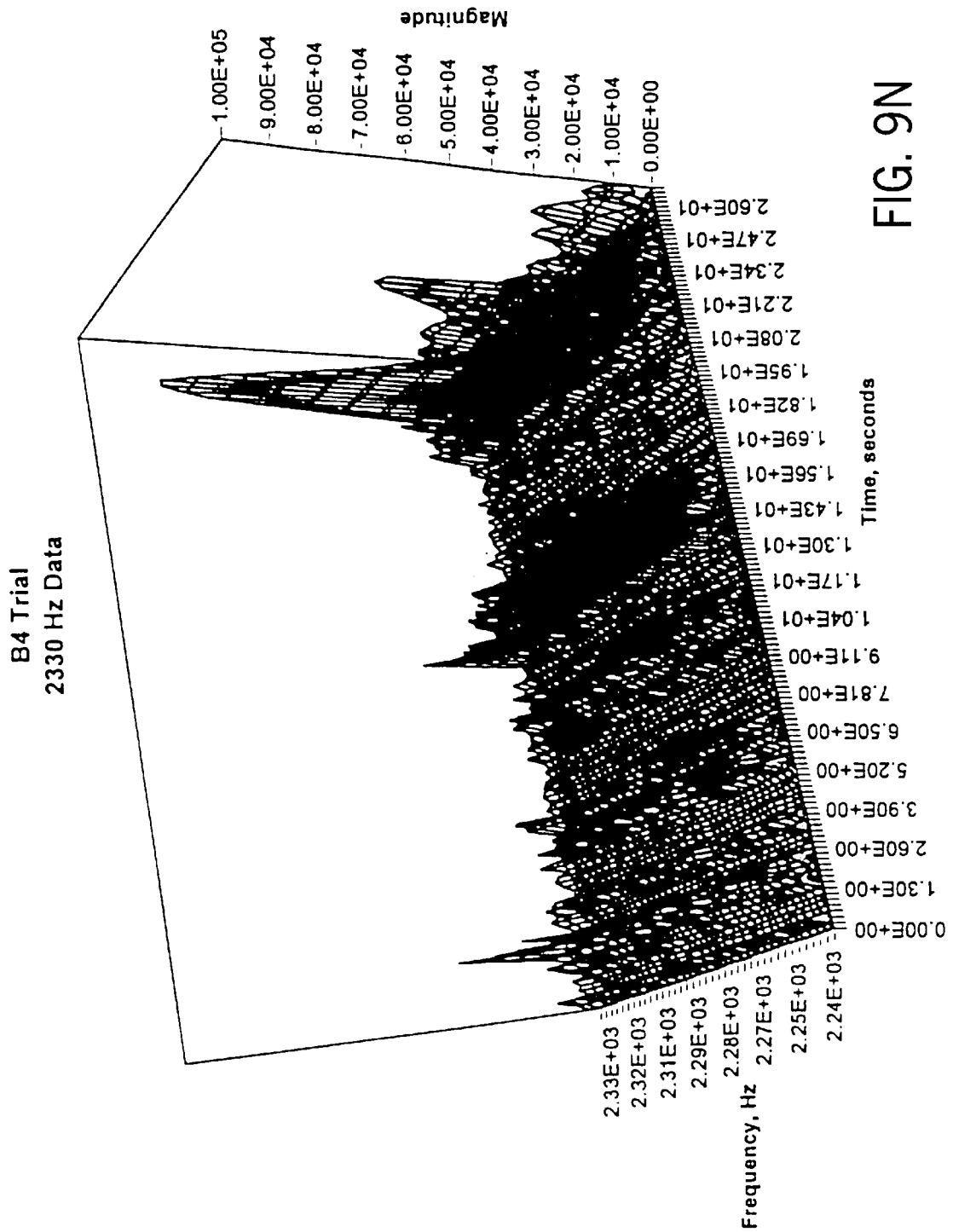

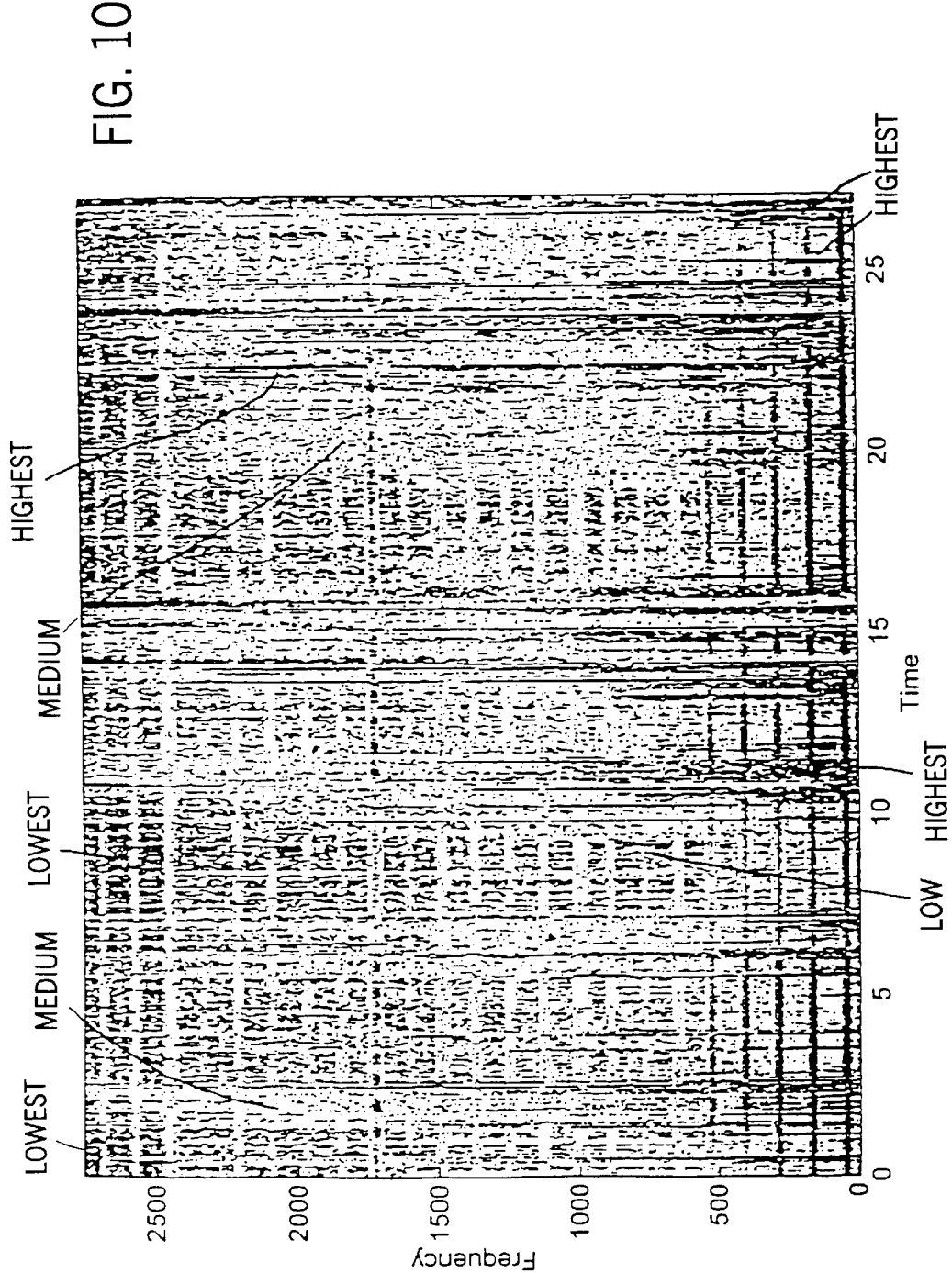

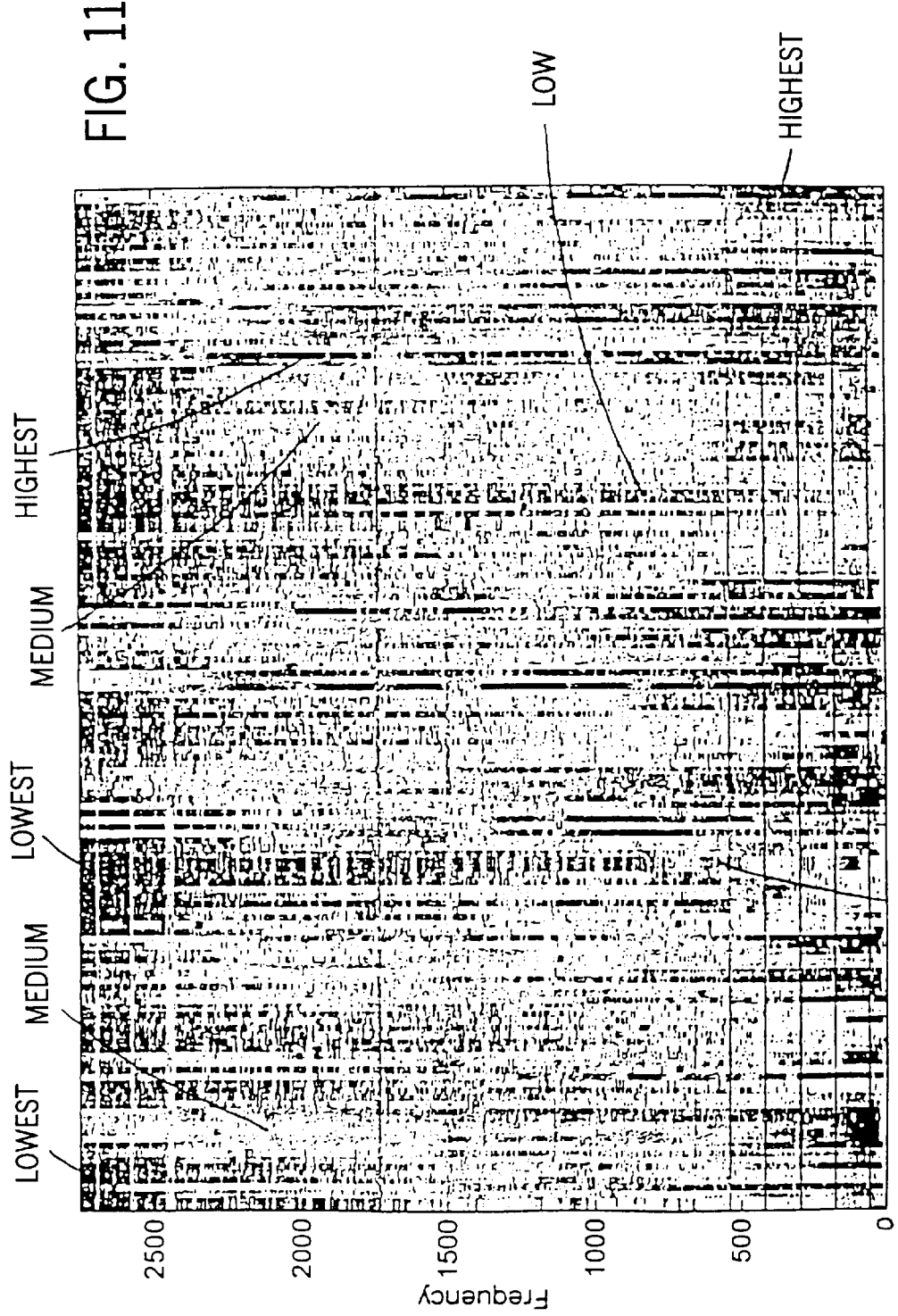

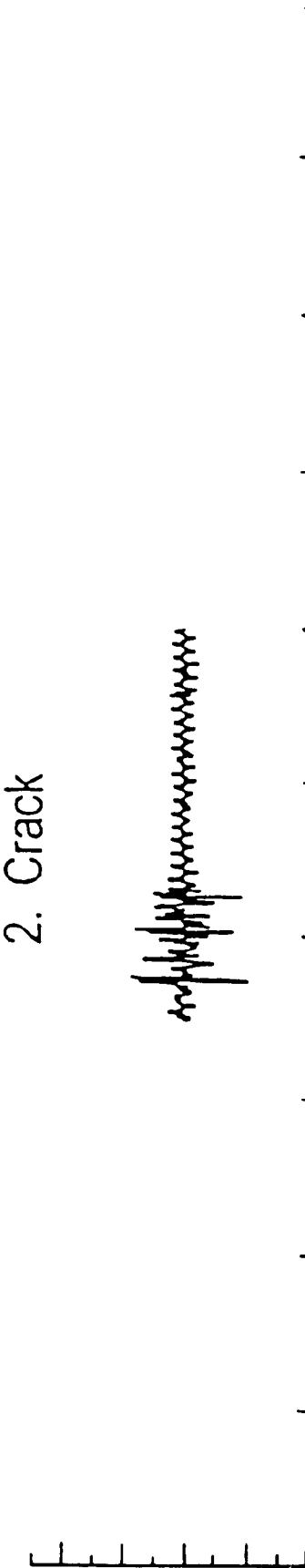

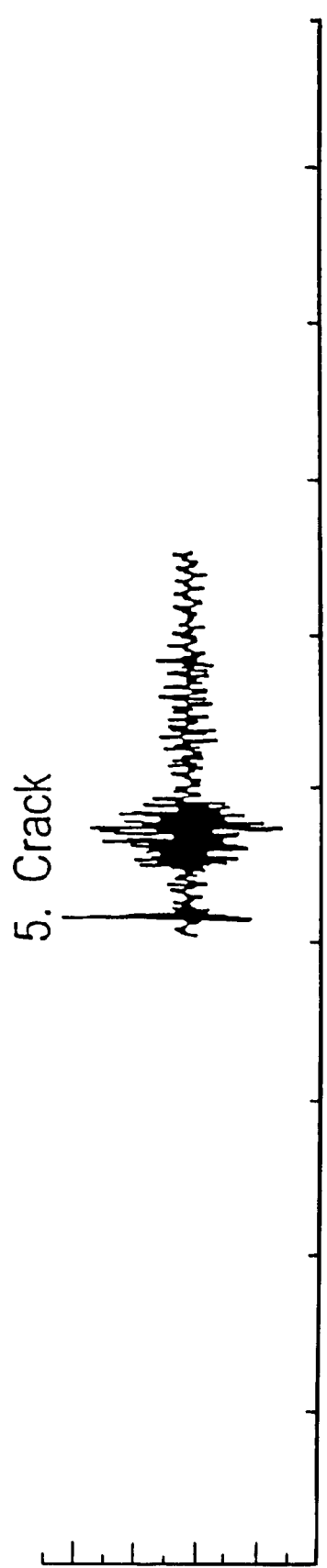

8. No Notable Sounds

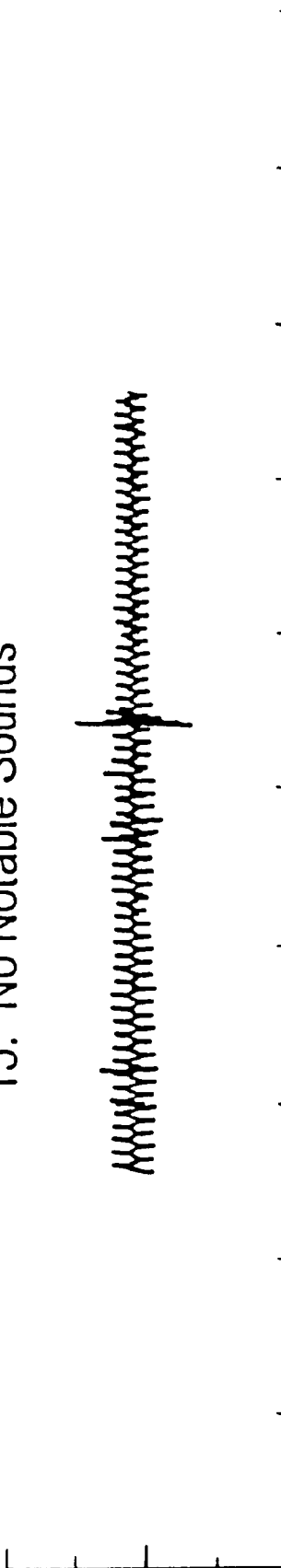

PRELIMINARY STUDIES
FIG. 31A
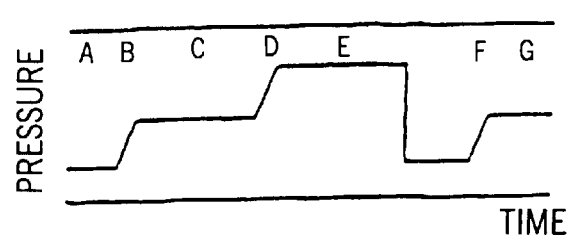
FIG. 31B SPECIMEN 1
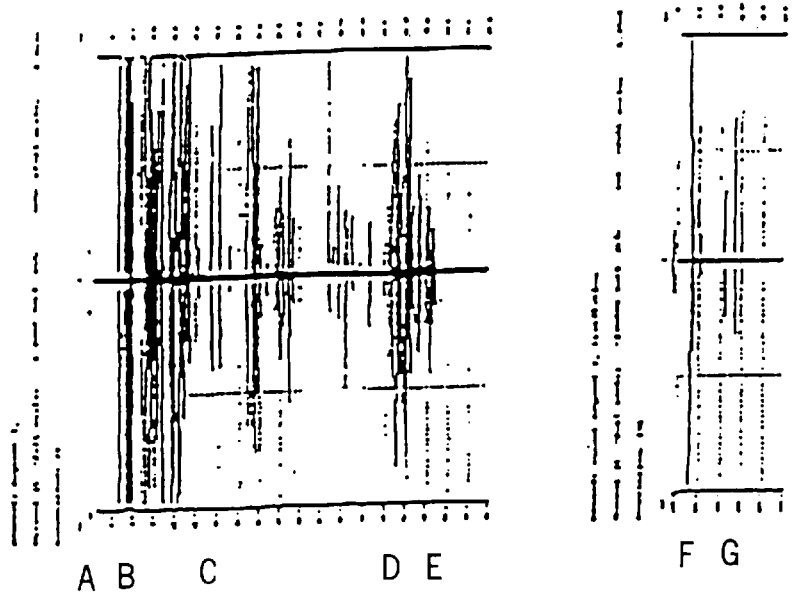
FIG. 31C SPECIMEN 2
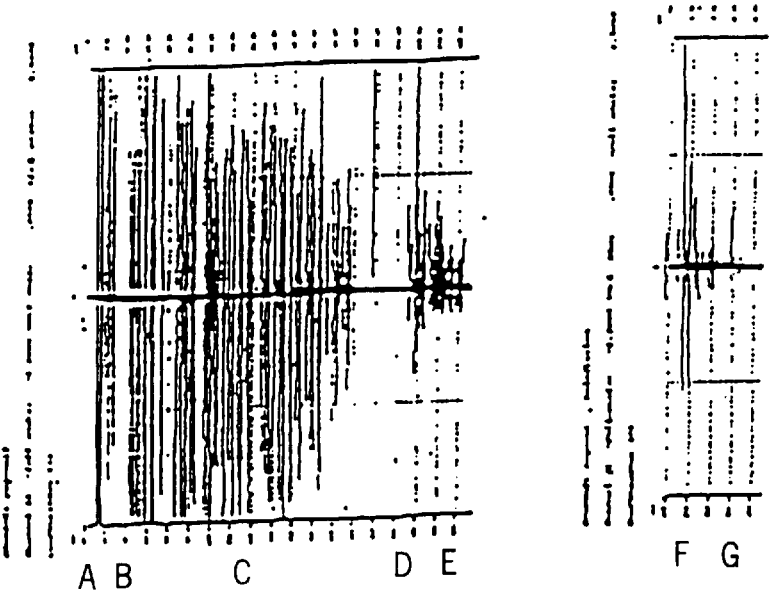

BALLOON ALONE

BALLOON W/TISSUE

SHIELDED

BALLOON ALONE

BALLOON W/TISSUE

|       | GROUP |   |   |   |   |
|-------|---|---|---|---|---|
|       | ① | ② | ③ | ④ | ⑤ |
| 10.2  | 0 | 1 | 0 | 0 | 0 |
| 10.4  | 0 | 0 | 0 | 1 | 0 |
| 10.6  | 0 | 0 | 1 | 0 | 0 |
| 10.8  | 0 | 0 | 0 | 1 | 0 |
| 4 ⎡ 11.0 | 0 | 0 | 0 | 1 | 0 |
|   11.2 | 0 | 0 | 0 | 1 | 0 |
|   ⎣ 11.3 | 0 | 0 | 0 | 1 | 0 |
| 11.5  | 0 | 1 | 0 | 0 | 0 |
| 11.7  | 0 | 1 | 0 | 0 | 0 |
| 11.9  | 0 | 1 | 0 | 0 | 0 |
| 1 ⎡ 12.1 | 1 | 0 | 0 | 0 | 0 |
|   12.3 | 1 | 0 | 0 | 0 | 0 |
|   12.5 | 1 | 0 | 0 | 0 | 0 |
|   12.6 | 1 | 0 | 0 | 0 | 0 |
|   ⎣ 12.8 | 1 | 0 | 0 | 0 | 0 |
| 13.0  | 0 | 0 | 1 | 0 | 0 |
| 13.2  | 0 | 0 | 1 | 0 | 0 |
| 13.4  | 0 | 0 | 1 | 0 | 0 |
| 13.6  | 0 | 0 | 0 | 0 | 0 |
| 13.8  | 0 | 0 | 0 | 1 | 0 |
| 13.9  | 0 | 0 | 0 | 0 | 1 |
| 2 ⎡ 14.1 | 0 | 1 | 0 | 0 | 0 |
|   14.3 | 0 | 1 | 0 | 0 | 0 |
|   ⎣ 14.5 | 0 | 1 | 0 | 0 | 0 |
| 14.7  | 0 | 0 | 0 | 1 | 0 |
| 14.9  | 0 | 0 | 0 | 1 | 0 |
| 15.1  | 0 | 0 | 0 | 1 | 0 |
| 15.2  | 0 | 1 | 0 | 0 | 0 |
| 15.4  | 0 | 1 | 0 | 0 | 1 |
| 15.6  | 0 | 0 | 0 | 0 | 1 |
| 15.8  | 0 | 1 | 0 | 0 | 0 |
| 16.0  | 0 | 1 | 0 | 1 | 0 |
| 16.2  | 0 | 0 | 1 | 0 | 0 |
| 16.4  | 0 | 0 | 1 | 0 | 0 |
| ⎡ 16.5 | 1 | 0 | 0 | 0 | 0 |
|   16.7 | 1 | 0 | 0 | 0 | 0 |
|   16.9 | 1 | 0 | 0 | 0 | 0 |
|   17.1 | 1 | 0 | 0 | 0 | 0 |
|   17.3 | 1 | 0 | 0 | 0 | 0 |
|   17.5 | 1 | 0 | 0 | 0 | 0 |
|   17.7 | 1 | 0 | 0 | 0 | 0 |
|   17.8 | 1 | 0 | 0 | 0 | 0 |
| 1 18.0 | 1 | 0 | 0 | 0 | 0 |
|   18.2 | 1 | 0 | 0 | 0 | 0 |
|   18.4 | 1 | 0 | 0 | 0 | 0 |
|   18.6 | 1 | 0 | 0 | 0 | 0 |
|   18.8 | 1 | 0 | 0 | 0 | 0 |
|   19.0 | 1 | 0 | 0 | 0 | 0 |
|   19.1 | 1 | 0 | 0 | 0 | 0 |
|   ⎣ 19.3 | 1 | 0 | 0 | 0 | 0 |
| 19.5  | 0 | 0 | 0 | 1 | 0 |
| 19.7  | 0 | 0 | 1 | 0 | 0 |
| 19.9  | 0 | 1 | 1 | 0 | 0 |
| 20.1  | 0 | 1 | 0 | 0 | 0 |
| 20.3  | 0 | 1 | 0 | 0 | 0 |

FIG.34B

| | GROUP | | | | |
|---|---|---|---|---|---|
| | ① | ② | ③ | ④ | ⑤ |
| 20.4 | 0 | 0 | 1 | 0 | 0 |
| 20.6 | 0 | 1 | 0 | 0 | 0 |
| 20.8 | 1 | 0 | 0 | 0 | 0 |
| 21.0 | 1 | 0 | 0 | 0 | 0 |
| 21.2 | 0 | 1 | 0 | 0 | 0 |
| 21.4 | 0 | 1 | 0 | 0 | 0 |
| 21.6 | 0 | 0 | 1 | 0 | 0 |
| 21.7 | 0 | 0 | 1 | 0 | 0 |
| 21.9 | 0 | 1 | 0 | 0 | 0 |
| 22.1 | 0 | 0 | 0 | 0 | 1 |
| 22.3 | 0 | 0 | 0 | 0 | 1 |
| 22.5 | 0 | 1 | 0 | 0 | 0 |
| 22.7 | 0 | 1 | 0 | 0 | 0 |
| 22.9 | 0 | 0 | 1 | 0 | 0 |
| 23.0 | 0 | 0 | 1 | 0 | 0 |
| 23.2 | 0 | 0 | 0 | 0 | 1 |
| 23.4 | 0 | 0 | 0 | 0 | 1 |
| 23.6 | 0 | 0 | 0 | 0 | 1 |
| 23.8 | 0 | 1 | 0 | 0 | 0 |
| 24.0 | 0 | 0 | 1 | 0 | 0 |
| 24.2 | 0 | 0 | 1 | 0 | 0 |
| 24.3 | 0 | 0 | 0 | 0 | 1 |
| 24.5 | 0 | 0 | 1 | 0 | 0 |
| 24.7 | 1 | 0 | 0 | 0 | 0 |
| 24.9 | 1 | 0 | 0 | 0 | 0 |
| 25.1 | 0 | 0 | 1 | 0 | 0 |
| 25.3 | 1 | 0 | 0 | 0 | 0 |
| 25.5 | 1 | 0 | 0 | 0 | 0 |
| 25.6 | 1 | 0 | 0 | 0 | 0 |
| 25.8 | 1 | 0 | 0 | 0 | 0 |
| 26.0 | 0 | 0 | 1 | 0 | 0 |
| 26.2 | 0 | 1 | 0 | 0 | 0 |
| 26.4 | 0 | 0 | 1 | 0 | 0 |
| 26.6 | 0 | 0 | 0 | 0 | 1 |
| 26.8 | 0 | 0 | 0 | 0 | 1 |

FIG.34C

VASCULAR ACOUSTIC EMISSION ANALYSIS IN A BALLOON ANGIOPLASTY SYSTEM

This application is a continuation of application Ser. No. 08/786,483, filed Jan. 21, 1997.

The present invention is directed to a method and system for analysis of vascular acoustic emission signals generated during balloon angioplasty treatment of plaque deposits in vascular lumens. More particularly, the invention is directed to a system and method for analyzing acoustic emission signals from plaque cracking during angioplasty to deduce vascular trauma. Further, the invention concerns particularly the identification of specific events occurring during angioplasty therapy, such as stretching of plaque, onset of plaque cracking, following the various stages of plaque cracking and therapeutic completion of angioplasty, discerning stretching of vascular tissue, the onset of vascular tissue failure, correlation of plaque cracking signature with post procedure effectiveness and characterization of asymmetric plaque deposits to adjust angioplasty treatment.

Atherosclerosis is a multifactorial disease process involving subendothelial accumulation of lipid and necrotic debris compounded by smooth muscle cell proliferation and connective tissue synthesis. This process is thought to begin in childhood, and progresses toward formation of occlusive lesions that may ultimately inhibit normal blood flow and vascular reactivity. Clinical manifestations of atherosclerotic disease are derived from compromised perfusion and the fact that cracks, fissures, or ruptures of advanced lesions lead to ischemic thrombosis and embolism. Atherosclerosis has been identified as the principal cause of death in Western countries.

The severe health impact of atherosclerotic disease has been the impetus for numerous short-term and long-term initiatives directed at treating atherosclerosis. Despite progress by preventative public health and pharmacological treatments directed toward reducing the long-term incidence and severity of atherosclerosis, vascular disease remains the leading cause of death in the United States. This fact, together with the difficulties involved with detecting atherosclerosis before the onset of deleterious clinical manifestations has focused the immediate future of atherosclerosis therapy on acute, catheter-based interventional devices designed to remove or remodel obstructive lesions.

Balloon angioplasty (hereinafter "BA") has proven to be a successful, albeit imperfect, method of recannulating atherosclerotic vessels and improving blood flow through them. Since its introduction in 1977, BA has achieved widespread acceptance, and emerged as the preeminent acute, non-surgical treatment modality for atherosclerosis. The basis for the BA technique is to improve blood flow through a stenosed segment by increasing its residual lumen area. To achieve this goal, BA utilizes a catheter-mounted balloon to apply a radially directed distending force to the arterial wall. The radial force imposed on the diseased wall is a function of inflation pressure, lesion morphology, and balloon geometry. The "controlled injury" that results from this procedure causes dilation of the diseased segment through a complicated process. The technique results in sustained improvement in the majority of appropriately selected patients with low morbidity and little recovery time.

The mechanisms of BA are fundamentally traumatic to arterial tissue. Accumulated research demonstrates that BA involves: superficial disruption of the intima, fracture of atheromatous plaque, crack propagation, and copious stretching of arterial tissue. Dissection secondary to crack propagation is a particularly insidious form of BA-induced arterial trauma involving laceration and/or cleavage of the arterial wall. Dissection has been implicated as a contributing factor to both acute procedural complications (e.g., abrupt reclosure, ischemia, myocardial infarction, emergency surgery, and coronary microembolization), and chronic restenosis of the treatment site. Although the presence of dissection has been shown to be an important predictor of clinical outcome following BA intervention, dissection severity may be a better correlate to outcome.

Identification of BA-induced dissection can allow prediction of patients at risk for developing complications. It has been established that the presence and extent of BA-induced arterial trauma can be important predictors of acute vessel closure or late restenosis. From this perspective, the procedural goal of BA is to achieve the maximum increase in luminal diameter while inflicting the minimal amount of trauma upon the artery. Unfortunately, optimal guidance of the BA procedure toward this goal is not straightforward due to the complicated interaction between the balloon and lesion in vivo. Additionally, it is extremely difficult to accurately assess vascular trauma end-points thereby allowing stratification of patients according to risk probability with conventional techniques. A method that permits immediate, on-line recognition of plaque fracture and vascular injury severity can provide a mechanism for procedural guidance and improved outcome. Clinically, however, this objective is hindered by the ability of conventional diagnostic techniques, including angiography and intravascular ultrasound, to accurately identify dissection or soft tissue trauma. Angiographic evidence of dissection, for example, involves identification of intraluminal filling defects, extraluminal extravasation of contrast material, linear luminal densities, or luminal staining. These interpretations are subjective, not amenable to conventional quantitative angiographic analysis, and cover a wide range of potential injury types. Intravascular ultrasound imaging techniques, by comparison, also suffer inherent limitations (e.g., calcific shadowing, near-field distortion, catheter-to-vessel alignment artifact, etc.) which can preclude consistent characterization of vascular trauma.

It is therefore an object of the invention to provide an improved system and method for application and analysis of BA therapy.

It is also an object of the invention to provide a novel system and method for analysis of vascular acoustic emission data generated during BA treatments to enhance BA therapy.

It is yet a further object of the invention to provide an improved system and method for analysis of acoustic emission signals from BA treatment utilizing a non-invasive piezoelectric transducer for detection of the signals.

It is another object of the invention to provide an improved system and method for analyzing BA induced acoustic emission data to identify onset of vascular trauma.

It is yet another object of the invention to provide an improved system and method for analyzing acoustic emission data from vascular tissue and plaque being deformed during BA therapy to identify the onset of plaque cracking, ongoing plaque fragmentation and plaque rearrangement during therapy and therapeutic completion of BA.

It is an additional object of the invention to provide a novel system and method for dynamically controlling BA therapy in real time utilizing control information derived from acoustic emission data generated during the BA therapy.

It is a further object of the invention to provide a novel system and method for analyzing acoustic emission data generated during BA treatment to identify vascular tissue stretching and dissection.

It is likewise an object of the invention to provide an improved system and method for analyzing acoustic emission data generated during BA treatment to correlate plaque cracking acoustic spectra and vascular tissue rupture spectra with post procedure effectiveness.

It is also another object of the invention to provide an improved system and method for performing mathematical evaluation of acoustic emission data generated during BA treatment to identify useful indicators of the dynamic effect of BA treatment.

It is yet an additional object of the invention to provide a novel system and method for performing neural net analysis of acoustic emission data generated during BA treatment to characterize vascular trauma and indicators of effective BA therapy.

It is yet a further object of the invention to provide an improved system and method for detection of acoustic emission signals from BA treatment using piezoelectric transducers, such as polyvinylidene fluoride (hereinafter "PVDF"), as a transducer.

It is also a further object of the invention to provide a novel device and method for sensing acoustic emission signals from BA treatment using at least one of a metallized PVDF balloon and a metal/PVDF/metal layer on a balloon.

It is yet an additional object of the invention to provide an improved device and method for sensing acoustic emission signals from BA treatment using a PVDF containing balloon structure and a PVDF differential sensor layer disposed on or within a catheter guide lumen or shaft associated with a balloon.

It is still another object of the invention to provide a novel device for performing BA using a plurality of balloons, each having separate transducer elements for sensing acoustic emission signals generated during BA treatment.

It is yet a further object of the invention to provide a novel device for performing BA using a plurality of sensors on a balloon, each separate sensor comprised of a transducer element for at least one of sensing acoustic signals, sensing pressure levels exerted by the balloon or generating vibrations for therapeutic applications.

It is also another object of the invention to provide an improved method of sensing acoustic emission signals arising from BA using a plurality of transducer elements coupled to different balloon elements used to perform BA.

It is yet another object of the invention to provide a novel device for performing BA using a plurality of PVDF transducer elements coupled to one or more balloons used for performing BA treatment.

It is in addition an object of the invention to provide an improved BA device having a plurality of piezoelectric transducers, such as PVDF cylindrical transducer elements, for performing detection of acoustic emission signals generated during BA treatment.

It is still another object of the invention to provide a novel BA device having a pattern of PVDF transducer material arranged to be particularly sensitive to selected BA induced acoustic emission signals and thereby provide analysis of plaque structure, dynamics of plaque rearrangement during BA and structural analysis of vascular tissue.

It is also another object of the invention to provide an improved BA device and method of use with the device including a stent to stabilize arteries subjected to BA treatment.

It is yet a further object of the invention to provide a novel BA system and method of performing BA using a stent to support arterial walls with a PVDF transducer sensing acoustic emission signals characteristic of plaque rearrangement as confined by the stent.

It is still a further object of the invention to provide an improved method of analyzing acoustic emission signals arising from BA treatment by energy content or power analysis, wavelet analysis, time domain analysis, neural network analysis or by Fourier transformation and neural network analysis.

It is still an additional object of the invention to provide a novel system and method for control of BA treatment utilizing acoustic emission signals arising during BA to arrest vascular trauma by reducing pressure being applied to an artery under treatments.

It is yet an additional object of the invention to provide an improved system and method for control of BA treatment involving positioning a stent based on pressure and acoustic emission signals sensed during the BA treatment.

It is still a further object of the invention to provide a novel system and method of performing BA utilizing a vibrating balloon.

It is also another object of the invention to provide an improved system and method of using a PVDF transducer coupled to, or an integral part of, a balloon for BA to perform spatial localization procedures for identifying plaque and arterial features before, during and after performing BA.

It is also an object of the invention to provide a novel method and system for performing BA employing a PVDF which contains one or more balloon elements to apply time and frequency varying voltages, causing variable balloon vibration to enhance BA treatment.

It is yet an additional object of the invention to provide an improved system and method for monitoring BA treatment using analysis of acoustic emission signals arising from BA to generate output information, such as audio signals, video information and visual status signals, to assist the clinician in performing BA.

It is also a further object of the invention to provide a novel system and method for varying and terminating BA treatment based on analysis, such as frequency spectrum analysis, of BA induced acoustic emission signals indicating onset of vascular tissue dissection.

It is still another object of the invention to provide an improved system and method using an automated apparatus to sense onset of vascular tissue dissection and enable release of the pressure being applied to the balloon.

It is also yet another object of the invention to provide a novel system and method for application of pattern recognition methodologies to correlate acoustic emission time and/or frequency spectra with selected events occurring during BA treatments.

These and other objects and advantages of the inventions will become apparent from the following detailed description and the figures described below.

BRIEF DESCRIPTION OF THE DRAWINGS

FIG. 1A is a balloon angioplasty ("BA") system constructed in accordance with the invention, and FIG. 1B is a cross section along line 1B—1B;

FIG. 3A is a BA system having an additional differential sensor, and FIG. 3B is a cross section taken along line 3B–3B in FIG. 3A;

FIG. 10 illustrates a gray scale plot of Fourier transformed BA acoustic emission signals showing frequency amplitude for a given frequency and time during the period of BA treatment and a window increment of about 0.1 seconds with a 50% window overlap;

FIG. 11 shows another gray scale plot like FIG. 10 but the window increment is about 0.1 seconds with a 25% window overlap;

FIG. 14A illustrates a time segment taken from the full BA treatment time period.

FIG. 17A illustrates a time segment taken from the full BA treatment time period.

FIG. 27A illustrates a time segment taken from the full BA treatment time period.

FIG. 31A depicts a balloon dilation sequence; FIG. 31B shows 57.93 seconds of acoustic emission information; and FIG. 31C depicts in vitro data collected over 125.96 seconds;

FIGS. 34A–33C illustrate a table showing neural network categorization of frequency amplitude data into groups.

DETAILED DESCRIPTION OF PREFERRED EMBODIMENTS

A balloon angioplasty system constructed in accordance with one form of the invention is shown generally at 10 in FIG. 1A. The balloon angioplasty system (hereinafter the "system") 10 includes a catheter 14 and balloon 18 which has a vibration sensing piezoelectric transducer 22. Therefore, the system 10 not only performs conventional balloon angioplasty ("BA") treatments but also detects acoustic emissions (mechanical vibrations) generated during BA procedures from vascular tissue being stretched and from plaque lesions fracturing and otherwise being distorted.

Figure 2A:
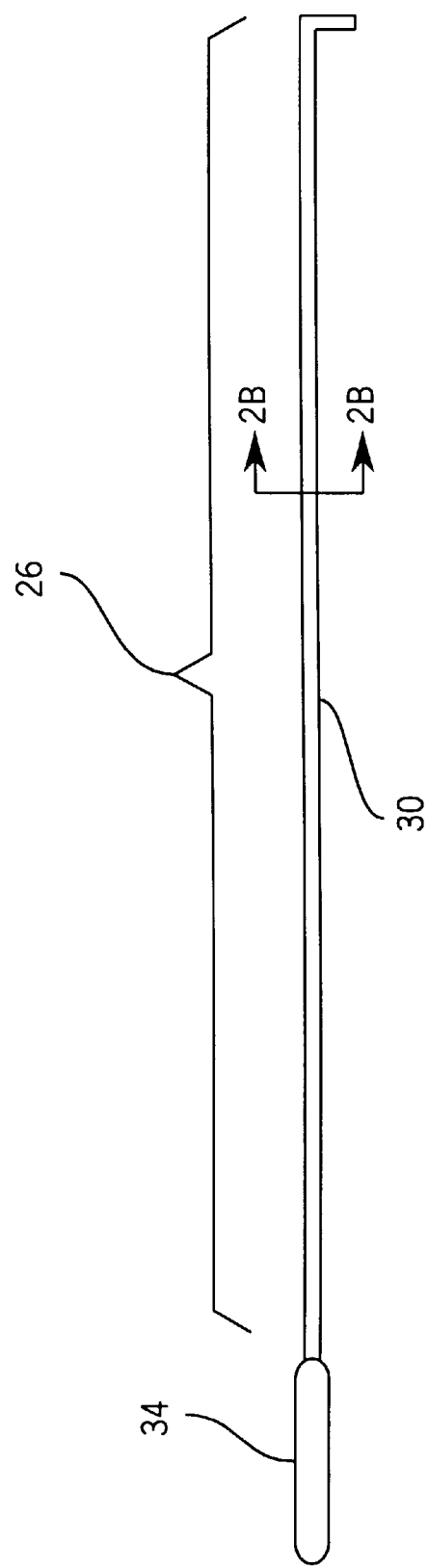
FIG. 2A is a prior art conventional BA catheter and FIG. 2B is a cross section along 2B—2B in FIG. 2A.
Figure 2B:
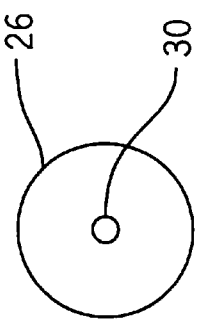

BA dilation catheters are well known and have been commercially marketed since the late 1970s. Such a catheter is shown in FIGS. 2A and 2B and consists of a circular cross section cylindrical tube 26, typically having an O.D. of about 1.5 mm and a length of 135 cm. The tube 26 has at least one internal catheter shaft 30, shown best in FIG. 2B, running parallel to the longitudinal axis of the tube 26. The catheter shaft 30 in a conventional system can provide a passageway for any electrical connection to the transducer 22 shown in FIG. 1A and input of fluid to inflate a reversibly inflatable balloon 34 at the distal end of the tube 26. The shape of the balloon 34 varies with the manufacturer and the particular clinical application. These tubes 26 are generally constructed by extrusion and thermal processing of polymer materials, such as polyvinyl chloride and polyethylene.

The piezoelectric transducer 22 shown in FIG. 1A generates an electrical charge and voltage, either of which can be used to evaluate the amplitude and frequency of an imposed mechanical deformation. Mechanical vibrations (acoustic emissions), which are generated by stressed vascular tissue and plaque lesions undergoing distortion, propagate radially outward from their source. The mechanical vibrations impinging upon the piezoelectric transducer 22 are converted to high fidelity, electrical signals representative of the emissions which can be analyzed in the manner described hereinafter.

In other forms of the invention the acoustic emissions generated during BA treatment can be sensed by other means and analyzed in the manner described hereinafter. Other suitable means for sensing the acoustic emissions include, for example, well known optical, capacitive and acceleration techniques.

In the most preferred form of the invention the piezoelectric transducer 22 is utilized to sense the acoustic emissions generated by BA treatment using the balloon 18 of the system 10. The preferred piezoelectric material is polyvinylidene fluoride (hereinafter "PVDF"), such as KYNAR, a trademark of AMP, Inc., Valley Forge, Pa. It should be understood that numerous other conventional piezoelectric materials can be used to construct the transducer 22; but PVDF has the following important advantages: it has a very durable surface metallization, has a high voltage-to-strain ratio, wide frequency operational range (0.001 Hz–1.0 GHz), excellent dynamic range ($10^8$–$10^6$ psi), low acoustic impedance (only 2.5 times that of water), desirable mechanical strength and durability, exhibits excellent biocompatability over a wide temperature range and necessitates only small thickness due to its strength and flexibility which facilitate attachment to the balloon 18 or its use as a balloon material itself. PVDF, as well as other well known piezoelectric polymers, generate large voltages upon deformation but do not require external source electrical excitation and produce very little current, thereby providing a low electrical shock risk.

In one embodiment shown in FIGS. 1A and B, the piezoelectric transducer 22 is a rectangular piece of PVDF film of about twenty-eight microns thickness. This film form of the transducer 22 of PVDF is surface mounted onto the balloon 18 using commercially available adhesives. In the embodiment the film transducer 22 is coupled to the inner circumferential surface of the balloon 18 to minimize any possible effect of the film transducer 22 on the BA treatment. In another embodiment the film transducer 22 was coupled to the exterior surface of the balloon 18. (See Example I). The PVDF material has an acoustic impedance quite similar to common materials used to construct the balloon 18. Thus, mounting the film transducer 22 inside the balloon 18 will thus likely cause only minor dampening and distortion of the acoustic emission signals. Moreover, PVDF has a high sensitivity for small amplitude acoustic emissions, enabling detection of signals characteristic of the details of BA treatment.

In the embodiment having the film transducer 22 coupled to the inside surface of the balloon 18, electrical wires 42 (typically about 1 mm diameter) are coupled by conductive epoxy to a pre-metallized surface layer 46 (see FIG. 1B) disposed adjacent the interior surface of the balloon 18. The electrical wires 42 then pass through the catheter shaft 30 (best seen in FIG. 1B) terminating at a proximal end 50 in a standard connector 54 which interfaces to external instrumentation 58.

The external instrumentation 58 provides amplification, filtration, processing and display functionalities using well known electronic devices. As will be described hereinafter, processing of the sensed acoustic emission signals provides further advantages in characterizing the effect of the BA treatment and optimization of that treatment.

In another embodiment, the transducer 22 can also be used to output time and frequency varying mechanical vibrations to the balloon 18 for therapeutic treatment of plaque lesions, such as, improved plaque compaction. These vibrations can be used to complement the pressure being applied by the balloon 18 being inflated by fluid.

In yet another aspect of the invention, the feature of the piezoelectric transducer 22 having high sound pressure sensitivity (level and distribution of pressure) enables accurate placement of a stent 90 shown in phantom in FIG. 1A. The stent 90 is used in a well known way to establish a well defined open channel through an artery and act to prevent restinosis or reclosure of the artery at that location. In placement of the stent 90, it is plastically deformed and deployed by inflation of the balloon 18. In order to insure the stent 90 is in full opposition to the surrounding vascular tissue forming the passage of the artery, the transducer 22 can monitor the acoustic emission signals. By virtue of prior experimental work, one can establish an acoustic emission signal characteristic of such full opposition and can also thus discern lack of such opposition which creates undesirable gaps between the stent and the surrounding vascular tissue. These gaps consequently give rise to different acoustic emission signals, enabling detection of such conditions, thereby allowing the physician to deploy the stent 90 until full opposition has occurred. When properly deployed, the stent 90 will prevent closure of the artery due to any vascular tissue spasm and also alleviate problems associated with tissue flaps created by dissection which could cause obstruction of the artery.

Isolation of acoustic emission signals characteristic of vascular tissue and plaque deformation is enhanced by removal of artifacts and extraneous unwanted noise signals. Table I below summarizes various physiological sound sources and their frequency range.

TABLE I

| Physiological Sound Source | Frequency Range (Hz) |
| --- | --- |
| Heart Sounds | 25–2000 |
| Arterial Blood Pressure | 0–50 |
| Arterial Blood Flow | 0–100 |
| Respiratory Sounds | 0–40 |

The spectral distribution of vascular acoustic emission energy will not only include useful information about cracking and distortion of plaque and stretching and rupture or dissection of arterial tissue, but will also include unwanted noise in the form of extraneous mechanical vibrations associated with cyclic blood pressure, blood flow, and respiration as well as electrical noise pick-up, such as 60 Hz noise, and cardiac sounds (e.g., valve closure, regurgitation, etc.). Many of these noise signals will contain frequency components which overlap the domain of vascular acoustic emission signals to be analyzed. Consequently, these sources of signal contamination require additional treatment. One possible approach to remove unwanted noise is to use standard differential amplification techniques in which the difference between two signals is amplified. Utilization of this technology would require integrating an additional differential piezoelectric sensor 62 (see FIG. 3) into the system 10 that is exposed to extraneous sounds but not significant levels of vascular acoustic emission. The difference in signals detected between the vibrations detected by this additional sensor 62 and the one incorporated into the dilation balloon 18 (which is exposed to both vascular AE and extraneous physiological sounds) is ultimately the signal processed by the instrumentation 58. The differential sensor 62 is also connected to the electrical wires 42 through a radial hole 60 in the catheter shaft 30 (see FIG. 3B) and a radial hole 61 in the catheter 14 (see FIG. 3A).

Figure 4:
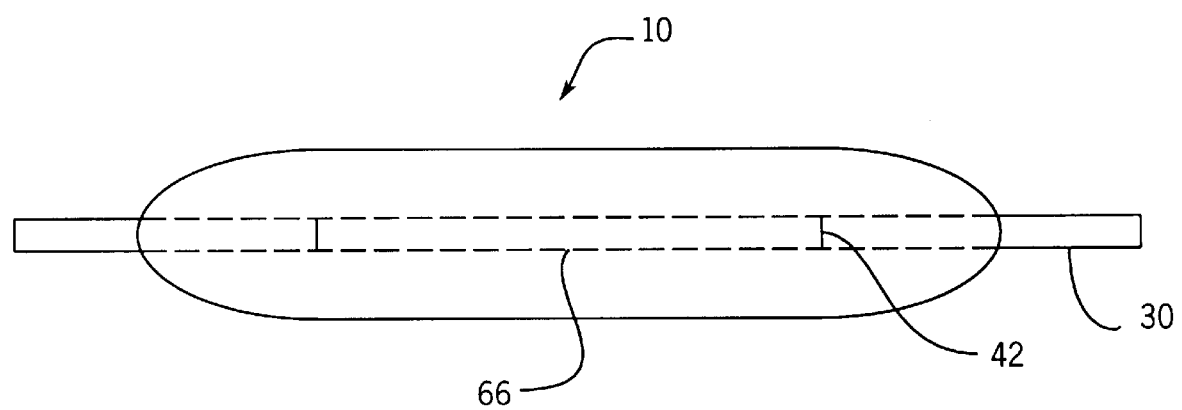
FIG. 4 is another BA system of the invention with a piezoelectric sensor disposed on the exterior of the catheter disposed inside the balloon.

In another embodiment of the system 10 shown in FIG. 4, a piezoelectric transducer 66 is coupled directly to the external surface of the catheter shaft 30 within the volume confinement of the balloon 18. This embodiment exhibits the attendant advantages of: (1) an enhanced durability since the transducer 66 does not undergo motion or distortion during balloon inflation, (2) the integrity of the electrical connections and surface metallization for those connections would be better maintained, (3) the structure would be easy to fabricate, with electrical connections readily accomplished and ending with balloon attachment and (4) there would be a reduced tendency for the substrate lumen 30 to "ring" in response to excitation, thereby reducing unwanted signals.

The above-described systems 10 can be used to generate substantial acoustic emission information useful in improving the effectiveness of BA treatment. Of particular interest is the elimination and minimization of dissection of arterial tissues and other vascular trauma, as well as understanding the nature of plaque deformation during BA treatment. This and other information can provide a clinically useful methodology for establishing control of BA treatment, optimization of treatment and risk-stratification of patients based on likelihood of subsequent complications. A preferred method for analysis of the acoustic emission information can comprise pattern recognition methodologies which will be discussed hereinafter.

The ongoing acoustic emission information obtained by the system 10 can also be used to guide and control ongoing BA treatment or be used post-procedure to assess prognosis for the patient and whether any subsequent treatment or procedures need to be performed. The acoustic emission information can be displayed in real time on a visual display; and audio outputs of the spectral information can also be provided both before, as well as after, being processed by user-selected analytical methods.

Figure 5:
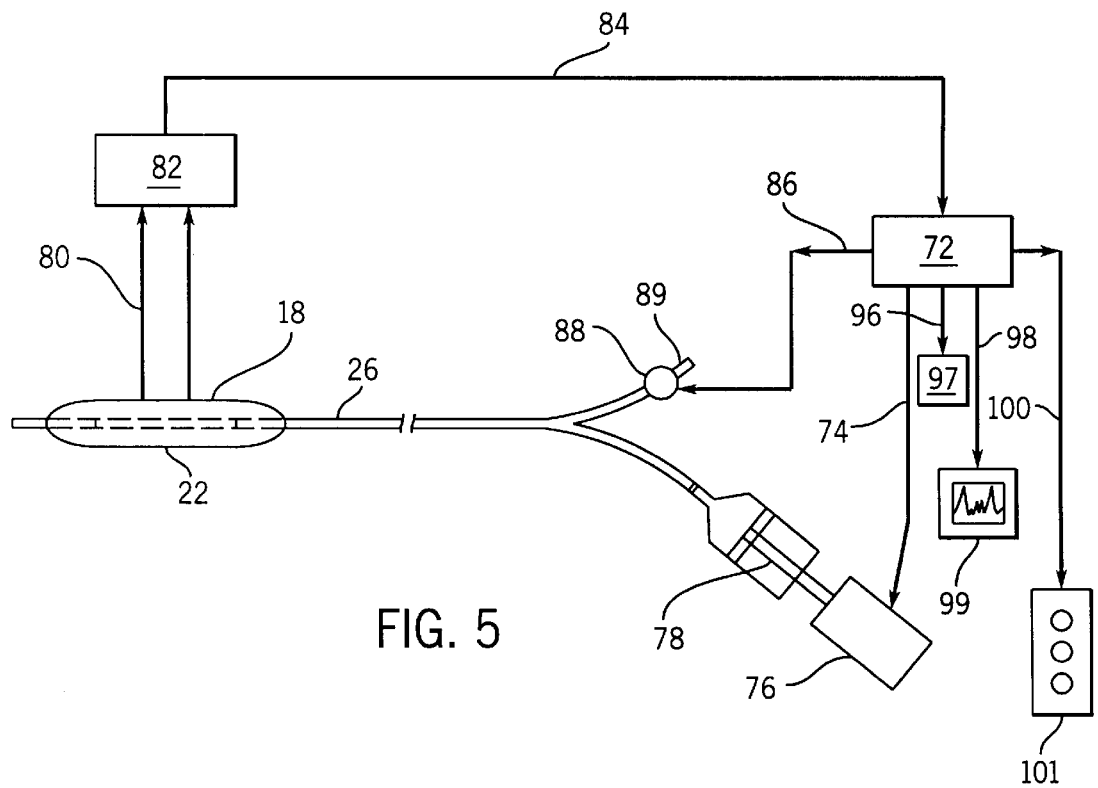
FIG. 5 illustrates a computer monitored and/or controlled BA system.

In the system 10 shown in FIG. 5 the BA treatment can be operated automatically in a portion, or all, of the BA procedure. The balloon 18 is inflated by application of fluid pressure through the catheter tube 26 by use of a syringe 70 coupled thereto. A computer 72 can include appropriate computer programming to output control signals 74 to a solenoid or piston 76 to advance or retract a syringe plunger 78 which delivers the fluid pressure through the catheter tube 26. Such computer programming is conventional and readily accomplished. The computer 72 is also responsive to acoustic emission signals 80 sensed by the transducer 22, then converted by A/D converter 82 in a typical manner to digital information from the analog state. The converter 82 outputs digitized acoustic emission signal 84 for analysis by the computer 72. The computer programming results in evaluation of this signal 84 and can continue to carry out the prearranged BA treatment according to a preprogrammed protocol, or the treatment can be varied or treatment terminated depending on the dynamic analysis of the acoustic emission signal 84. For example, if the computer analysis indicates the onset of vascular tissue dissection, the computer 72 can generate the control signals 74 to the solenoid or piston 76 to cease application of fluid pressure through the catheter tube 76. Also a second control signal 86 can be output from the computer 72 to actuate an affirmative pressure relief valve 88 (disposed adjacent system 89) to quickly reduce pressure being applied by the balloon 18 to the vascular tissue undergoing BA treatment. In addition, the computer 72 can generate other control signals to output audio information 96, video display information 98 and color activation signal 100. Again, such computer programming is conventional and readily accomplished. Therefore, a skilled physician can listen to the audio information 96 from a speaker 97 and make professional judgments concerning dynamic BA treatment. Further, the physician can likewise view the video display information 98 on display 99 (such as time or frequency spectra or information from pattern recognition analysis), and in response thereto the physician can intercede or allow automated BA treatment to continue. In addition, the colored status lights 101 can provide simple, clear indicators of the state of BA treatment, such as (1) a safe ongoing BA procedure, (2) an alert signal that indicates precursor signals characteristic of vascular dissection have been detected and (3) vascular dissection has in fact been detected.

Figure 6:
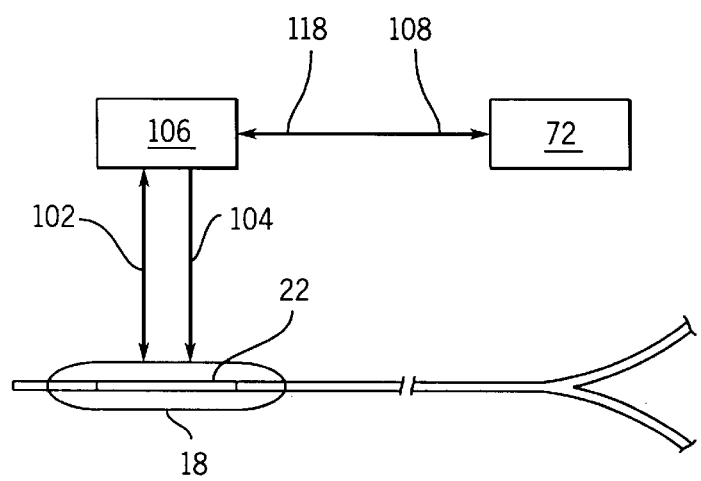
FIG. 6 illustrates a BA system having a matrix of transversely and/or longitudinally disposed transducers associated with the balloon element.

In another embodiment shown in FIG. 6 the balloon 18 includes a network of longitudinally and transversely disposed transducers 22. Such a network of the transducers 22, in particular, will allow identifying characteristic acoustic emissions from different circumferential areas of the plaque deposits undergoing BA treatment. Therefore, for example, acoustic emission signals 102 and 104 (arising from transducer intersections) can be isolated for each of the transducers 22 to identify different treatment results. This approach can also be used for the longitudinally disposed form of the transducers 22 to discern information associated with plaque cracking and vascular tissue stretching or dissection along the narrow area being monitored by each of the longitudinally disposed transducers 22. Consequently, the emission signals 102 and 104 are output to analog to digital converter 106 which provides output signal 108 for analysis by the computer 72.

In the embodiment of FIG. 6 the computer 72 can also act in accordance with computer programming to generate vibration control signals 110 for reverse conversion from digital to analog form and output to the selected transducer 22. These converted, analog form of the vibration control signals 110 actuate the selected transducer 22 which undergo vibrations which are in turn coupled to the vascular tissue and/or plaque in order to compact or otherwise treat the plaque lesions.

Figure 7:
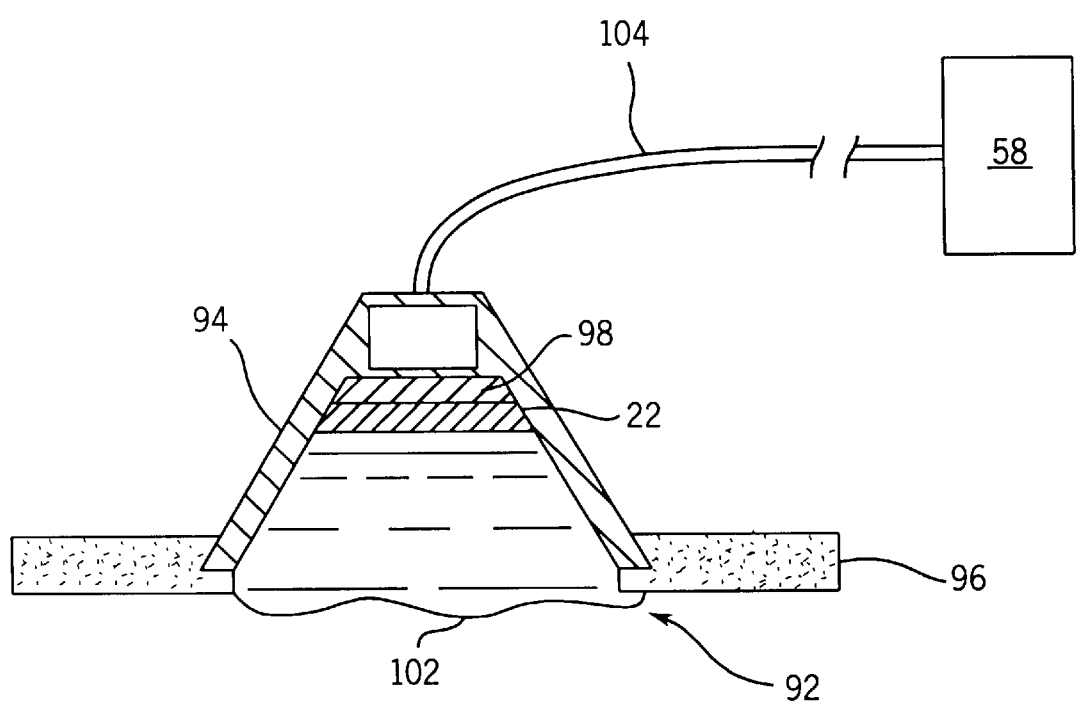
FIG. 7 illustrates a noninvasive, externally mounted piezoelectric transducer system for detection of acoustic emission signals.

In another form of the invention shown in FIG. 7, a non-invasive device 92 includes the piezoelectric transducer 22 (or other acoustic pickup device) for sensing the acoustic emission signals generated during BA treatment. The device 92 includes a conical housing 94 with an annular adhesive base 96 for direct attachment to the patient's chest wall. This housing 94 also provides a recessed geometry for the transducer 22 attached to a transducer backing 98, and pre-amplifier 100 acts to amplify the acoustic emission signals for output to the electronic circuitry 58 for further amplification and processing. It should be noted that recessing the transducer 22 from the patient's skin helps to minimize artifacts arising from patient motion. Further noise reduction is accomplished by using a sound attenuating material for the housing 94. In order to enhance sound detection by the transducer 22, an acoustic couplant gel 102 is disposed within the recess of the housing 94. A shielded cable 104 also helps to eliminate unwanted noise, such as 60 Hz line noise which can be quite dominant as noted by reference to FIGS. 10–12. Attendant advantages of the device 92 include (1) not requiring any modification of standard BA catheters, (2) improved signal to noise ratios by virtue of preamplification at the site of acoustic emission detection, (3) utility with many interventional therapies and (4) ease of clinical testing due to its passive, non-invasive nature.

Acoustic Emission Signal Analysis

As mentioned hereinbefore, it is useful to carry out analysis of acoustic emission information being accumulated during BA treatment or after treatment. Such analysis can be of benefit and be used during an ongoing BA treatment as well for post operative analysis of results and prognosis for the patient. The resulting analytical information can be output as audio information, visual displays and mathematical or numerical output.

To illustrate the value of acoustic emission analysis, data were accumulated by BA experiments carried out as described in Example II hereinafter. A variety of mathematical methodologies can be used to analyze the acoustic emission data and for purposes of illustration the following subsections describe some examples of useful approaches: (1) a spectrogram approach, (2) a sound pattern approach and (3) wavelet approach, all of which are frequency domain analyses and (4) also a time domain approach.

Figure 8:
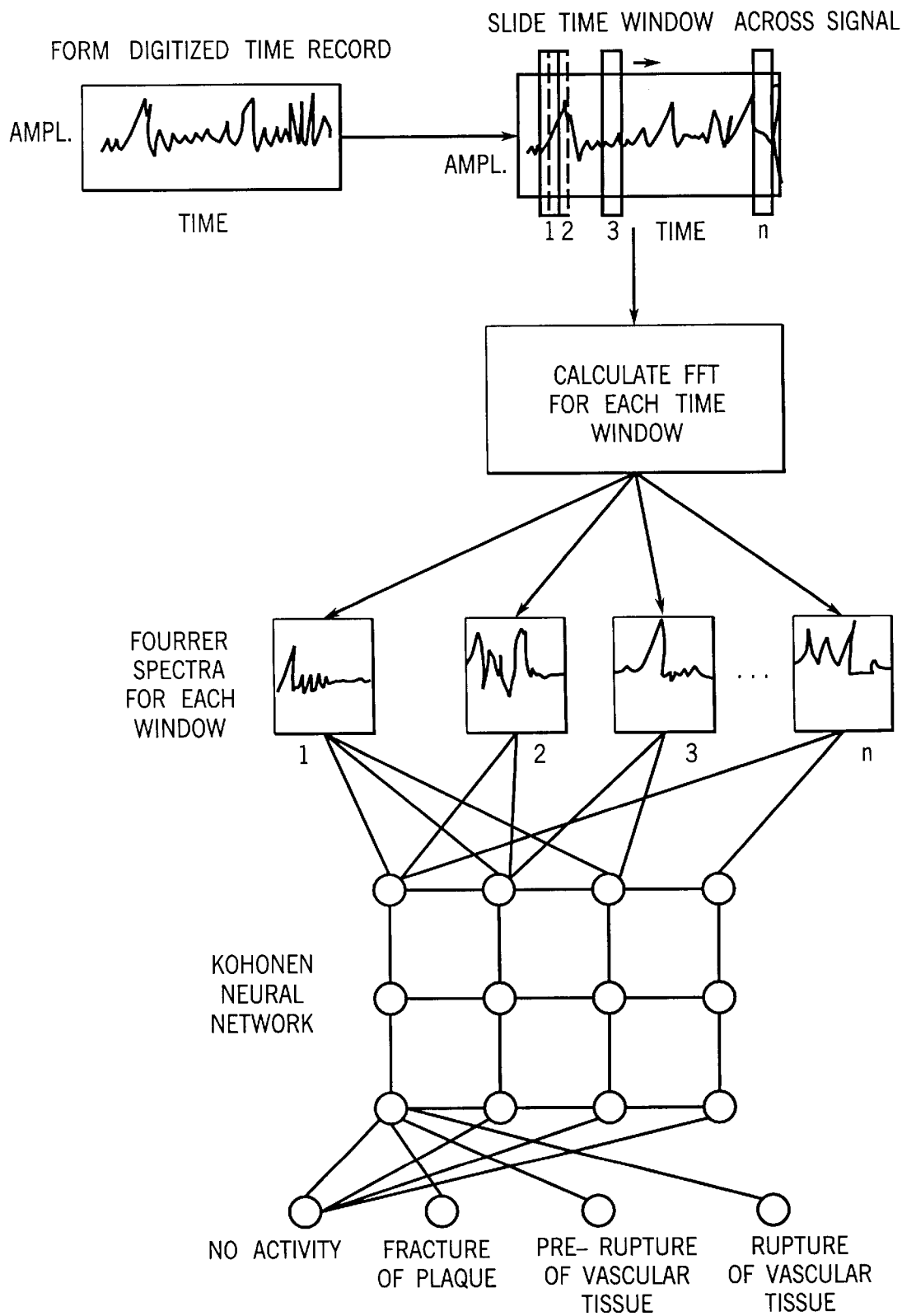
FIG. 8 shows a functional block flow diagram illustrating analysis of acoustic emission information by Fourier transform and probablistic methods.
Figure 9A:
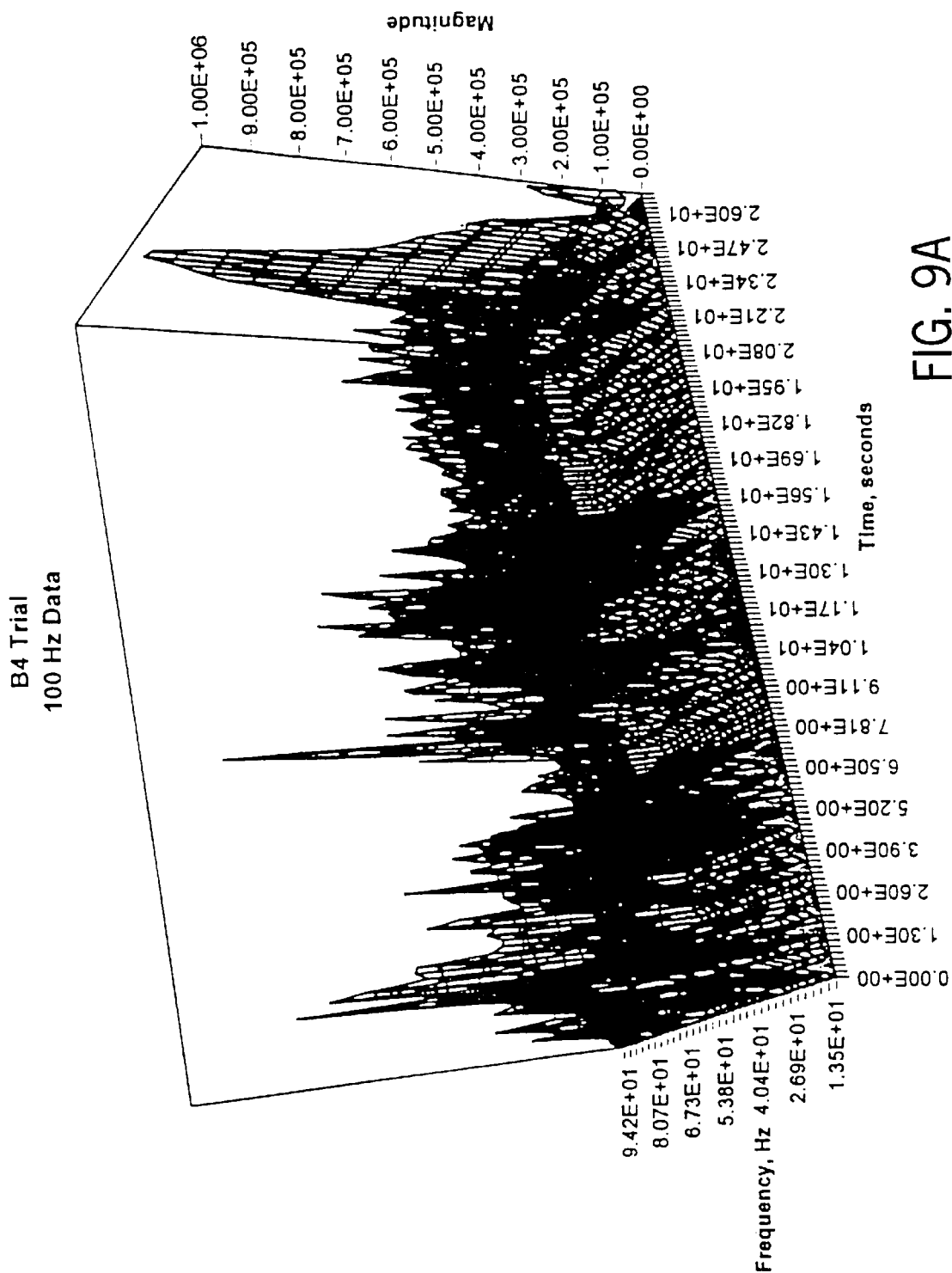
FIG. 9A illustrates a time frequency spectrogram over a 13–94 Hz band for a BA treatment; 9B shows another spectrogram over a 100–194Hz; 9C shows another spectrogram over a 200–296 Hz band; 9D shows another spectrogram over a 304–398 Hz band; 9E shows another spectrogram over a 406–500 Hz band; 9F shows another spectrogram over a 508–603 Hz band; 9G shows another spectrogram over a 611–705 Hz band; 9H shows another spectrogram over a 713–807 Hz band; 9I shows another spectrogram over a 815–909 Hz band; 9J shows another spectrogram over a 917–1010 Hz band; 9K shows another spectrogram over a 1020–1110 Hz band; 9L shows another spectrogram over a 1190–1280 Hz band; 9M shows another spectrogram over a 1990–2090 Hz band; and 9N shows another spectrogram over a 2240–2330 Hz band.
Figure 9B:
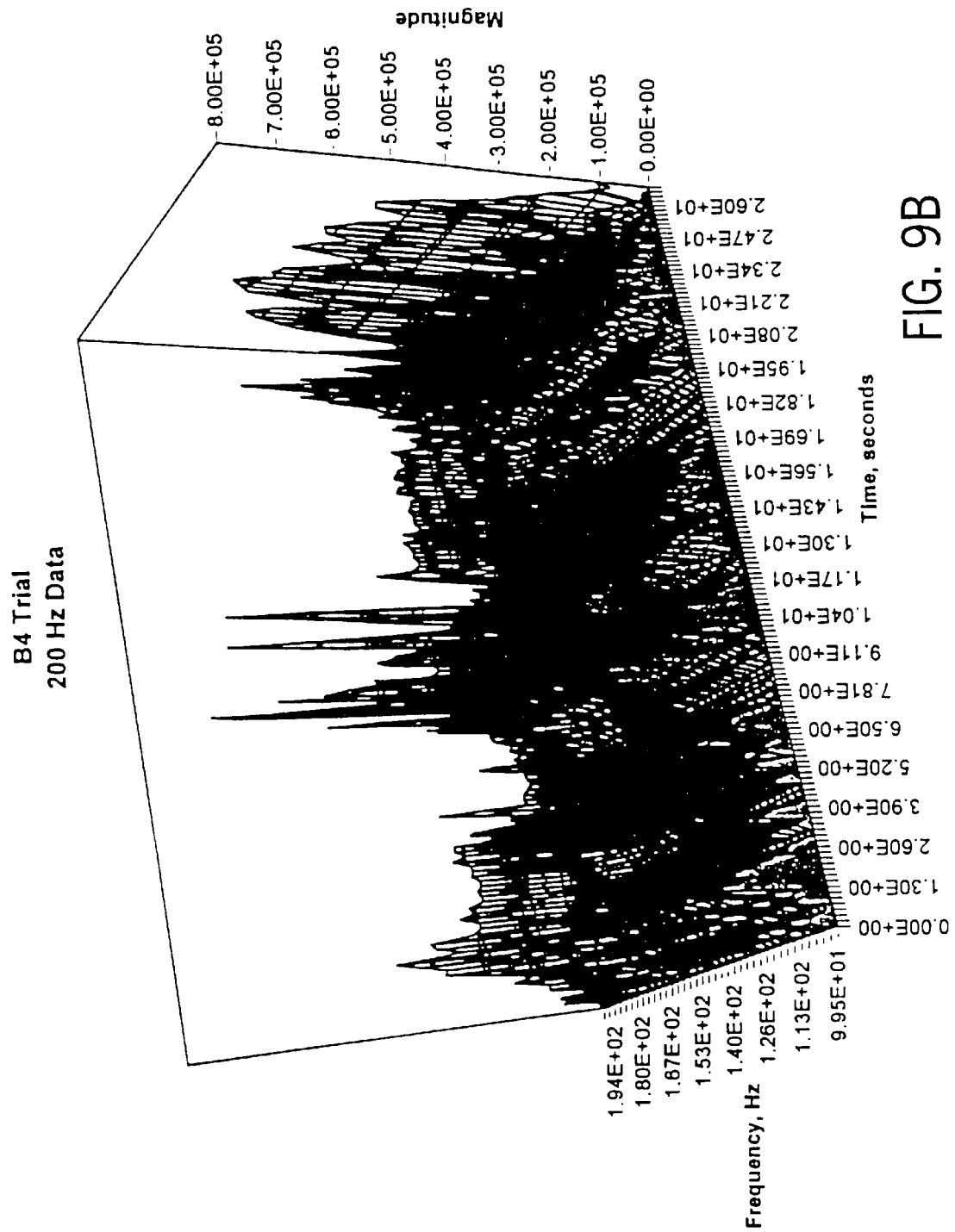
Figure 9C:
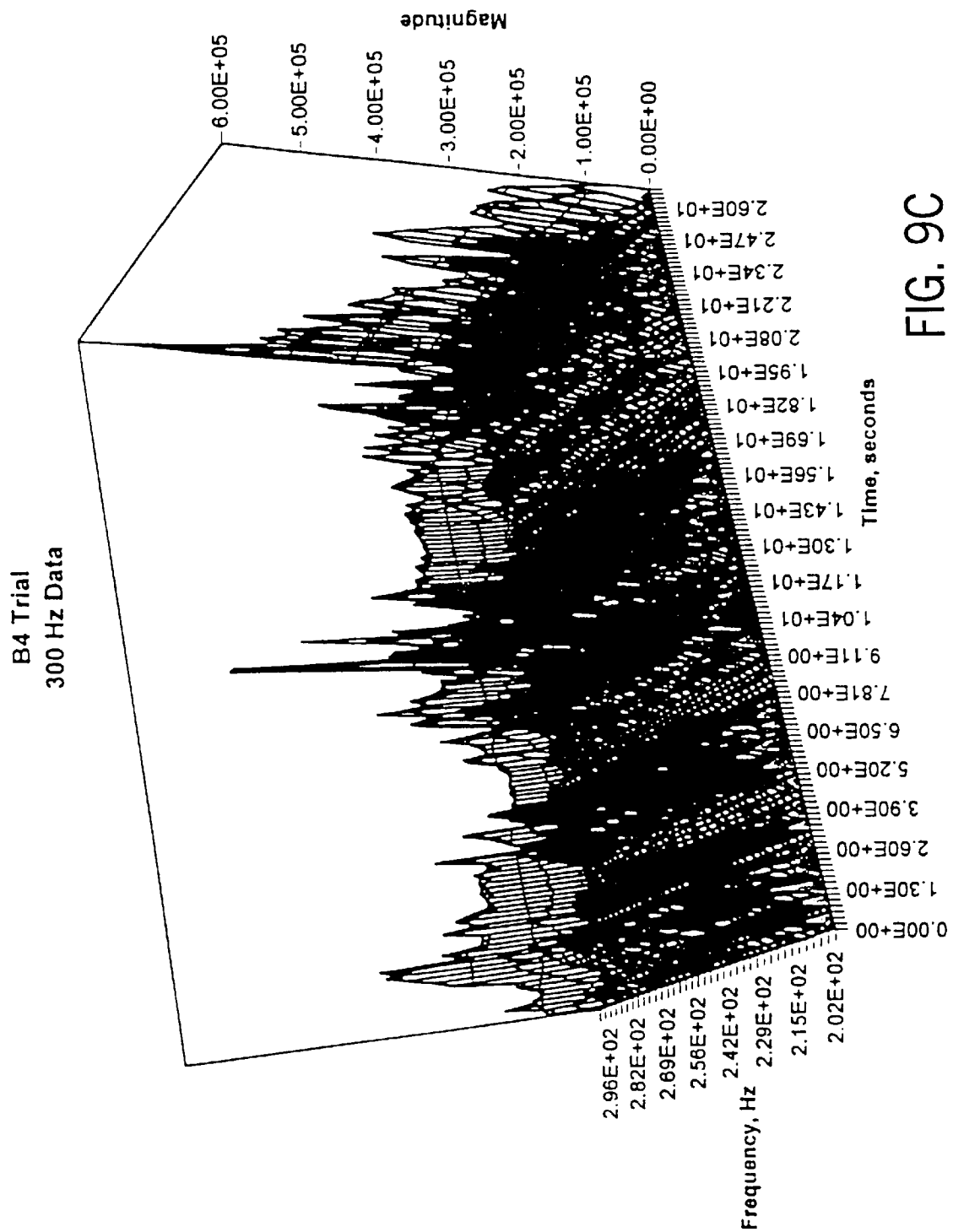
Figure 9D:
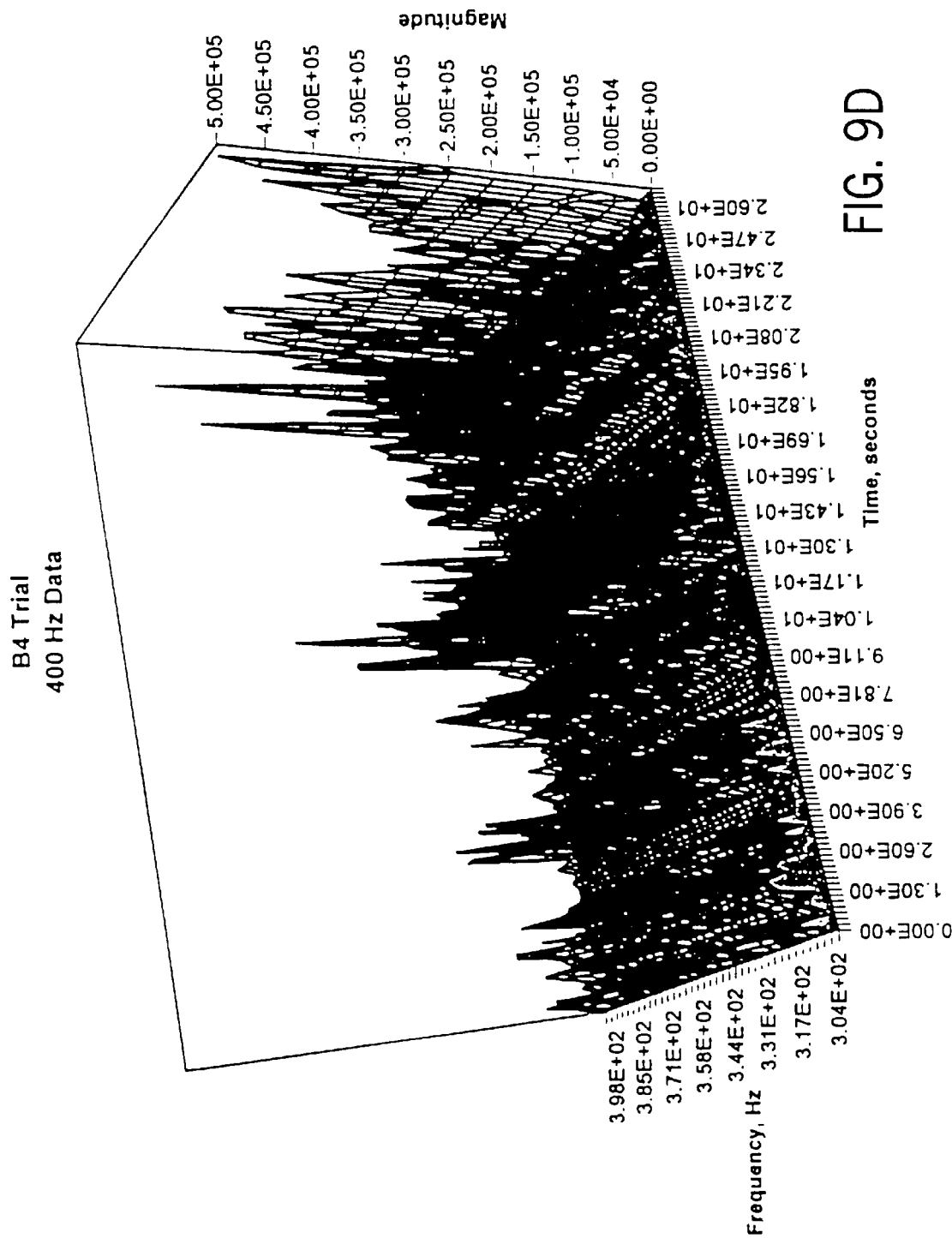
Figure 9E:
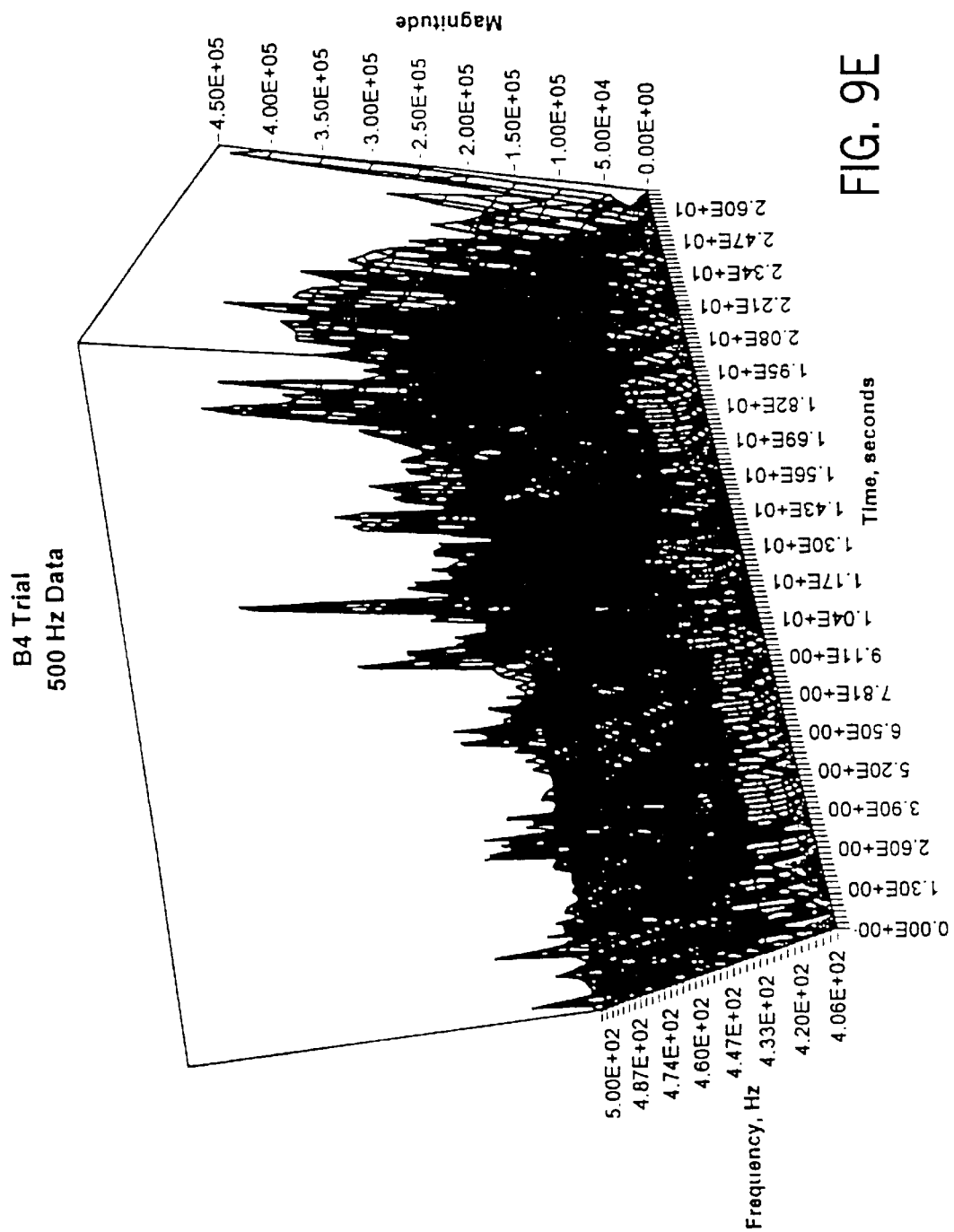
Figure 9F:
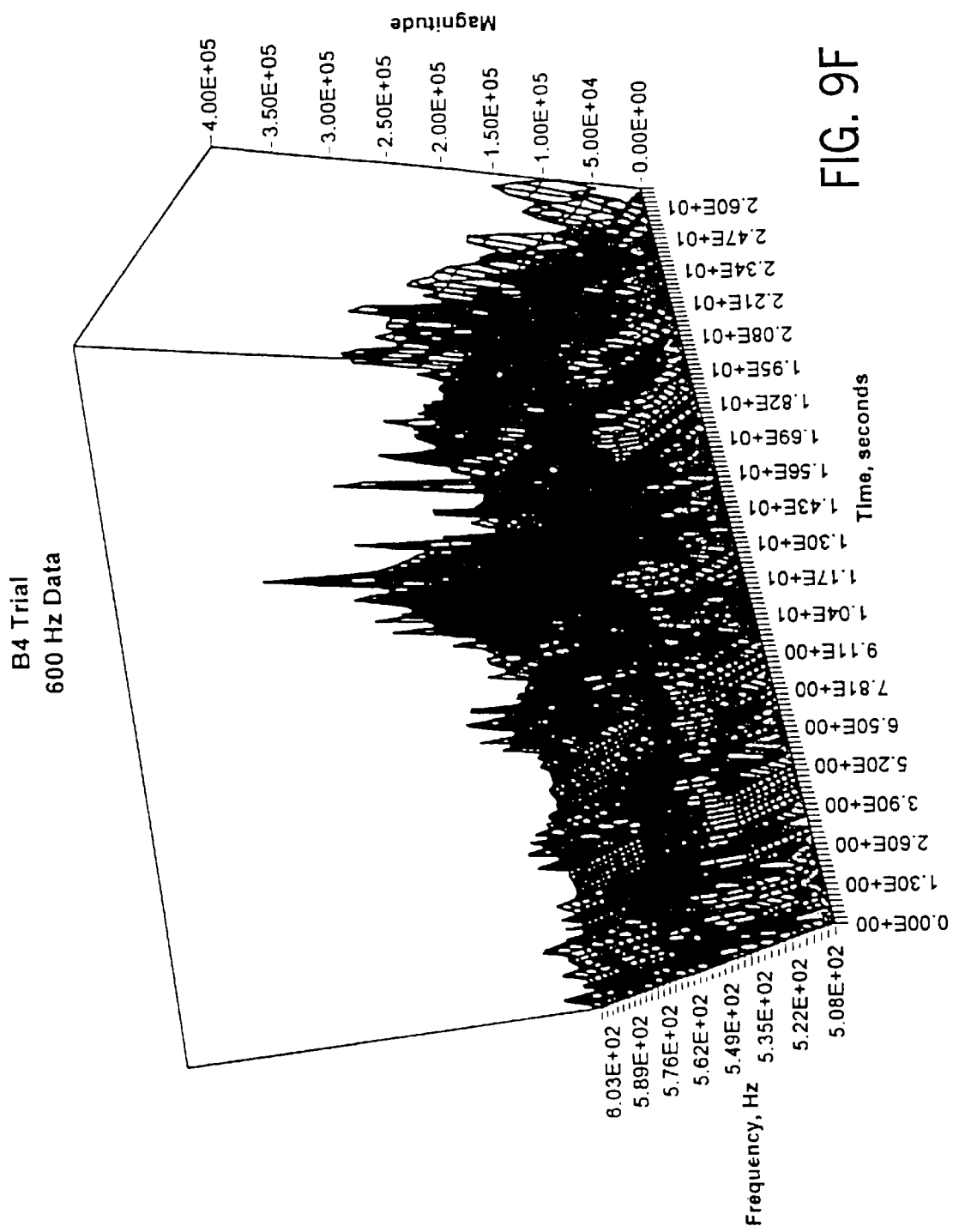
Figure 9G:
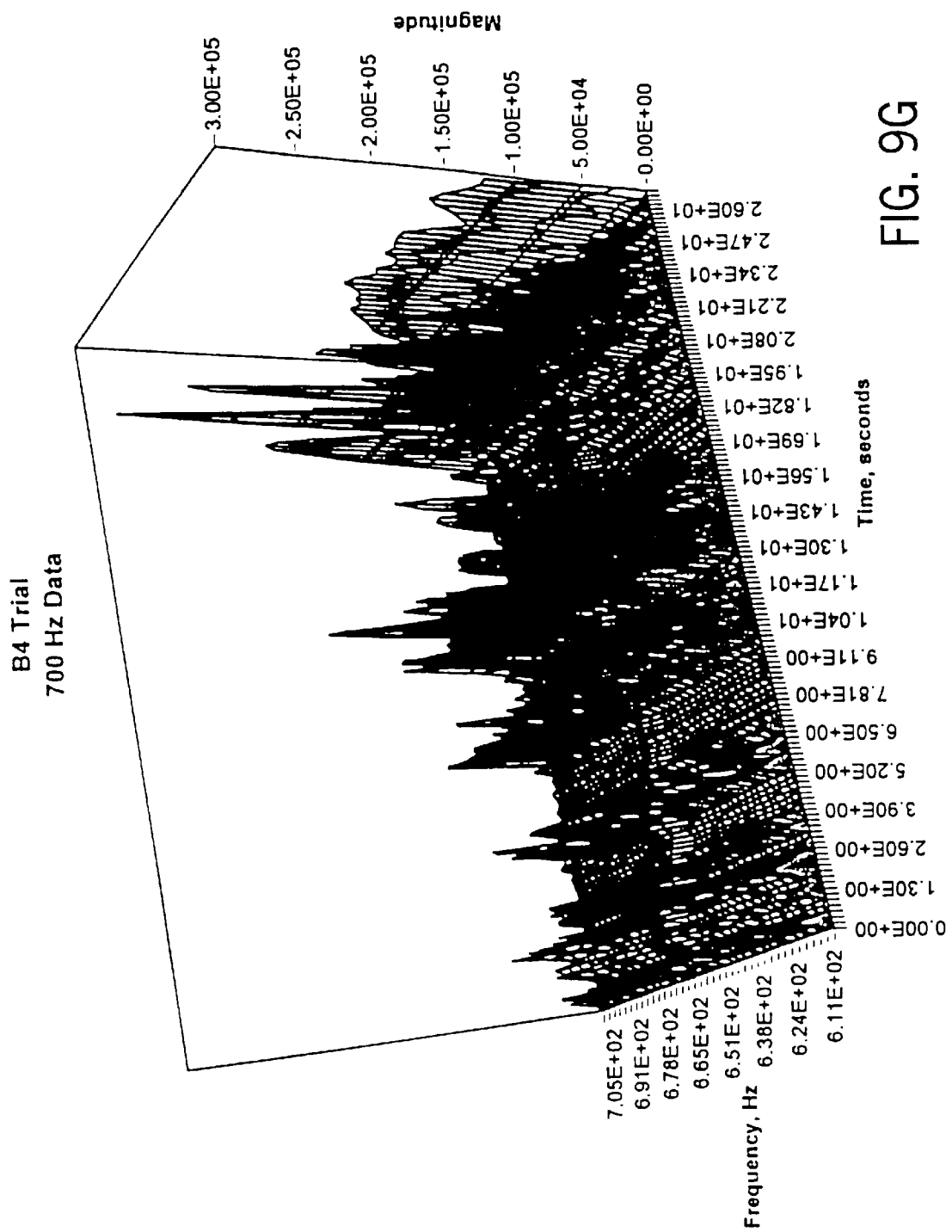
Figure 9H:
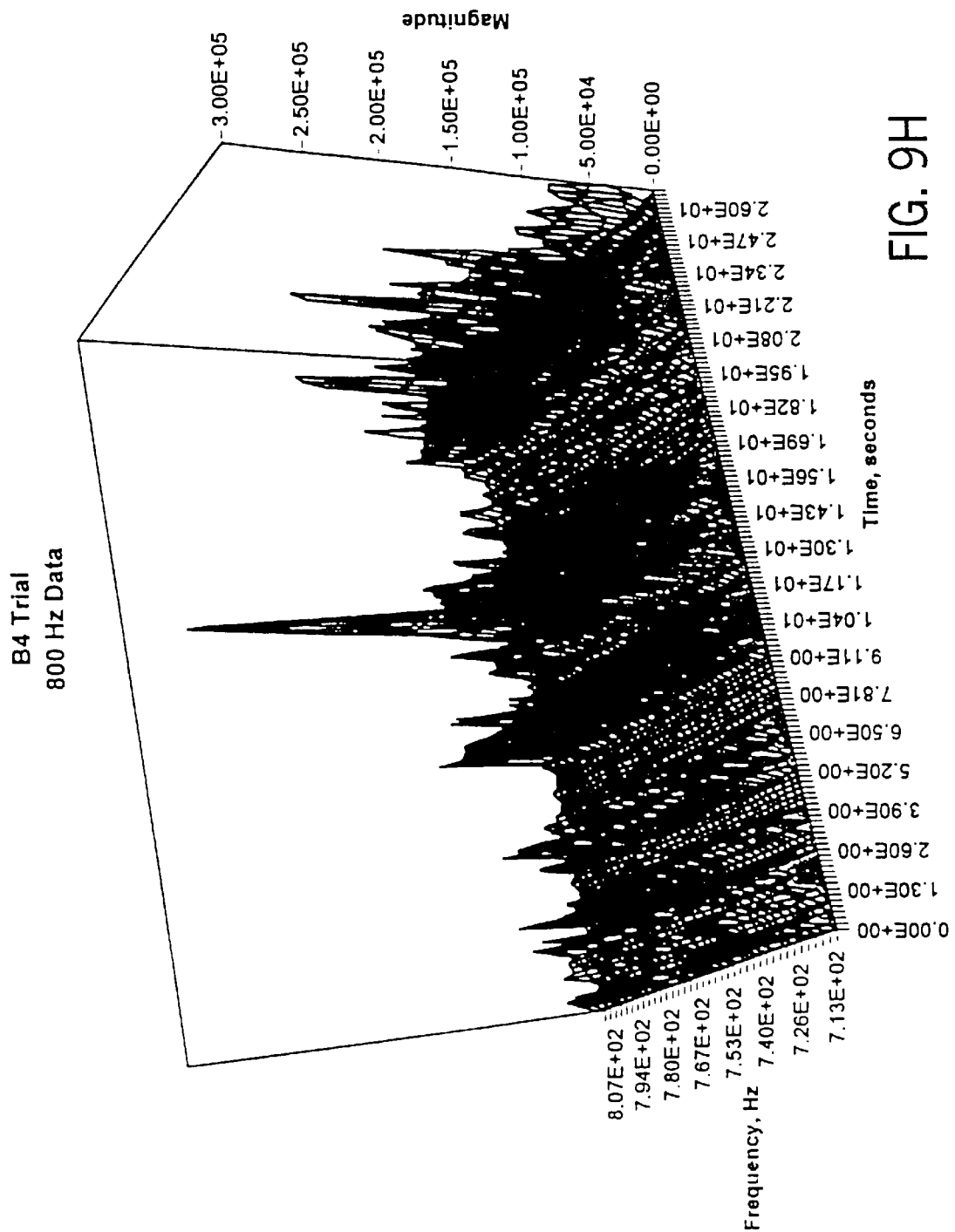
Figure 9I:
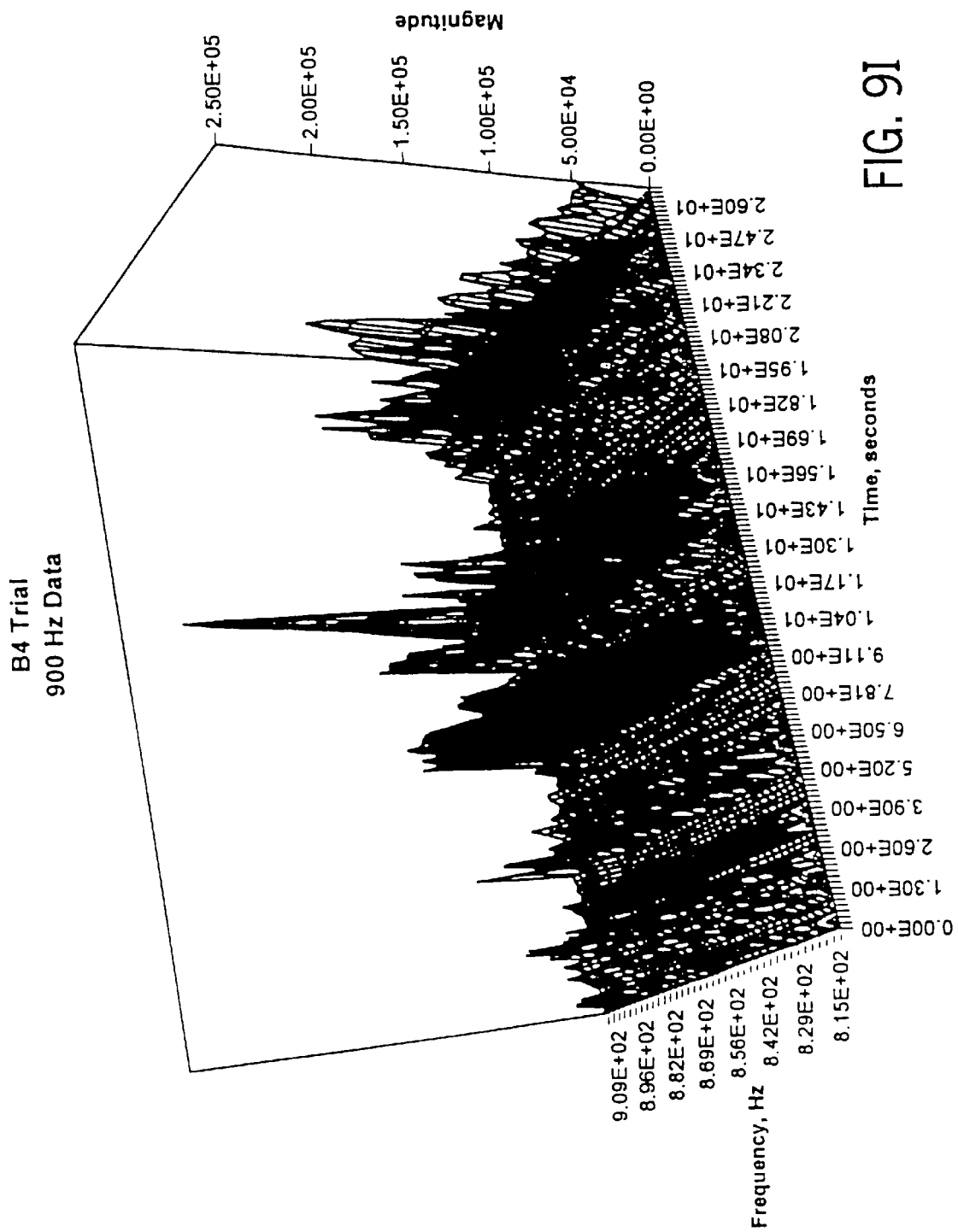
Figure 9J:
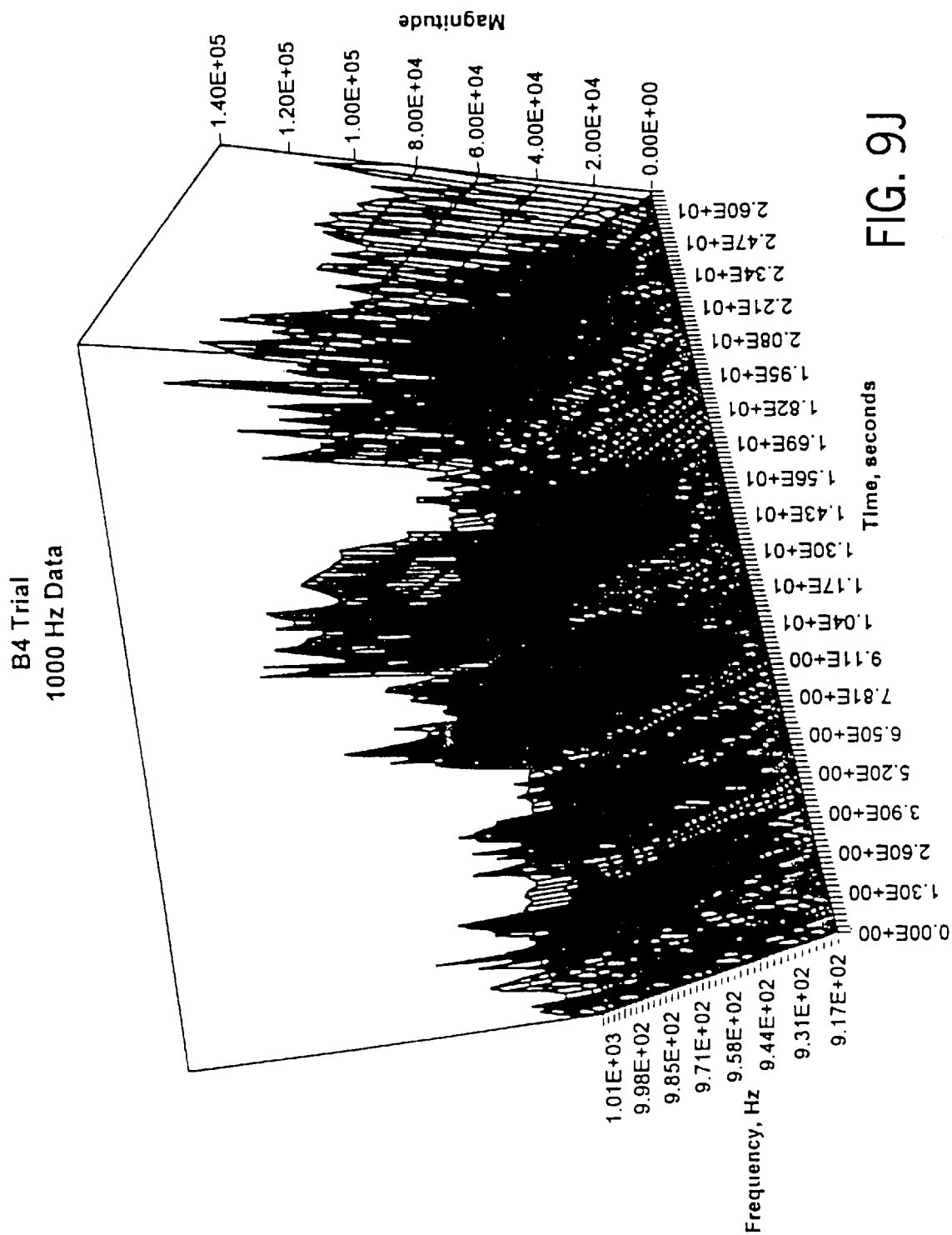
Figure 9K:
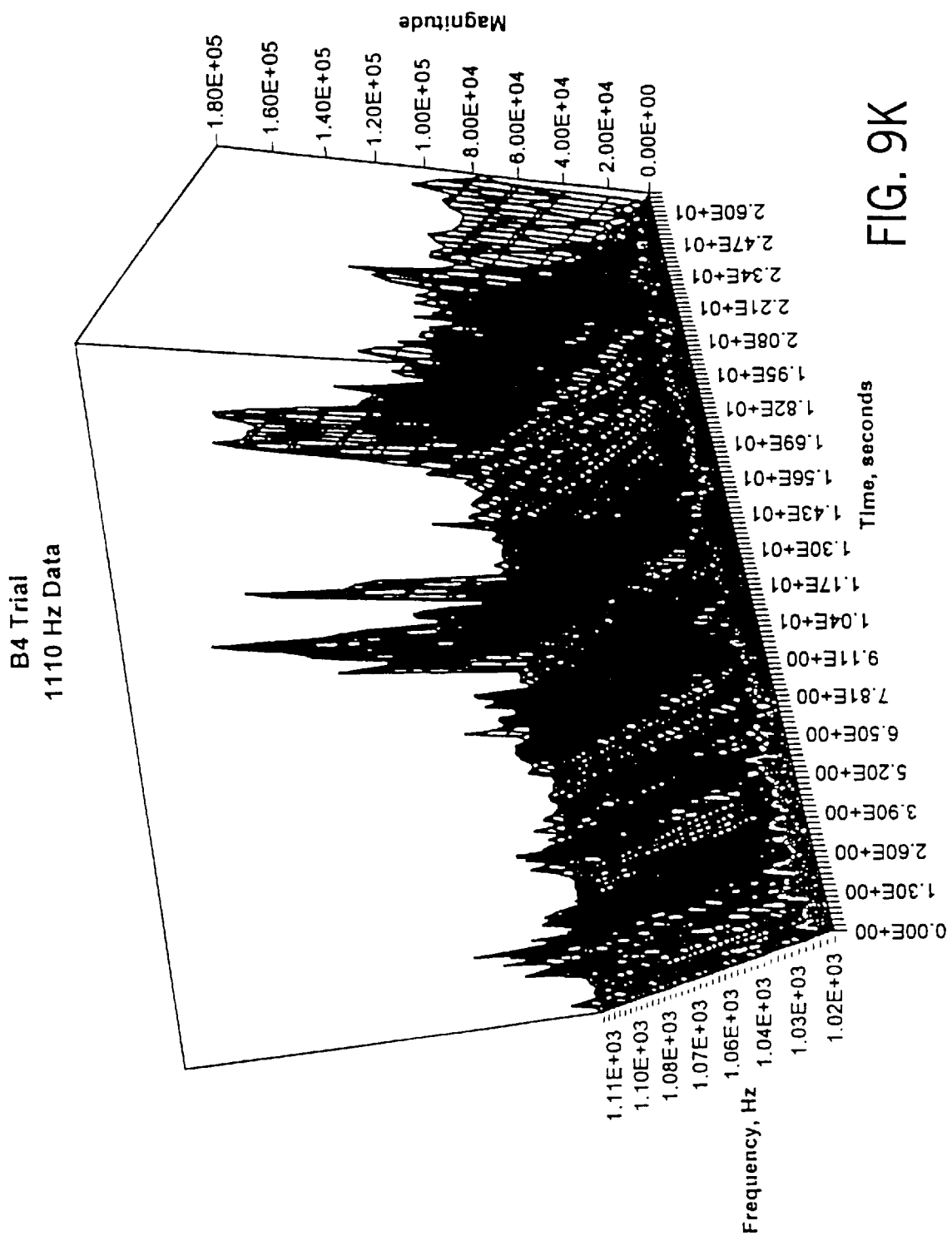
Figure 9M:
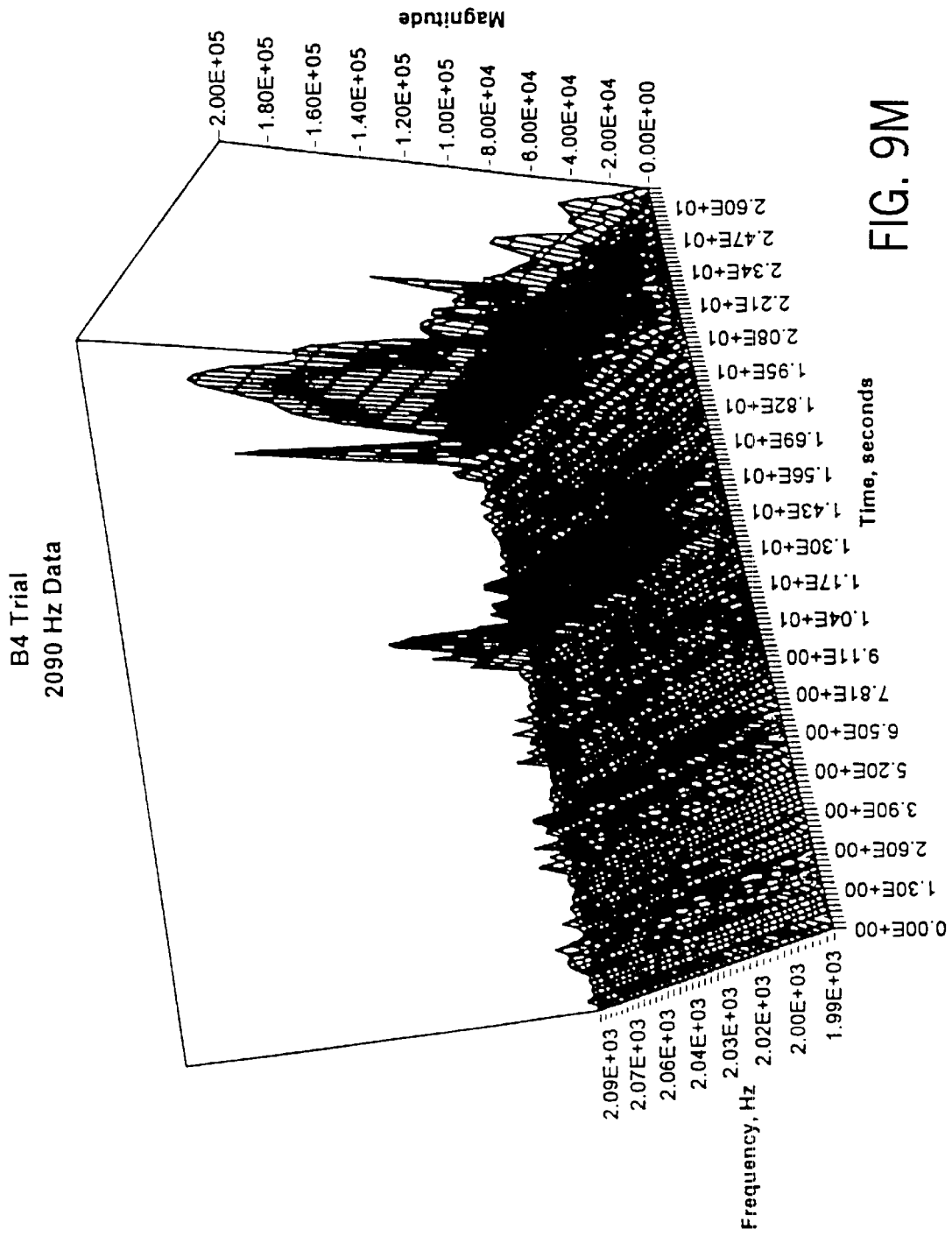
Figure 12:
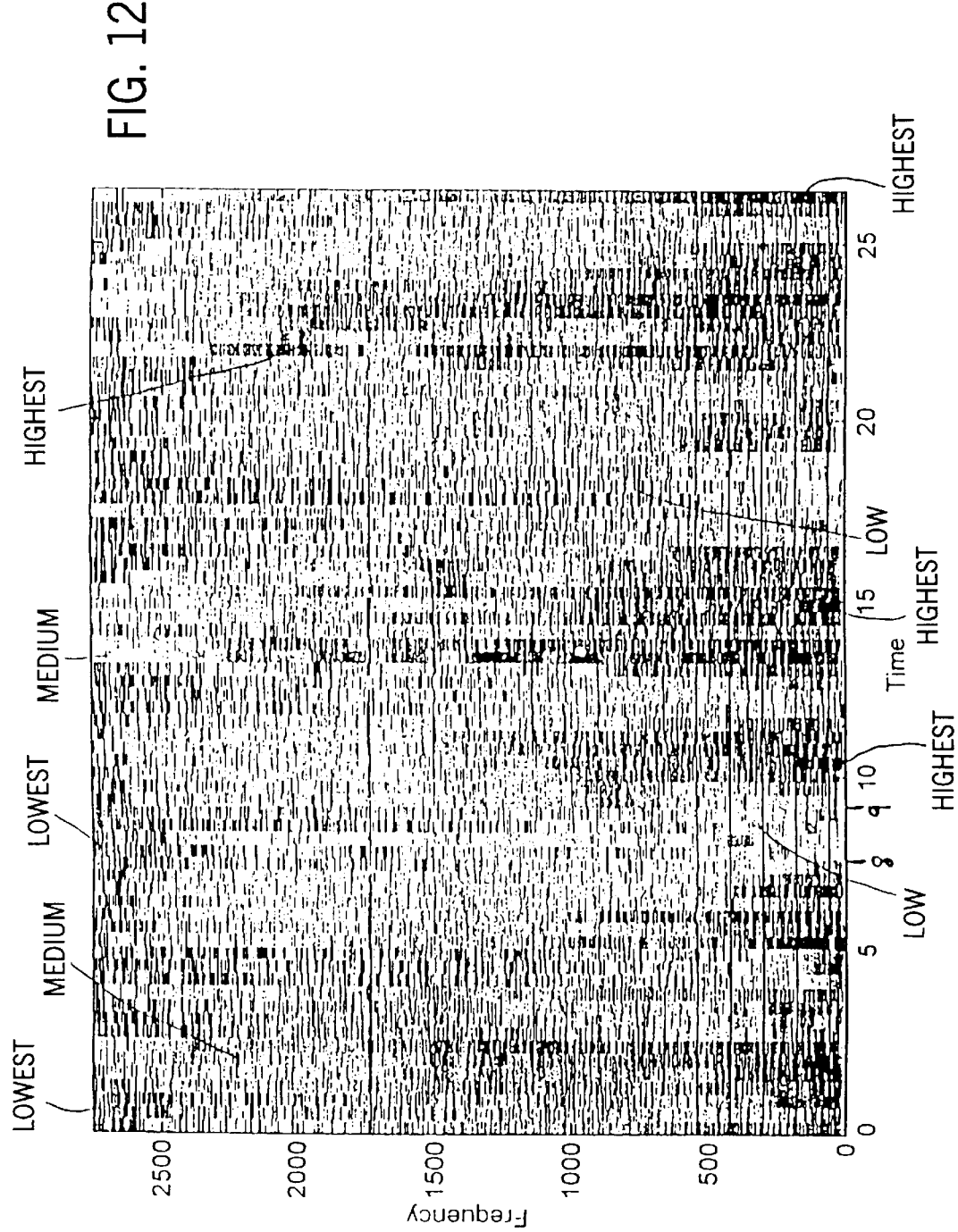
FIG. 12 shows another gray scale plot like FIG. 10 but the window increment is about 0.2 seconds with an overlap of 50%.

In FIG. 8 is a functional block flow diagram illustrating analysis of acoustic emission information by a "spectrogram" approach. In this spectrogram approach, the time record of acoustic emission signal amplitudes is taken over a user selected period of BA treatment period, which can be typically about half an hour. As shown in FIG. 6, the transducer 22 outputs the analog signals 80 to the A/D converter 82 which generates a digital spectrum for analysis. As shown in FIG. 8, this digitized time record can be sampled dynamically in real time (or afterward over the whole spectrum) in increments of, for example, 0.1 seconds (see FIG. 10) with each succeeding window increment overlapping the previous segment (except the first and last window) by, for example, 0.05 seconds. Thus, some important adjustable parameters are the length of the window and the amount of window overlap. The effect of these variables is shown in FIGS. 10–12 and described hereinafter. The time record data in each of these window increments can be Fourier transformed to yield an amplitude-versus-frequency segment. That is, the result is a vector whose elements are Fourier transform magnitudes at various frequencies. These can all be assembled dynamically in substantially real time, or after treatment, to generate a three-dimensional plot of amplitudes at a given time versus frequency. These data can then be displayed in frequency segments and evaluated for characteristic information. As shown in FIGS. 9A–9N, which cover a 0–27 second time period, there are dramatic features of the time frequency spectrogram which can be correlated to various events occurring during BA treatment (or have occurred if analyzing data accumulated in the past). For example, as can be noted in FIGS. 9A and 9B, there are strong frequency components at the end of the BA experimental data set, and these are believed to arise from vascular tissue dissection. It would thus be very useful to identify frequency peaks indicative of the onset of vascular tissue dissection. This information would allow termination of the BA treatment before serious injury to vascular tissue and improve prognosis for a healthy recovery by the patient. With this in mind (and without limiting the invention), note, for example, the large frequency amplitude features at about twenty-two to twenty-four seconds in FIG. 9M (2000 Hz) and FIG. 9N (2330 Hz). Further experimentation ex vivo will easily establish clear correlation of spectral events with certain analytical spectra shown herein and thus will enable control of BA treatment.

The data of FIG. 9A–9N can also be displayed in a color coded or gray scale manner to provide the information in a more easily understandable manner. In FIG. 10 is shown the form of the data in FIGS. 9A–9N for window increments of about 0.1 s (and a 50% window overlap) in the time record of acoustic emission signals. The frequency amplitude is denoted by a particular gray scale, with the darkest areas (labeled "highest") having the largest amplitudes; the next level, labeled "medium," being intermediate in amplitude; the next lowest, labeled "low"; and the lightest areas of lowest magnitude next being labeled the "lowest". As can be noted, the selected time segment for the window has a substantial influence on resolution and on the impression given to the observer. It should be noted also that color coding is preferred and generally more easy for the clinician to evaluate. Such a method of data display also highlights the presence of systematic noise, like the 60 Hz noise (and its multiples) arising from use of an unshielded cable used between the transducer 22 collecting the acoustic emission data and the external instrumentation 58 (see FIG. 1A). Such information enables easy removal of such noise.

Other examples of gray scale coded frequency amplitudes plots like FIG. 10 are shown in FIGS. 11 and 12. The frequency data for FIG. 11 was obtained using a 0.1 second window with a 25% window overlap and FIG. 12 had a 0.2 second window with 50% window overlap for sampling the time record of acoustic emission signals. Note the effect of variable window length and degree of overlap.

In a next step, shown in FIG. 8, of evaluating the acoustic emission data, a pattern recognition methodology is implemented. In this method, the window increments of data are each input as a separate data set in time order. This can be dynamic real time as data is accumulated, or afterward, with the user selecting the desired data segment. Each of these window increments of data are thus processed by a pattern recognition formalism, such as a Kohonen classification neural network, or other such well known probabilistic network. In demonstrating the use of such a network a NeuroShell2 computer program was used. This program is available from Ward Systems Group, Inc. Frederick, Md. A particular example of its application is described in Example III.

In order to implement the neural network, each of the user selected increments of time ordered data are input to all of the nodes of the neural network and correlations are determined based on training data input. The training data correlations have already established known data correlation for use in interpreting correlations in a data set to be analyzed.

Such training can involve direct experimental correlation, such as identifying the early stages of vascular rupture and isolating the accompanying acoustic emission data associated therewith (time, frequency, etc.). Consequently, in the illustrated network of FIG. 8, the Kohonen network uses unsupervised learning of the input, uncharacterized data to determine the frequency distribution of the input patterns and then identify the category to which an unknown pattern belongs. In such Kohonen networks, important adjustable parameters are, for example, the number of categories and terms which control the training of the network. For example, note the various categories in FIG. 8, such as no observable activity, fracture of plaque, prerupture of vascular tissue and rupture of vascular tissue. As noted above, Example m illustrates application of the neural network analysis.

Figure 13A:
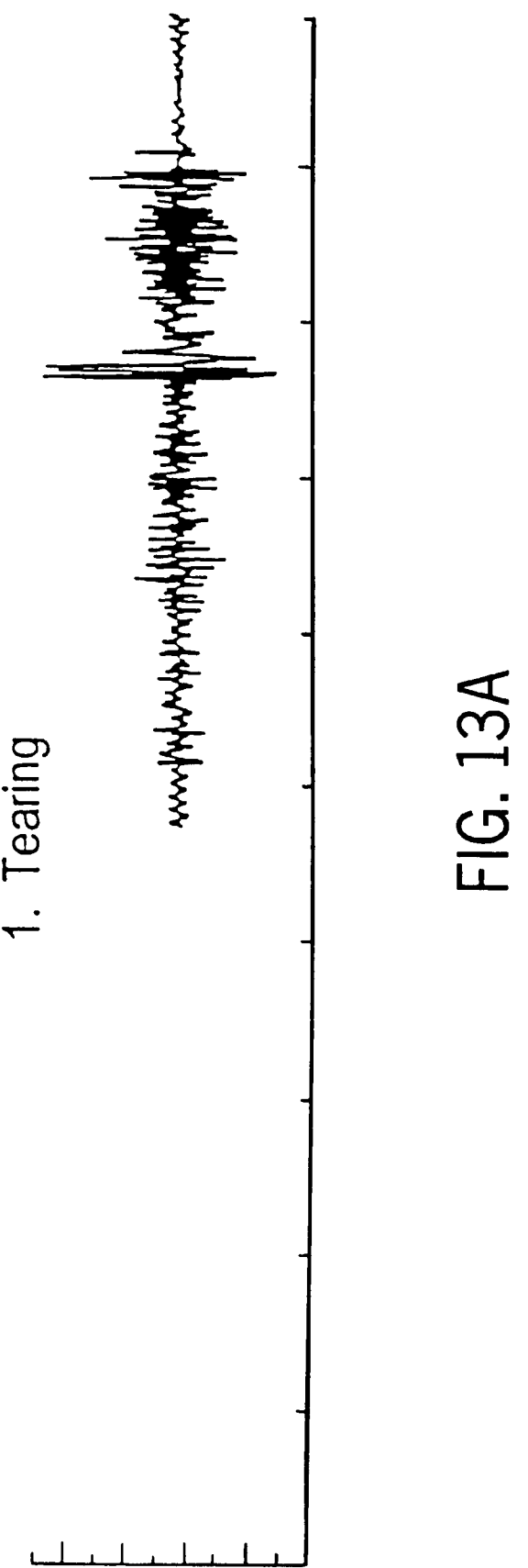
FIG. 13A illustrates a time segment taken from the full BA treatment time period.
Figure 13B:
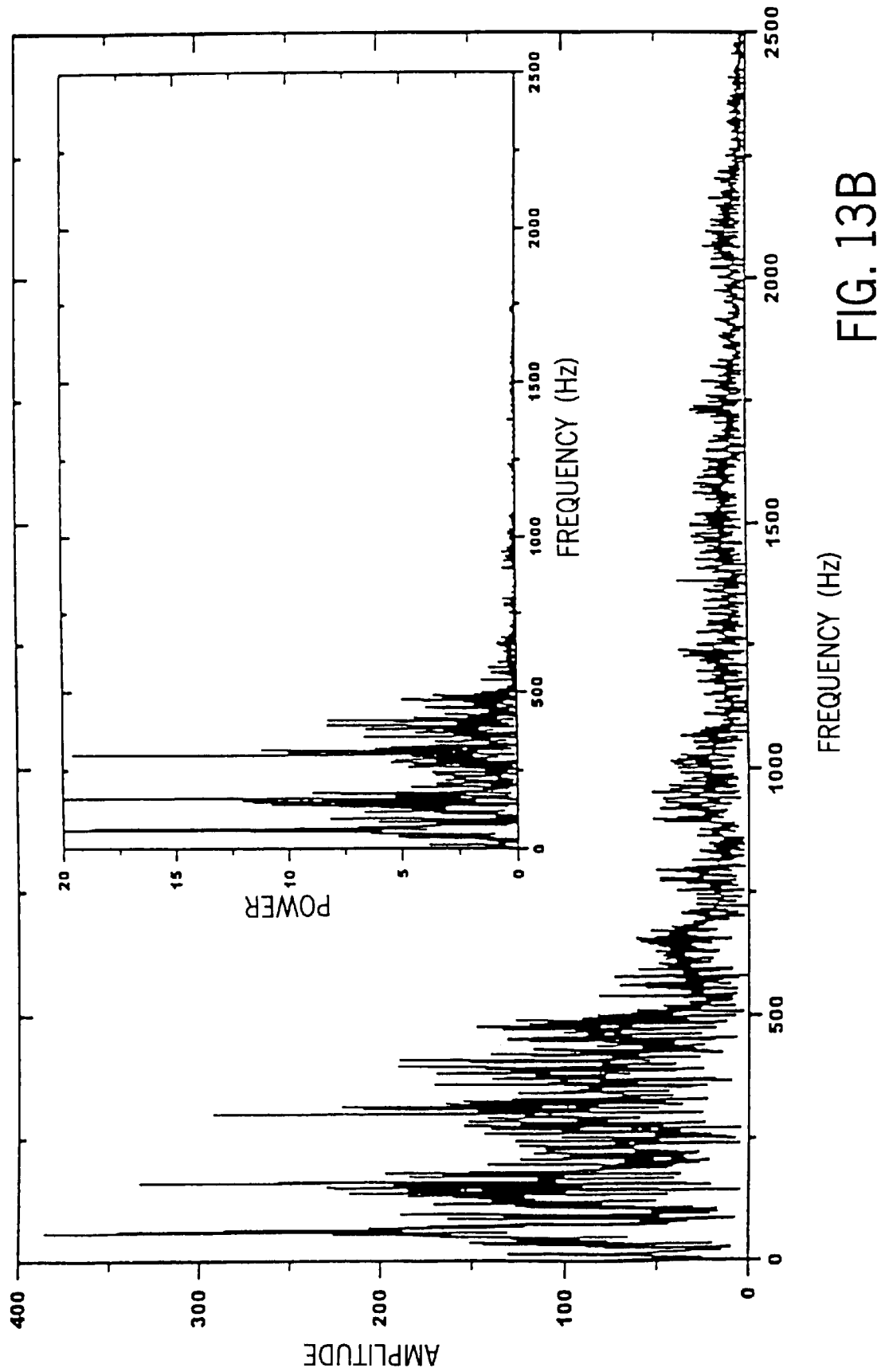
FIG. 13B illustrates a Fourier transform of the data of FIG. 13A and a power spectrum is also shown.
Figure 14B:
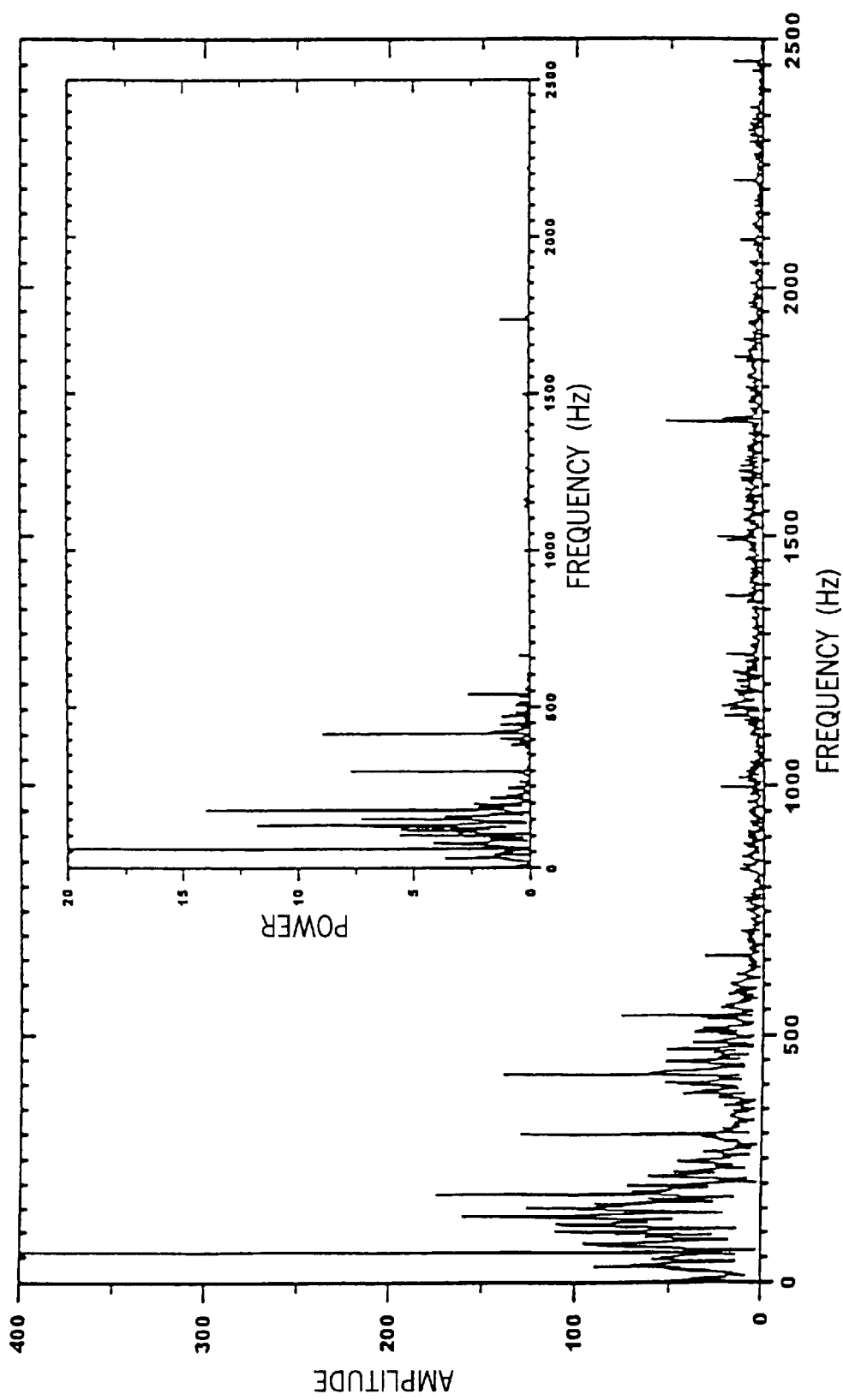
FIG. 14B illustrates a Fourier transform of the data of FIG. 14A and a power spectrum is also shown.
Figure 15A:
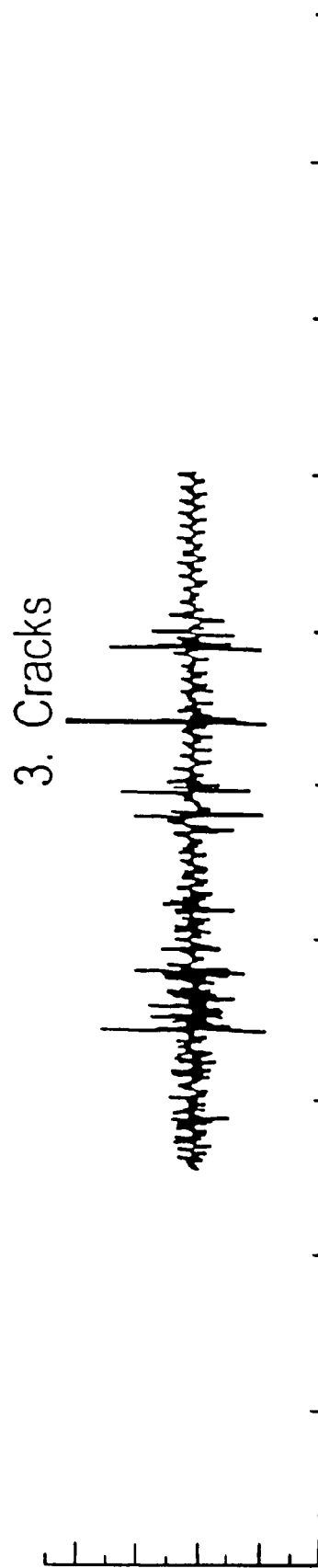
FIG. 15A illustrates a time segment taken from the full BA treatment time period.
Figure 15B:
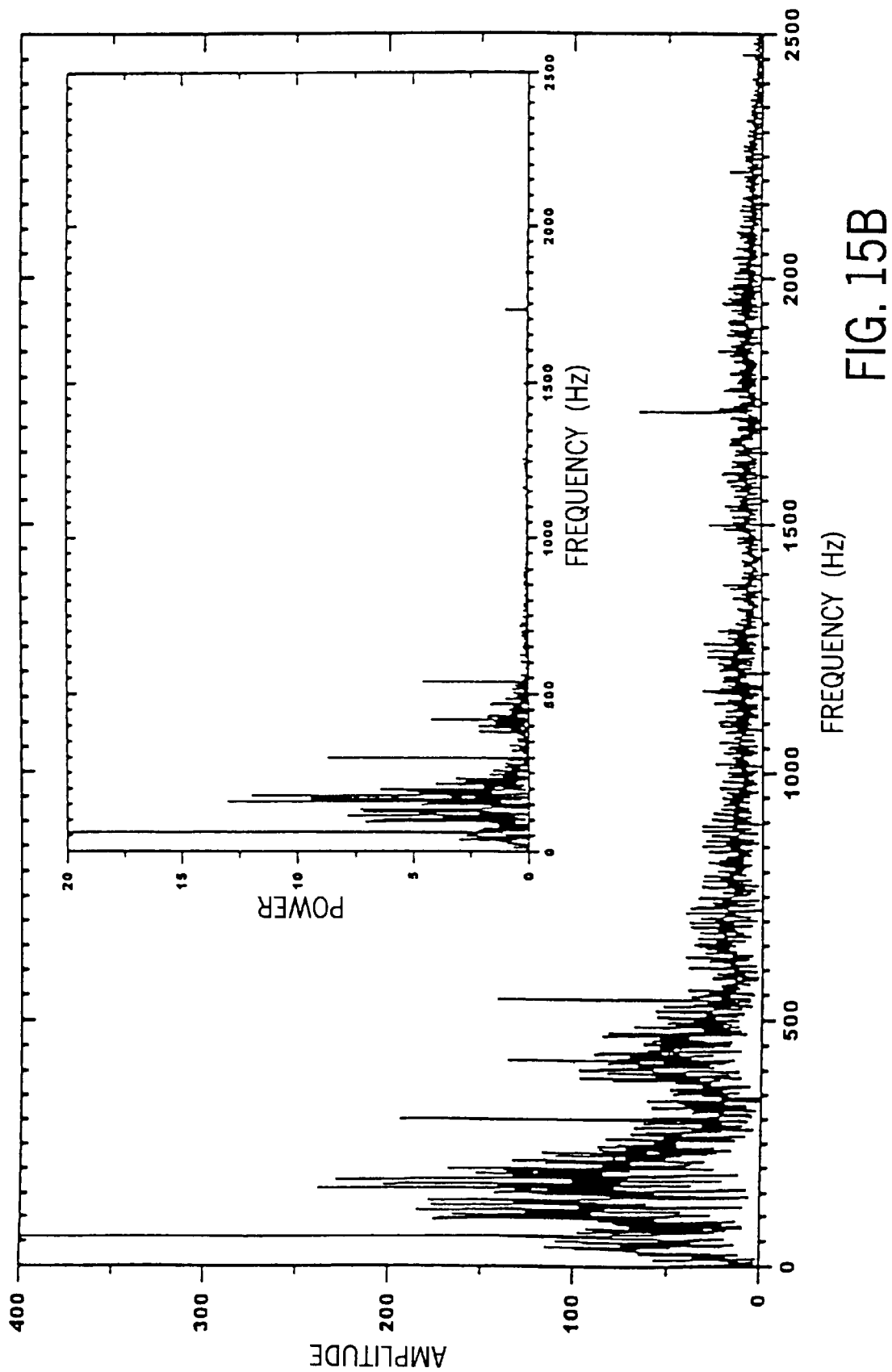
FIG. 15B illustrates a Fourier transform of the data of FIG. 15A and a power spectrum is also shown.
Figure 16A:
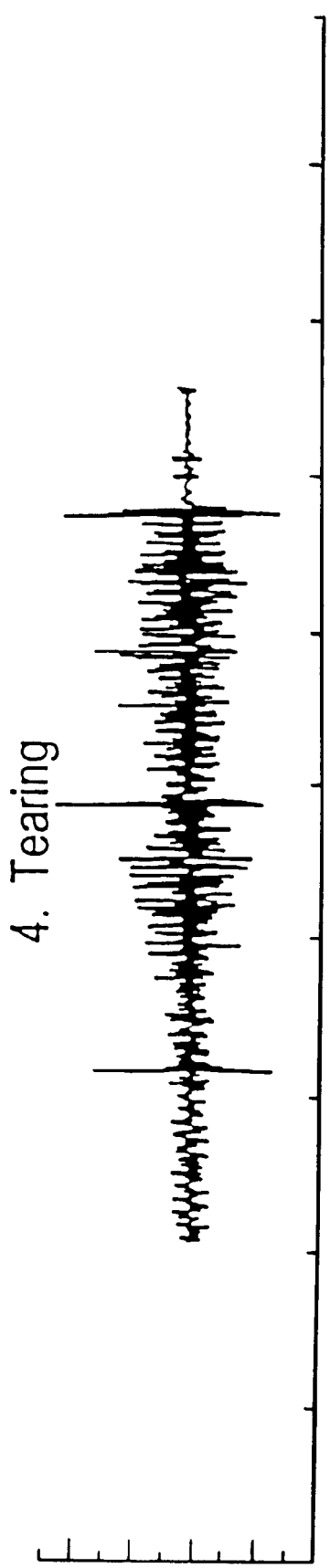
FIG. 16A illustrates a time segment taken from the full BA treatment time period.
Figure 16B:
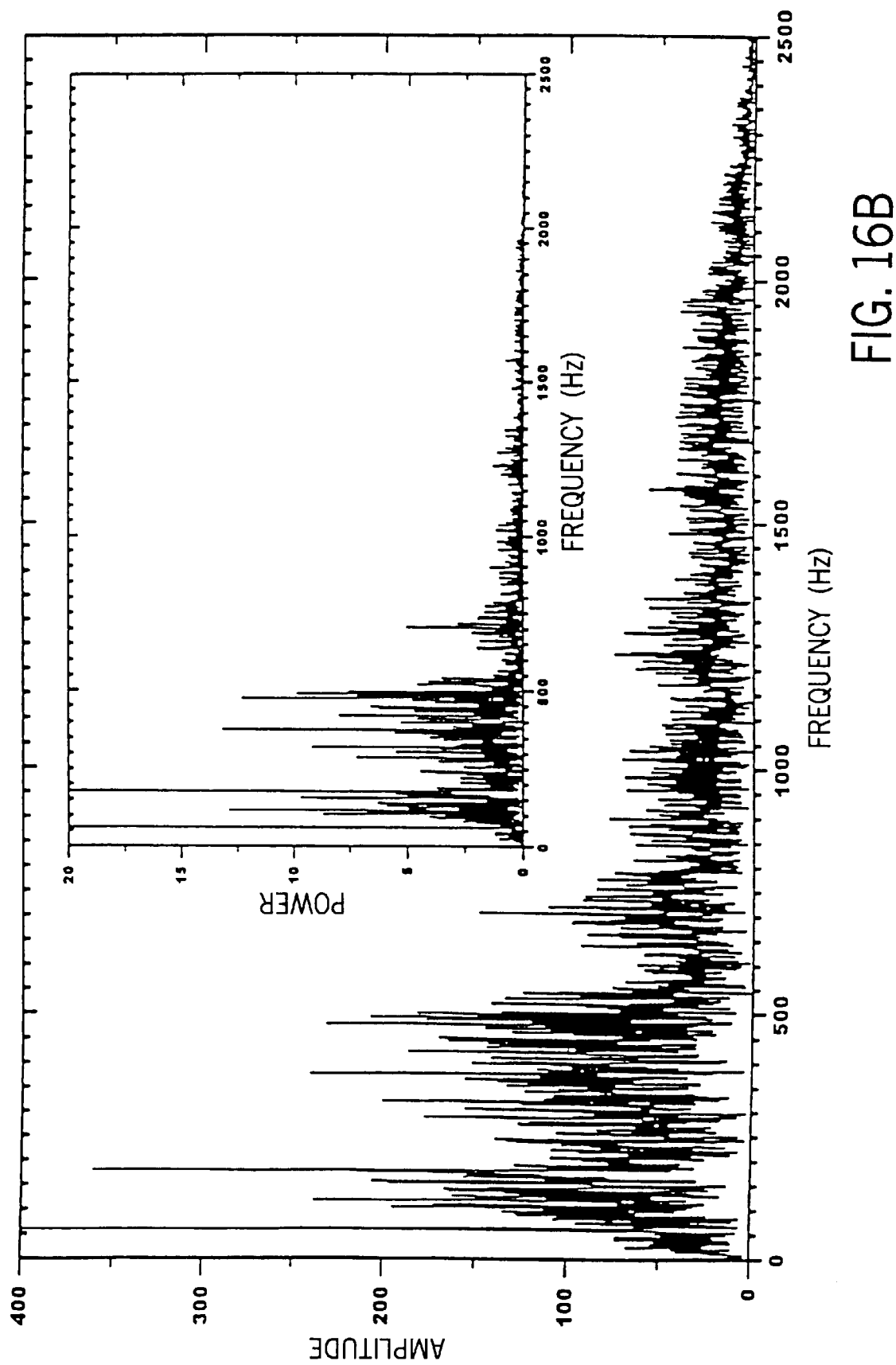
FIG. 16B illustrates a Fourier transform of the data of FIG. 16A and a power spectrum is also shown.
Figure 17B:
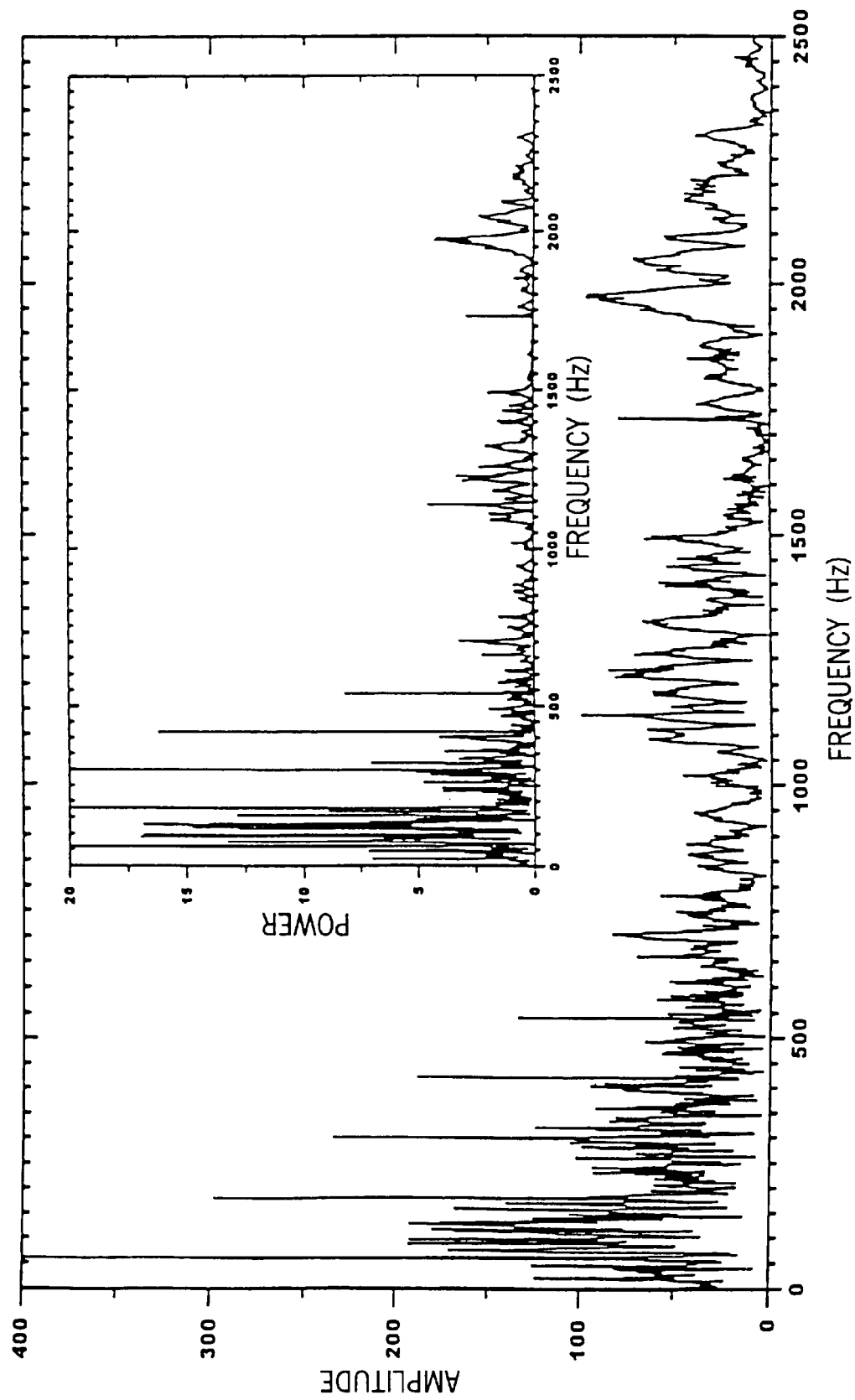
FIG. 17B illustrates a Fourier transform of the data of FIG. 17A and a power spectrum is also shown.
Figure 18A:
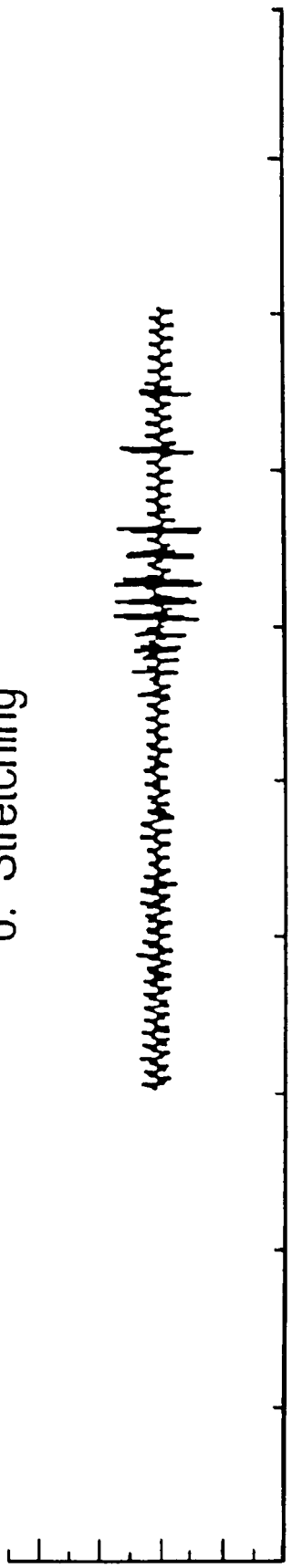
FIG. 18A illustrates a time segment taken from the full BA treatment time period.
Figure 18B:
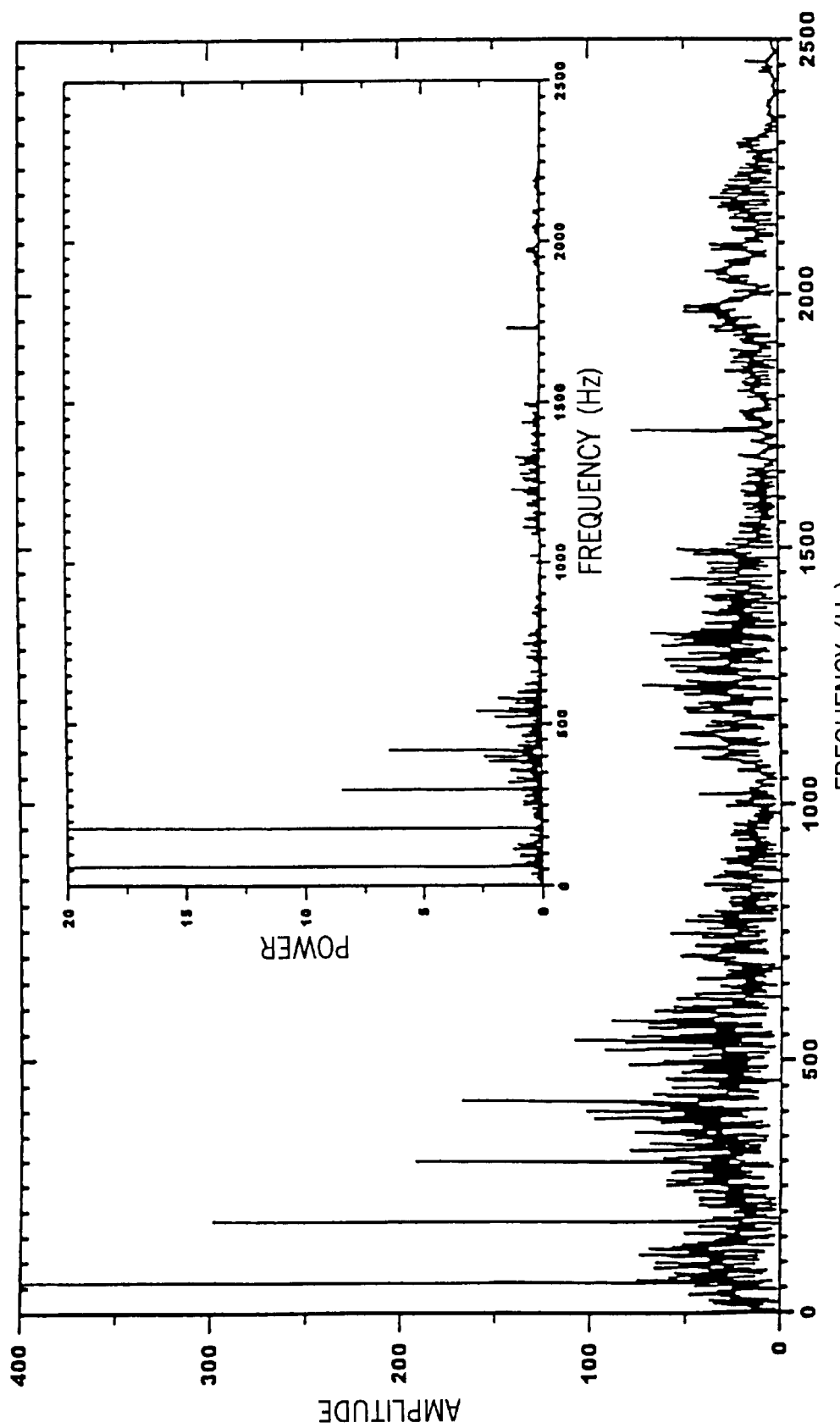
FIG. 18B illustrates a Fourier transform of the data of FIG. 18A and a power spectrum is also shown.
Figure 19A:
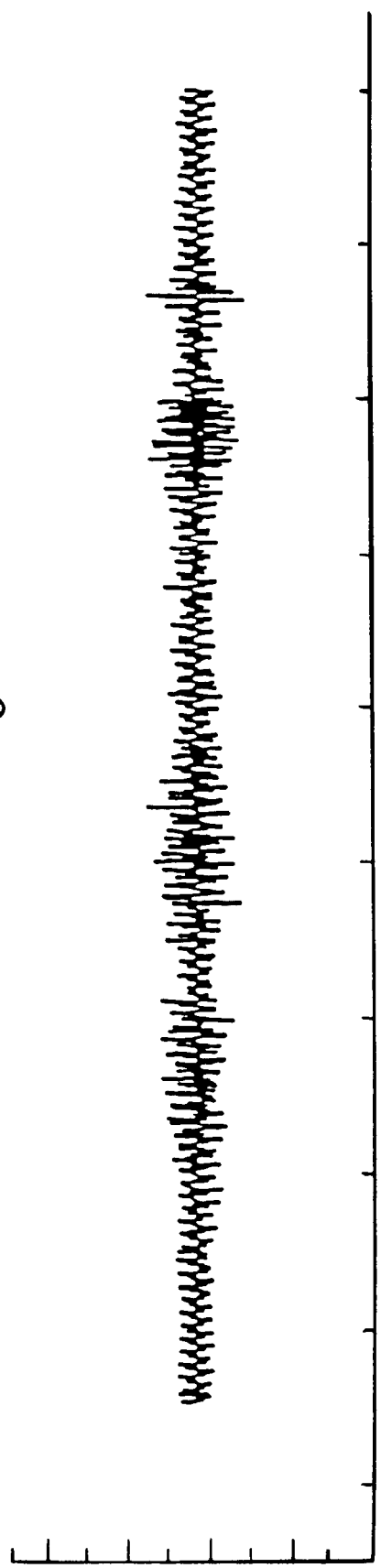
FIG. 19A illustrates a time segment taken from the full BA treatment time period.
Figure 19B:
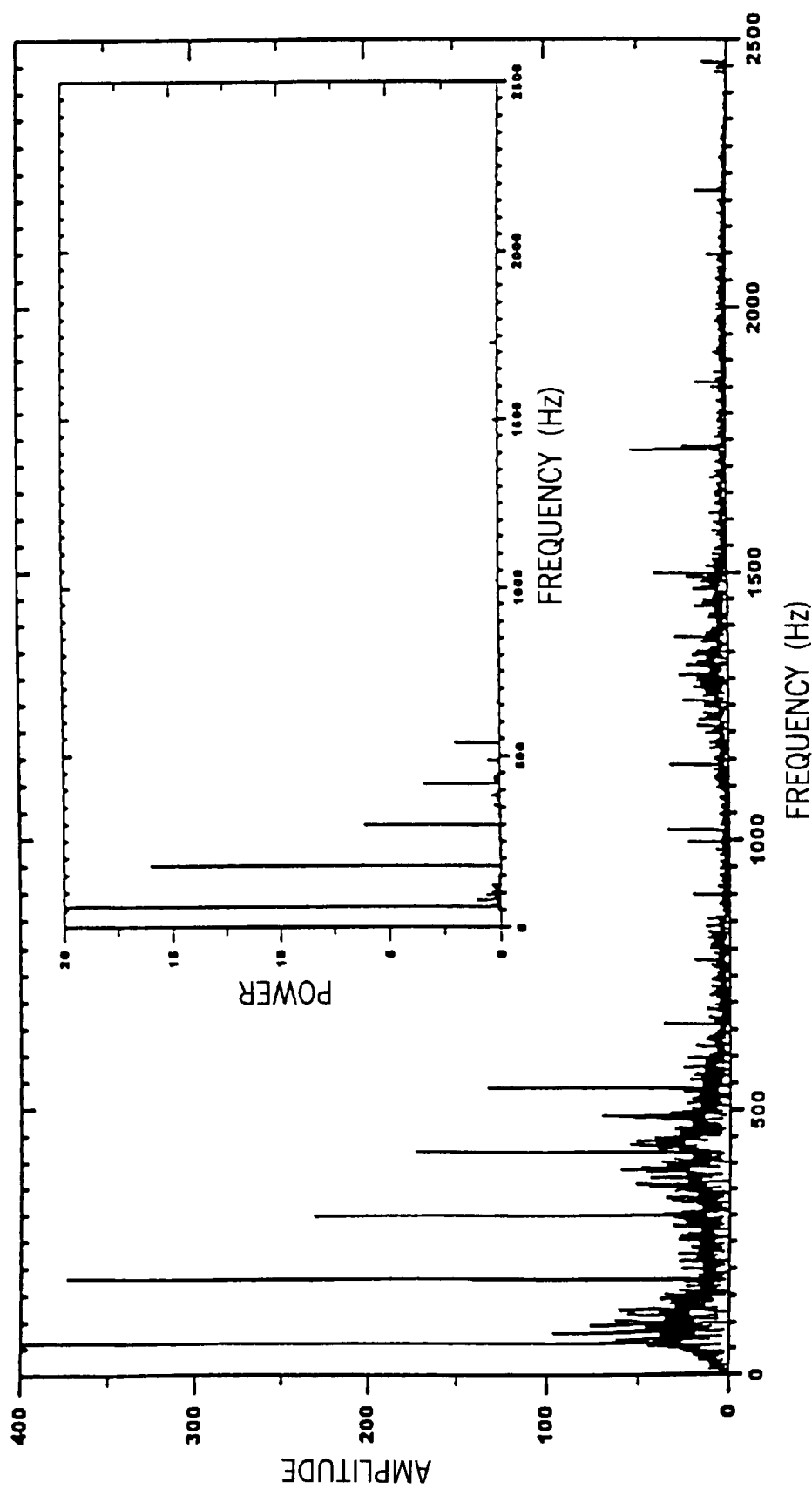
FIG. 19B illustrates a Fourier transform of the data of FIG. 19A and a power spectrum is also shown.
Figure 20A:
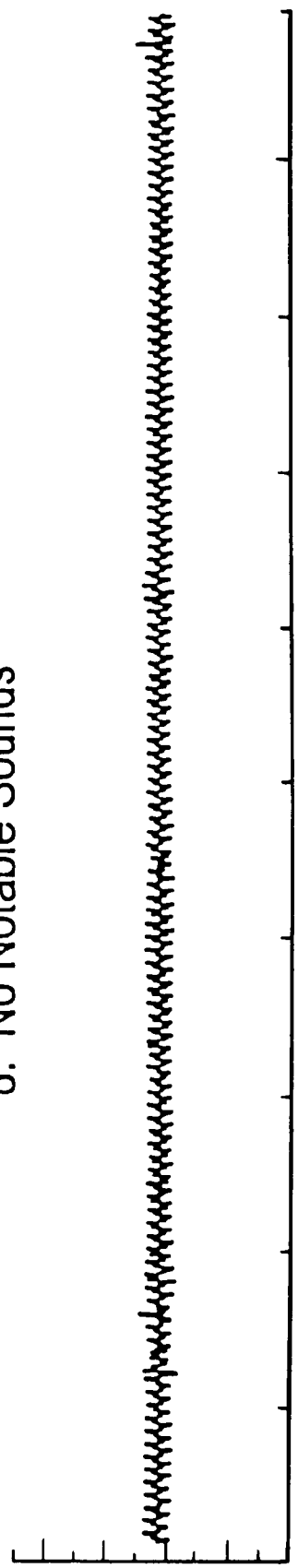
FIG. 20A illustrates a time segment taken from the full BA treatment time period.
Figure 20B:
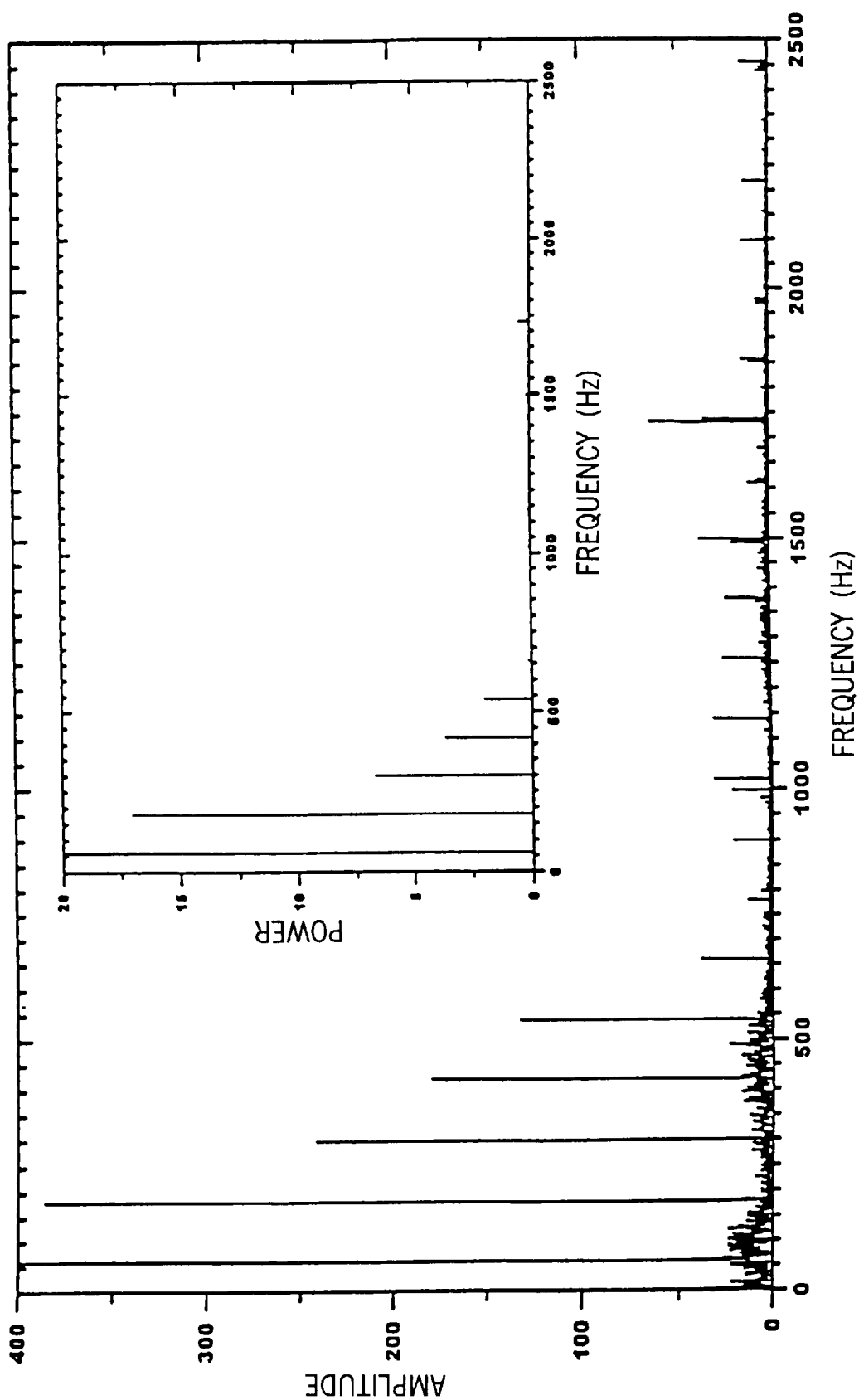
FIG. 20B illustrates a Fourier transform of the data of FIG. 20A and a power spectrum is also shown.
Figure 21A:
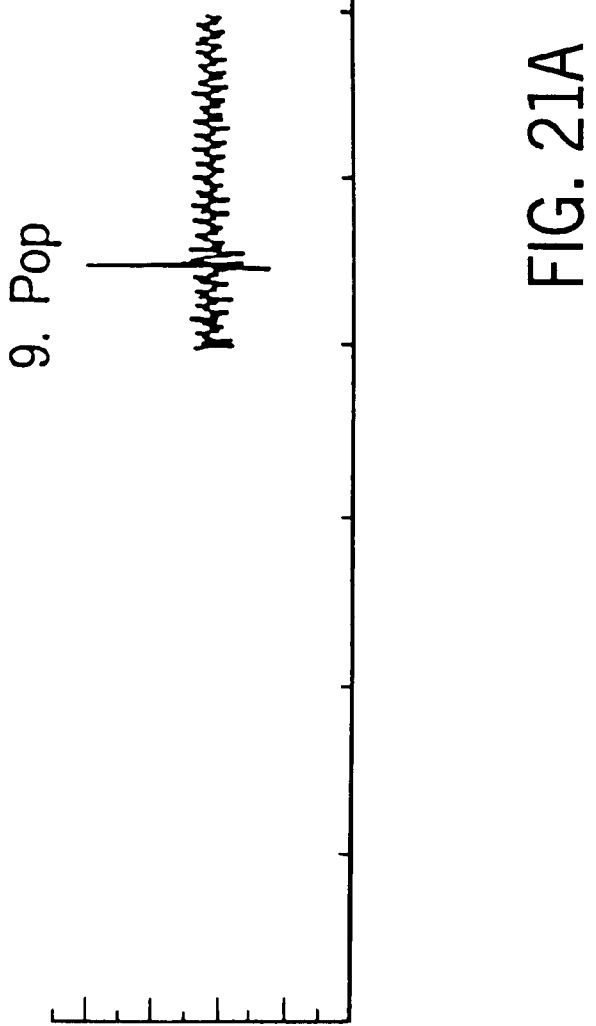
FIG. 21A illustrates a time segment taken from the full BA treatment time period.
Figure 21B:
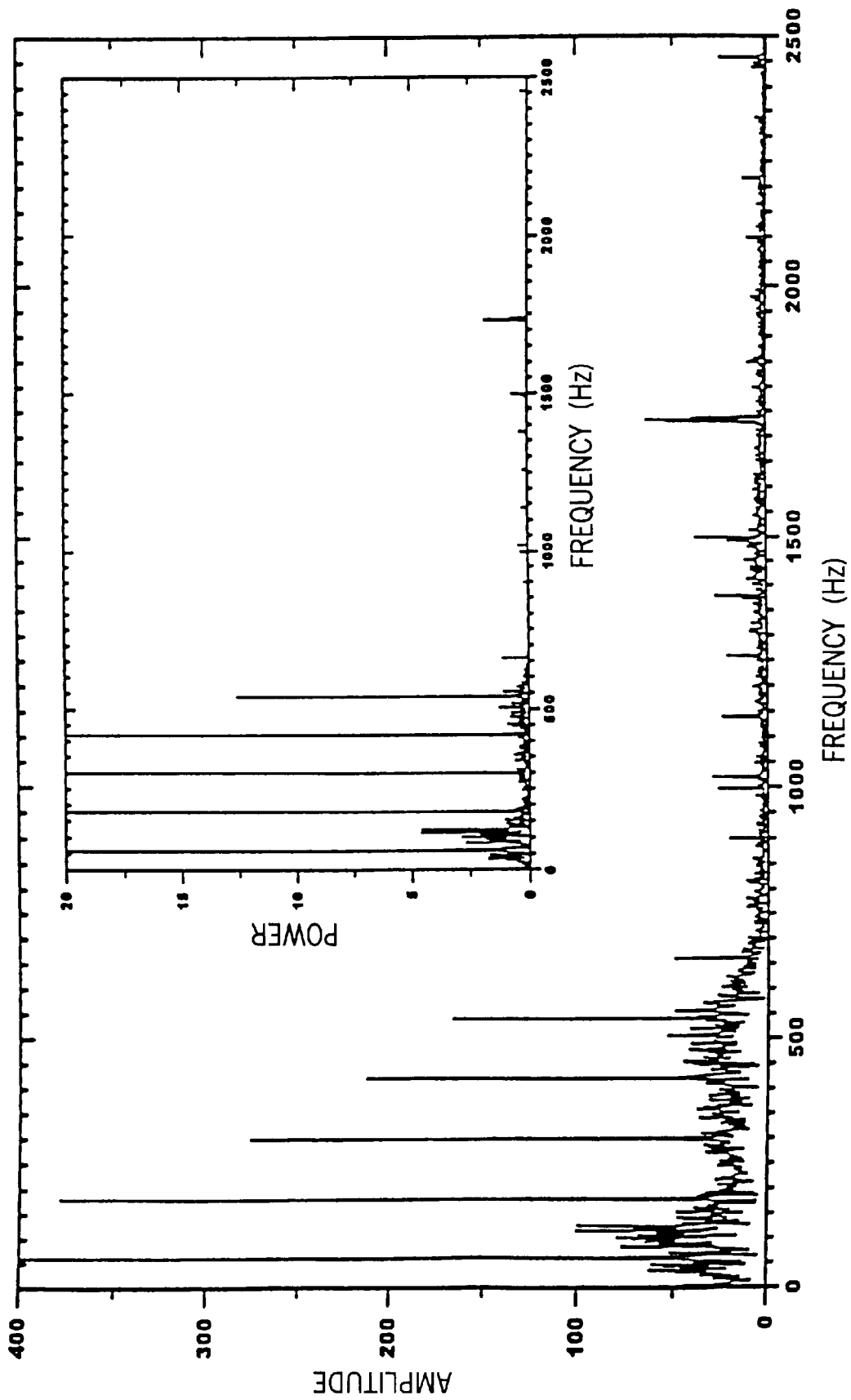
FIG. 21B illustrates a Fourier transform of the data of FIG. 21A and a power spectrum is also shown.
Figure 22A:
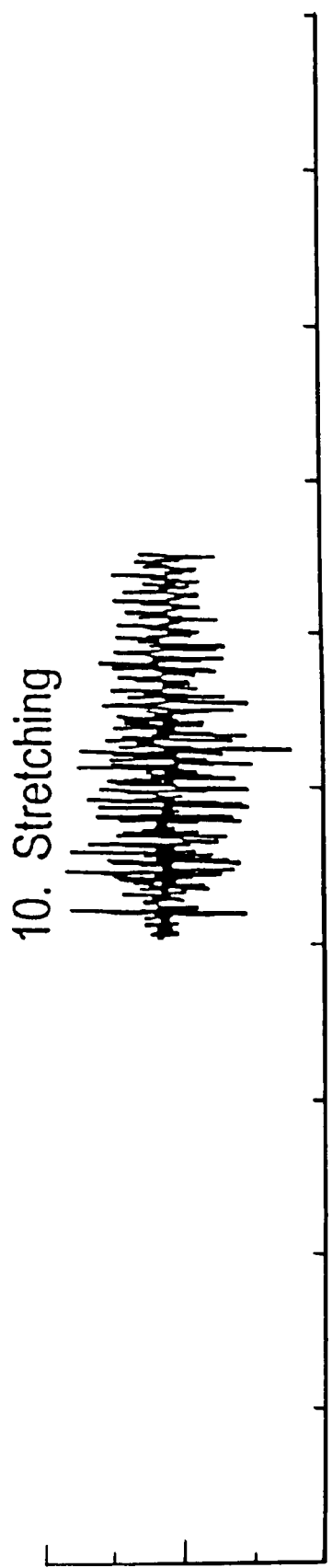
FIG. 22A illustrates a time segment taken from the full BA treatment time period.
Figure 22B:
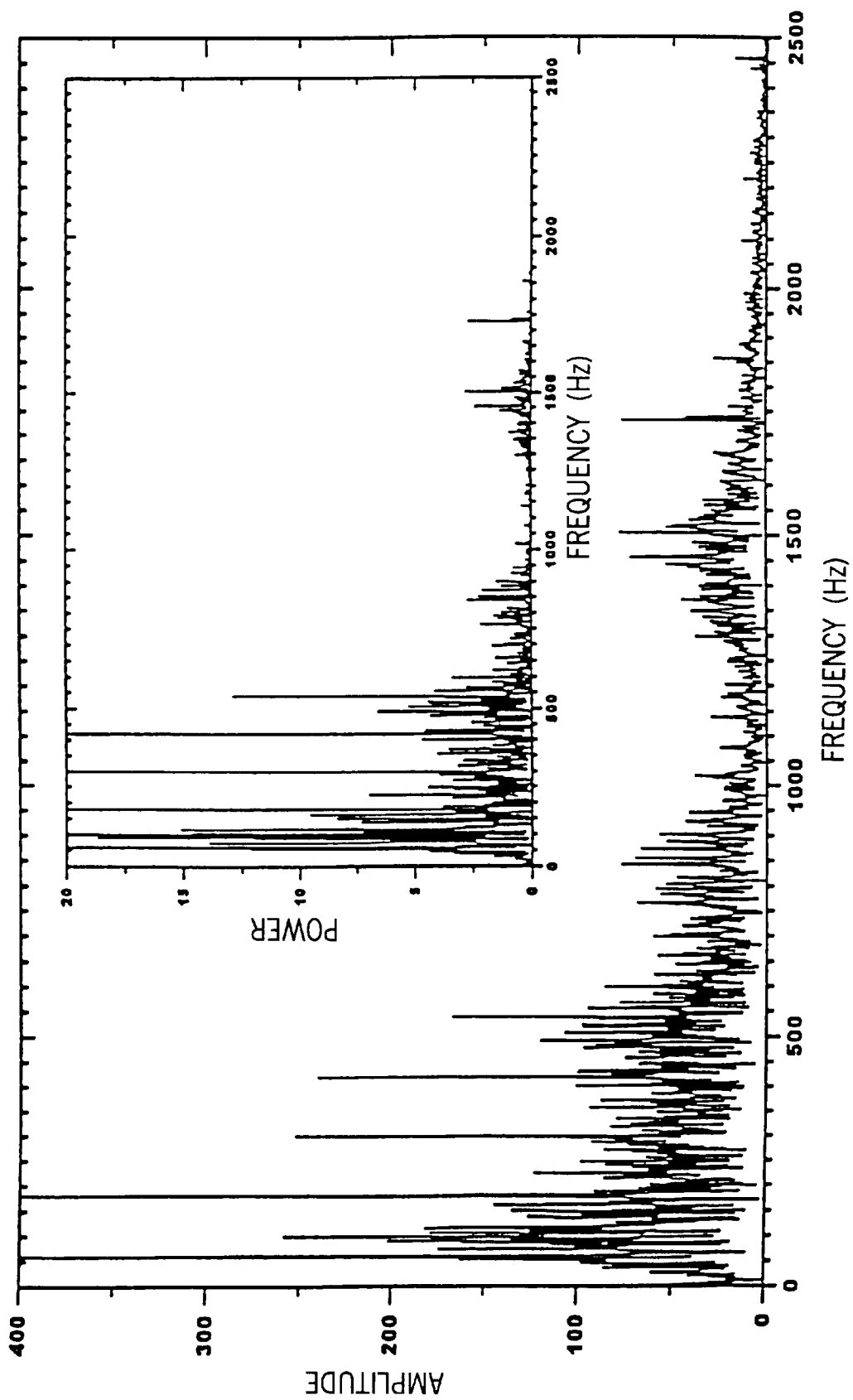
FIG. 22B illustrates a Fourier transform of the data of FIG. 22A and a power spectrum is also shown.
Figure 23A:
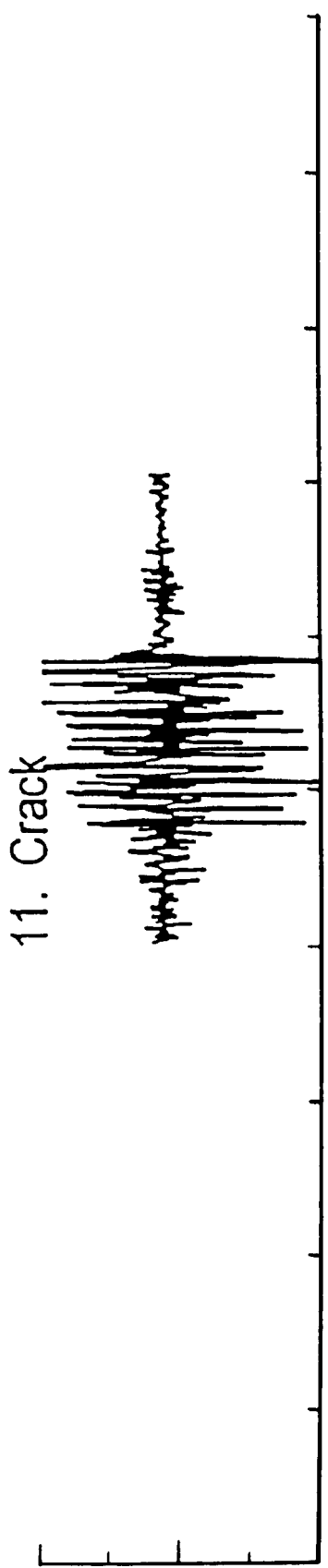
FIG. 23A illustrates a time segment taken from the full BA treatment time period.
Figure 23B:
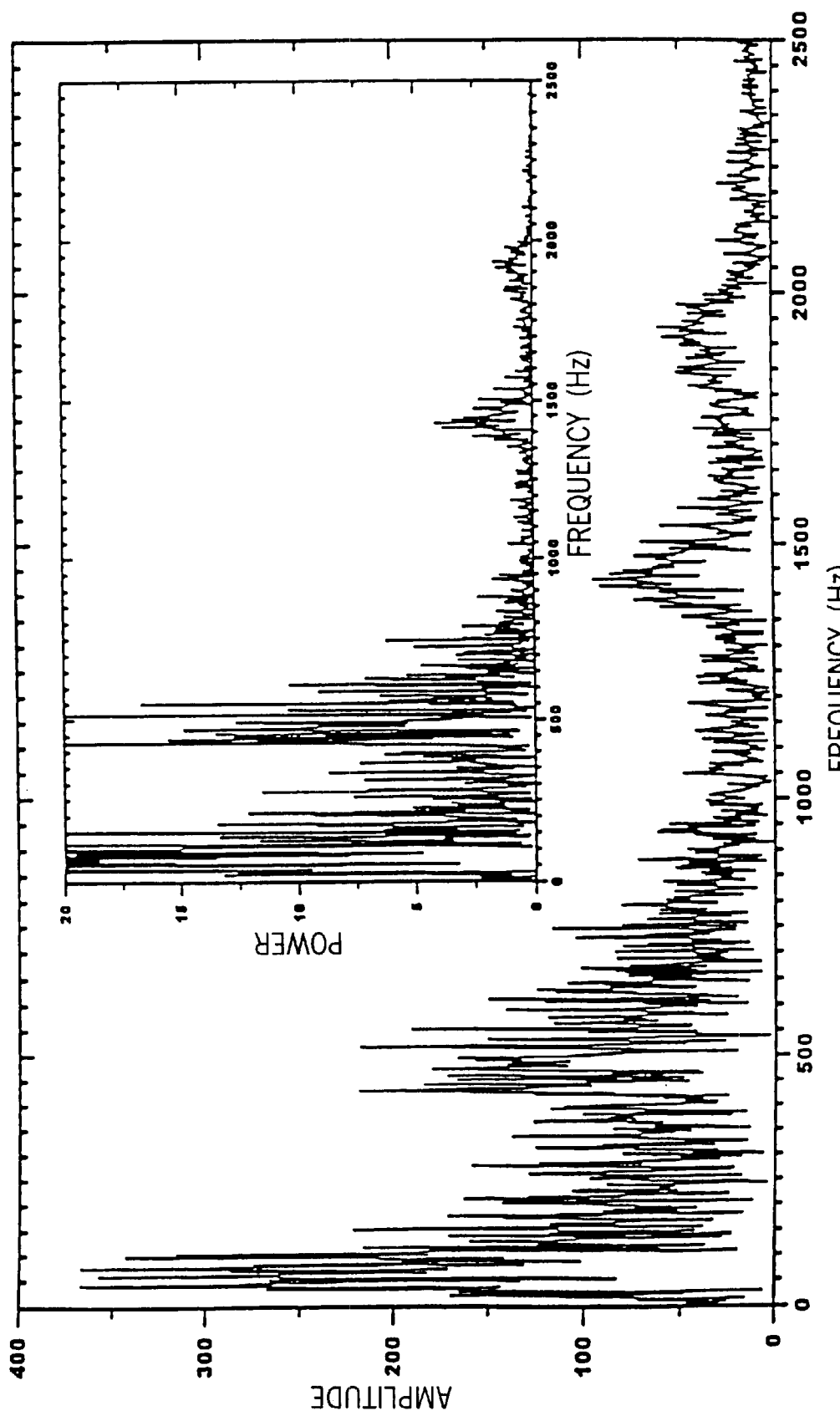
FIG. 23B illustrates a Fourier transform of the data of FIG. 23A and a power of the spectrum is also shown.
Figure 24A:
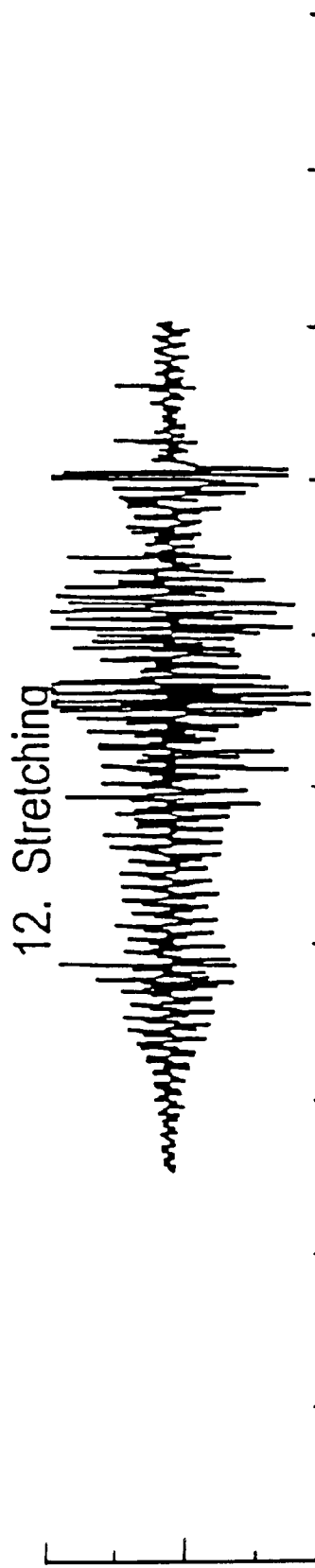
FIG. 24A illustrates a time segment taken from the full BA treatment time period.
Figure 24B:
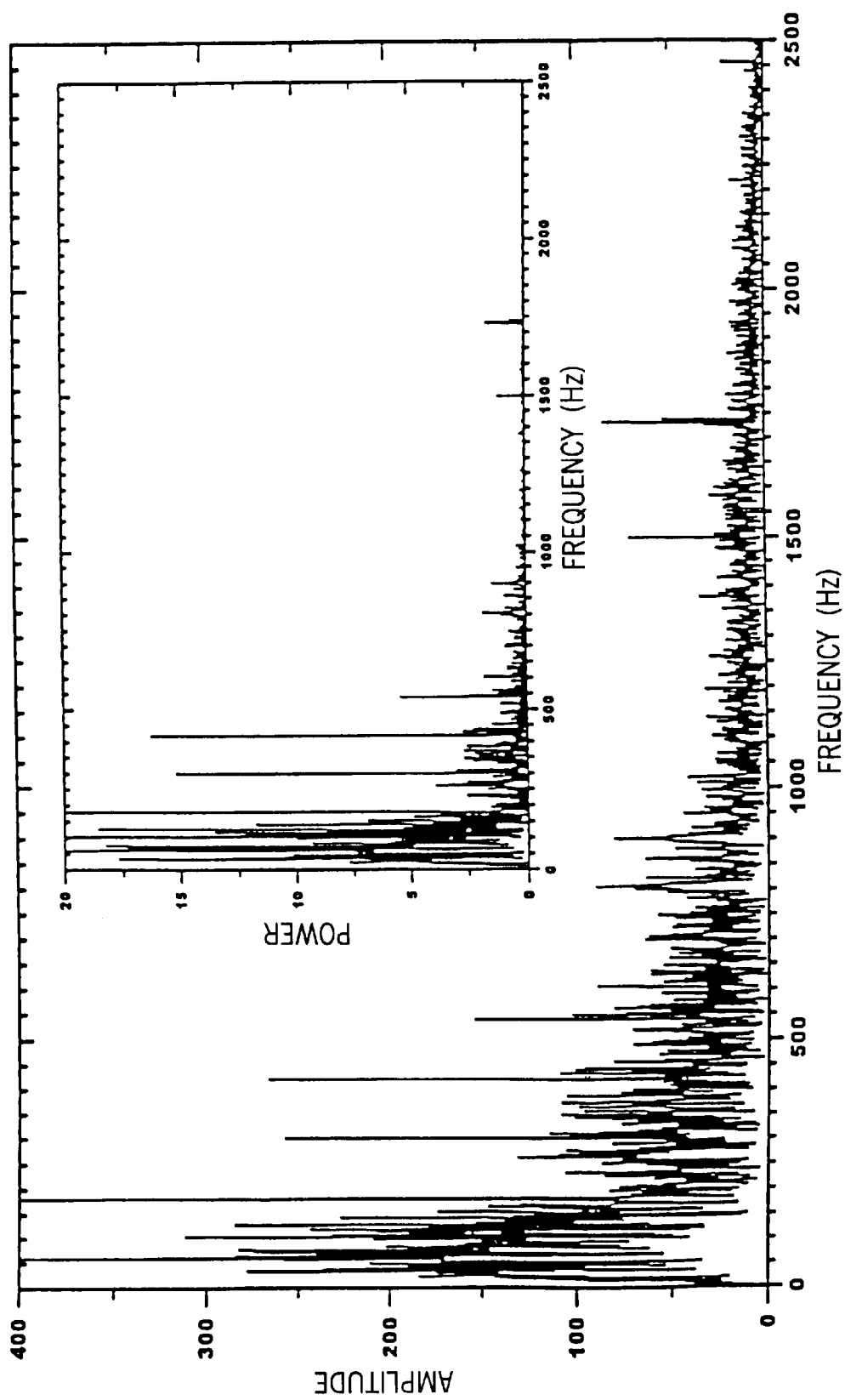
FIG. 24B illustrates a Fourier transform of the data of FIG. 24A and a power spectrum is also shown.
Figure 25A:
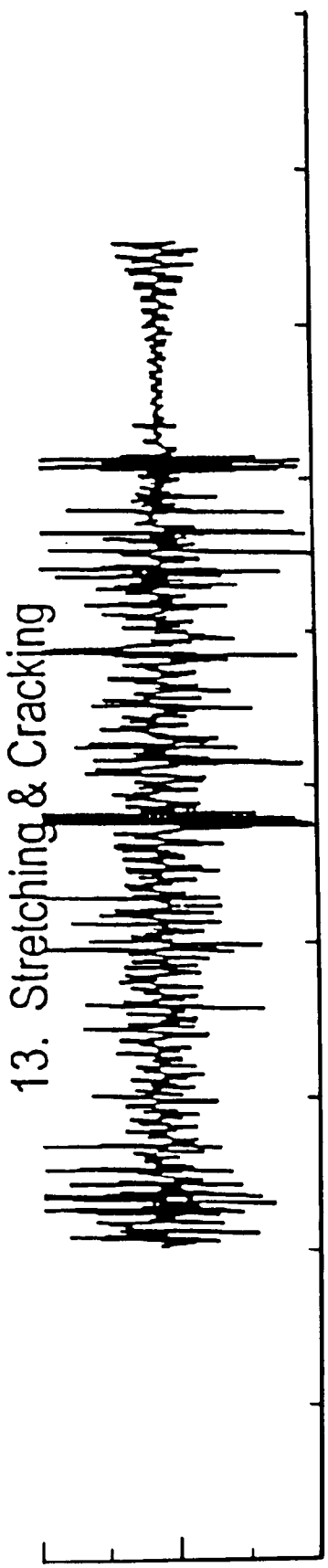
FIG. 25A illustrates a time segment taken from the full BA treatment time period.
Figure 25B:
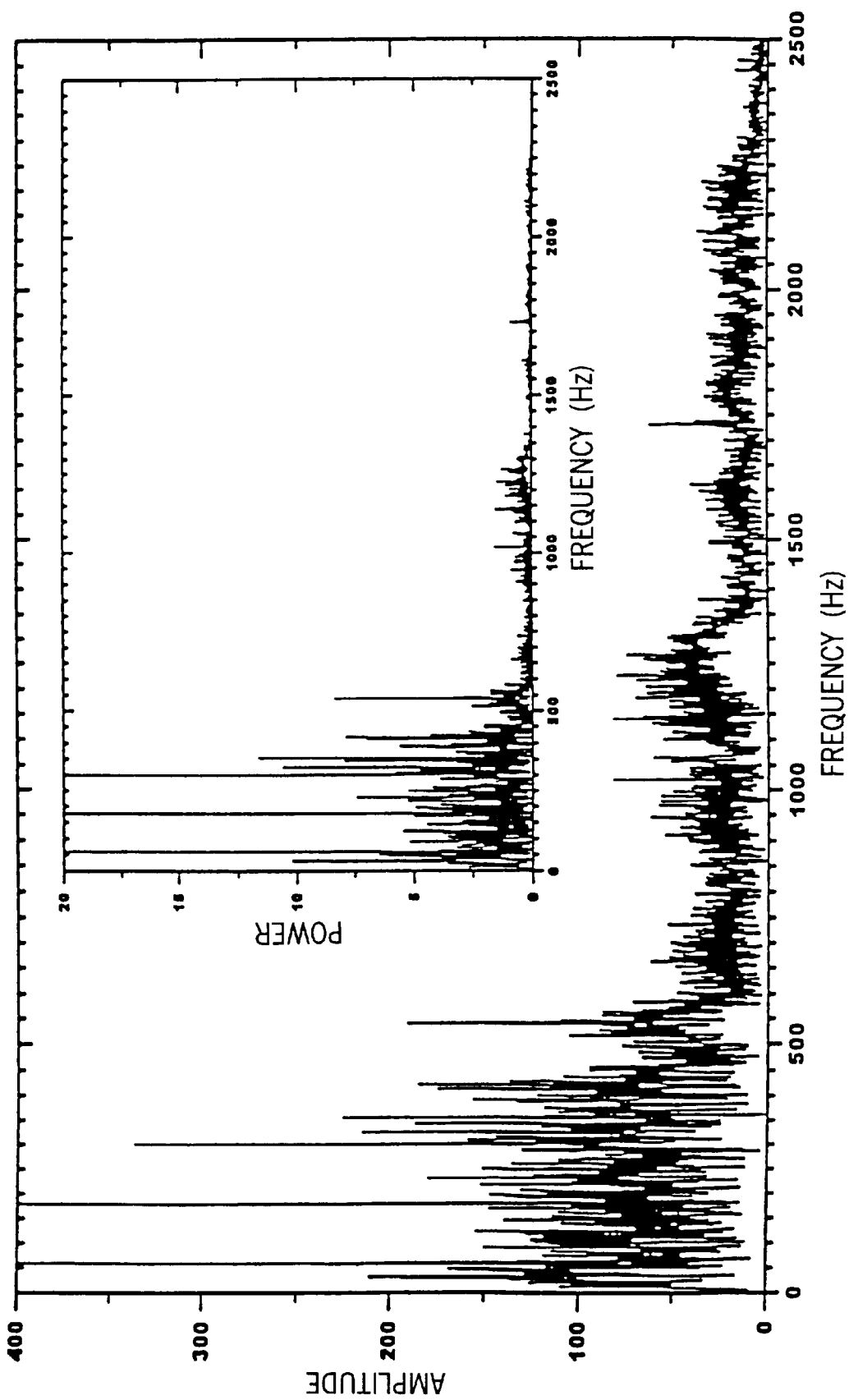
FIG. 25B illustrates a Fourier transform of the data of FIG. 25A and a power spectrum is also shown.
Figure 26A:
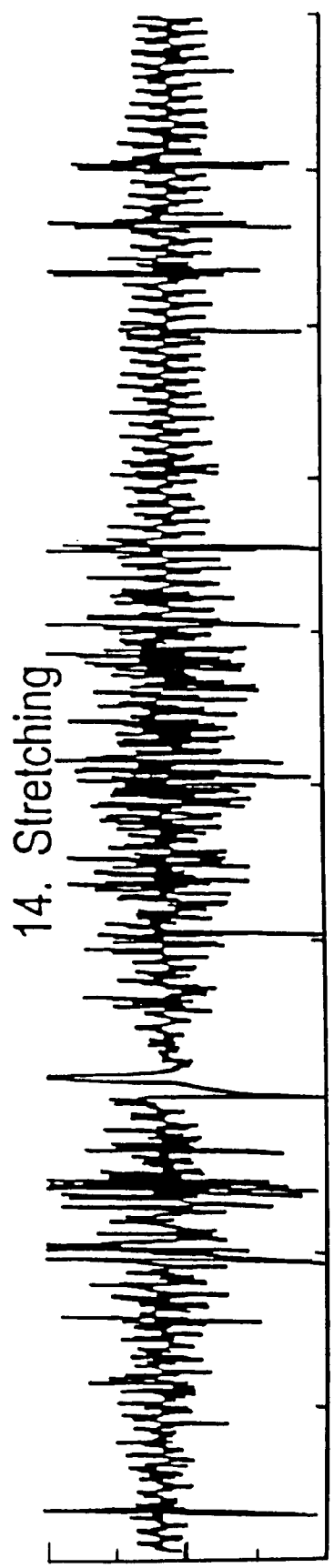
FIG. 26A illustrates a time segment taken from the full BA treatment time period.
Figure 26B:
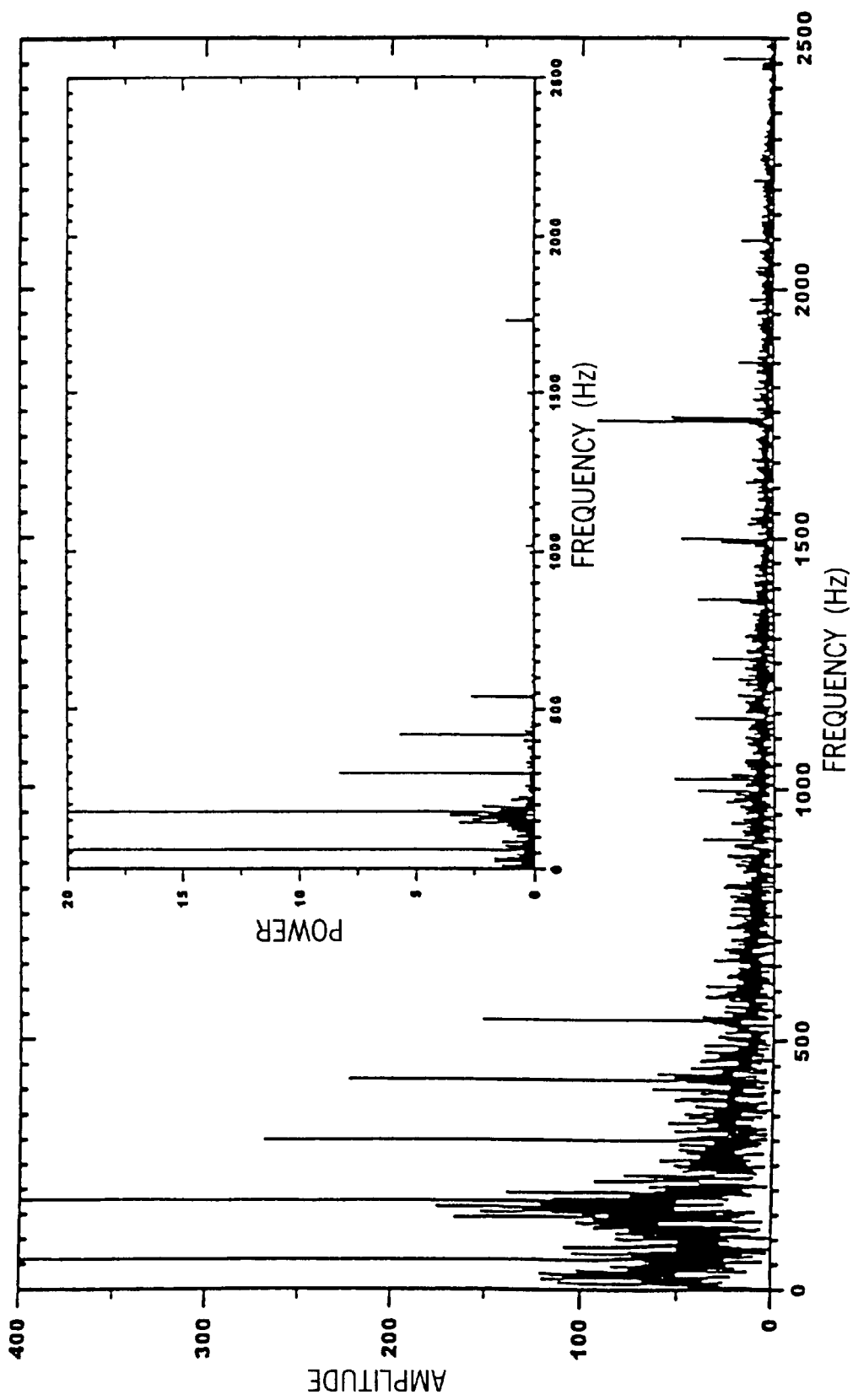
FIG. 26B illustrates a Fourier transform of the data of FIG. 26A and a power spectrum is also shown.
Figure 27B:
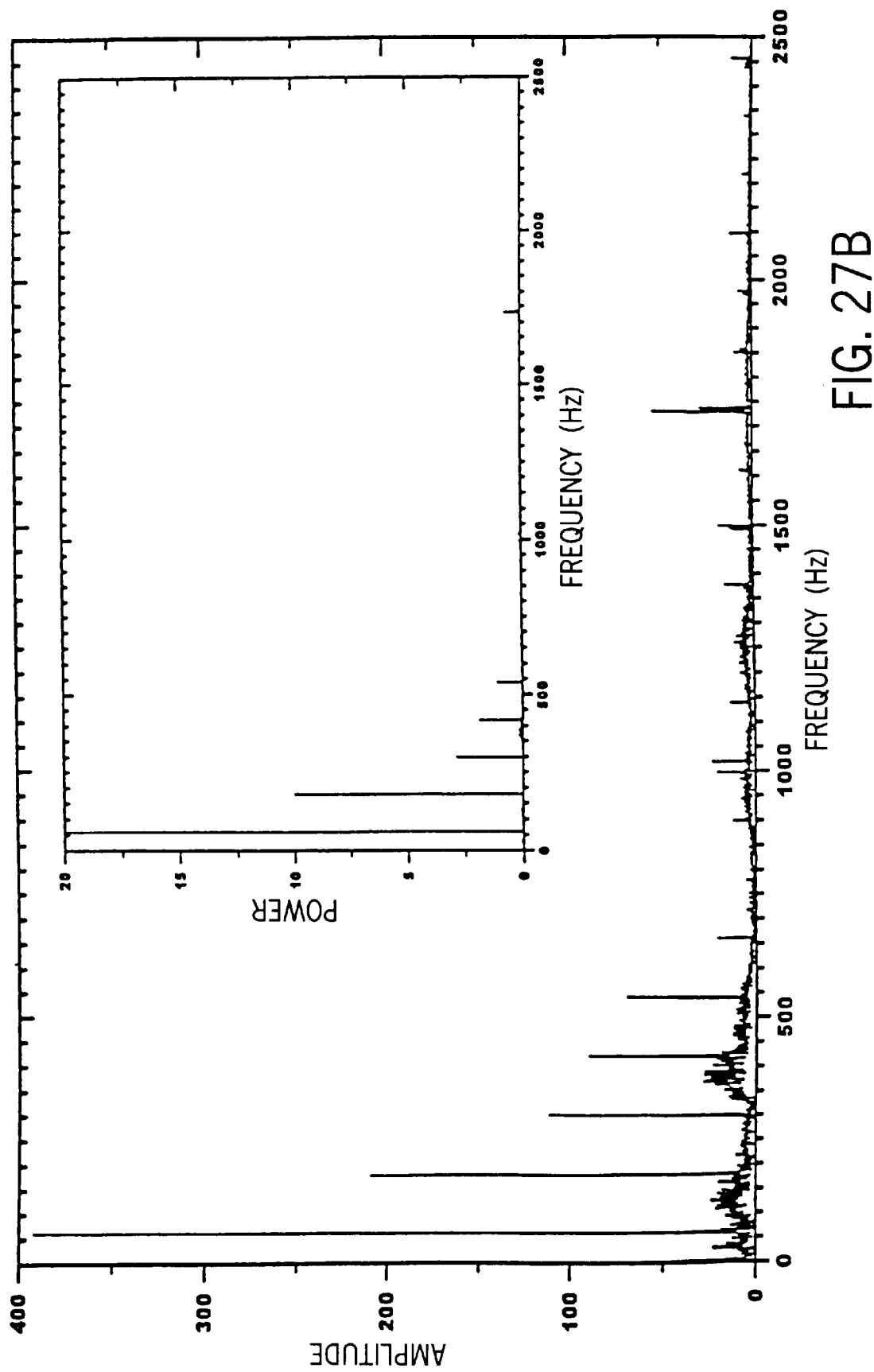
FIG. 27B illustrates a Fourier transform of the data of FIG. 27A and a power spectrum is also shown.

In another approach to analysis of the acoustic emission signals, various portions of the time record are selected as being associated with particular sound groups. For example, without limiting the scope of the invention, in FIG. 13A is shown a time record segment which is believed to be associated with tearing or rupture of vascular tissue. In FIG. 13B is the associated Fourier transform of the data of FIG. 13A showing frequency versus amplitude with an inset power versus frequency plot. FIGS. 14A and B through FIGS. 27A and B illustrate other portions of the time period spectrum which are labeled as being likely associated with other selected BA events. It should, however, be noted that these asserted correlations are not intended to be limitations on the invention. Based on the analysis performed to date, it is clear that straightforward, unambiguous ex vivo experiments can readily establish reasonably good correlations which will also be used for performing the pattern recognition analysis in the manner described hereinbefore for the frequency spectrum approach. Consequently, as shown in FIG. 8, the final step in the analysis is performing a probabilistic pattern recognition analysis to determine which category the input data best correlates with.

Figure 28:
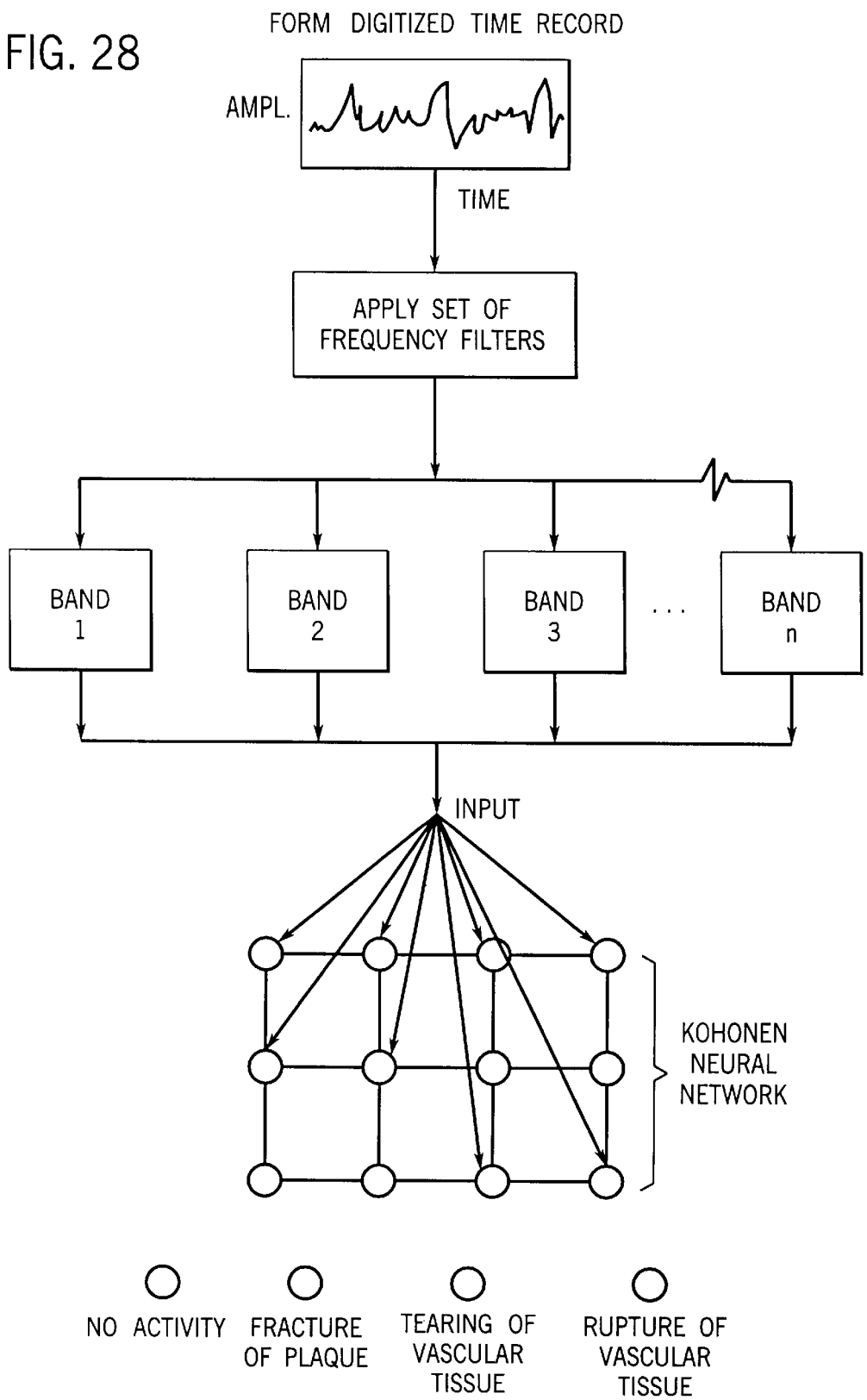
FIG. 28 shows a functional block flow diagram illustrating wavelet function analysis of acoustic information with probabilistic evaluation of the frequency filtered functions.
Figure 29:
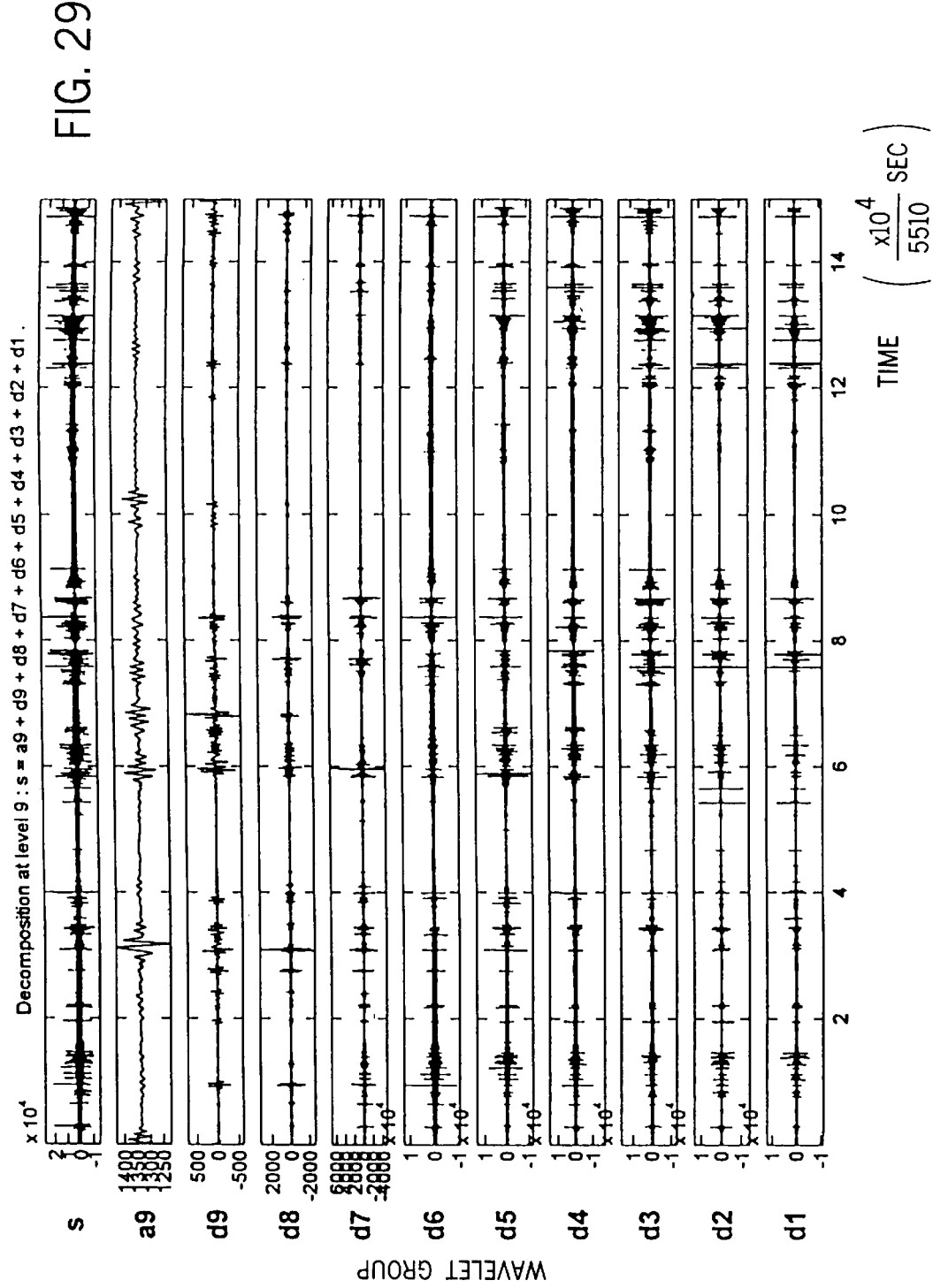
FIG. 29 shows a set of wavelet functions derived from a portion of a BA treatment time record.

In another approach to the analysis of the acoustic emission signals, various frequency bands can be selected for evaluation by a probabilistic network. For example, as shown in FIGS. 28 and 29, a time record over at least part of the BA treatment period (labeled "S" in FIG. 29) can be reduced to a number of individual frequency bands, such as bands a9 (lowest frequency band) and bands d9 to d1 (bands of decreasing frequency, with d1 the highest frequency). These frequency bands can be obtained by conventional methods, such as wavelet transformation or frequency band filtration. An example of data for such a series of these frequency band data were taken in Example II, and such raw data are shown in FIGS. 31–32. It should also be noted that wavelet analysis can be performed on any given time period of BA treatment data, either dynamically during treatment or afterward. In a manner similar to the analysis of spectrograms and sound segments, for each point in time of each selected frequency band, wavelet coefficients (amplitudes over time) are used to construct a vector for each point in time. The elements of each of these vectors are the wavelet coefficients for each level of the individual wavelet (the frequency band). The Kohonen network analysis proceeds using unsupervised learning to evaluate the frequency distribution of the input pattern with the trained network used to ascertain the category to which an unknown pattern belongs. Consequently, the probabilistic evaluation is done in substantially the same way as for the spectrogram evaluation, but instead processes wavelets. The result is correlation of the category content of the wavelets to establish whether the frequency band correlates best, for example, to nonactivity, fracture of plaque, prerupture of vascular tissue and rupture of vascular tissue.

Figure 30:
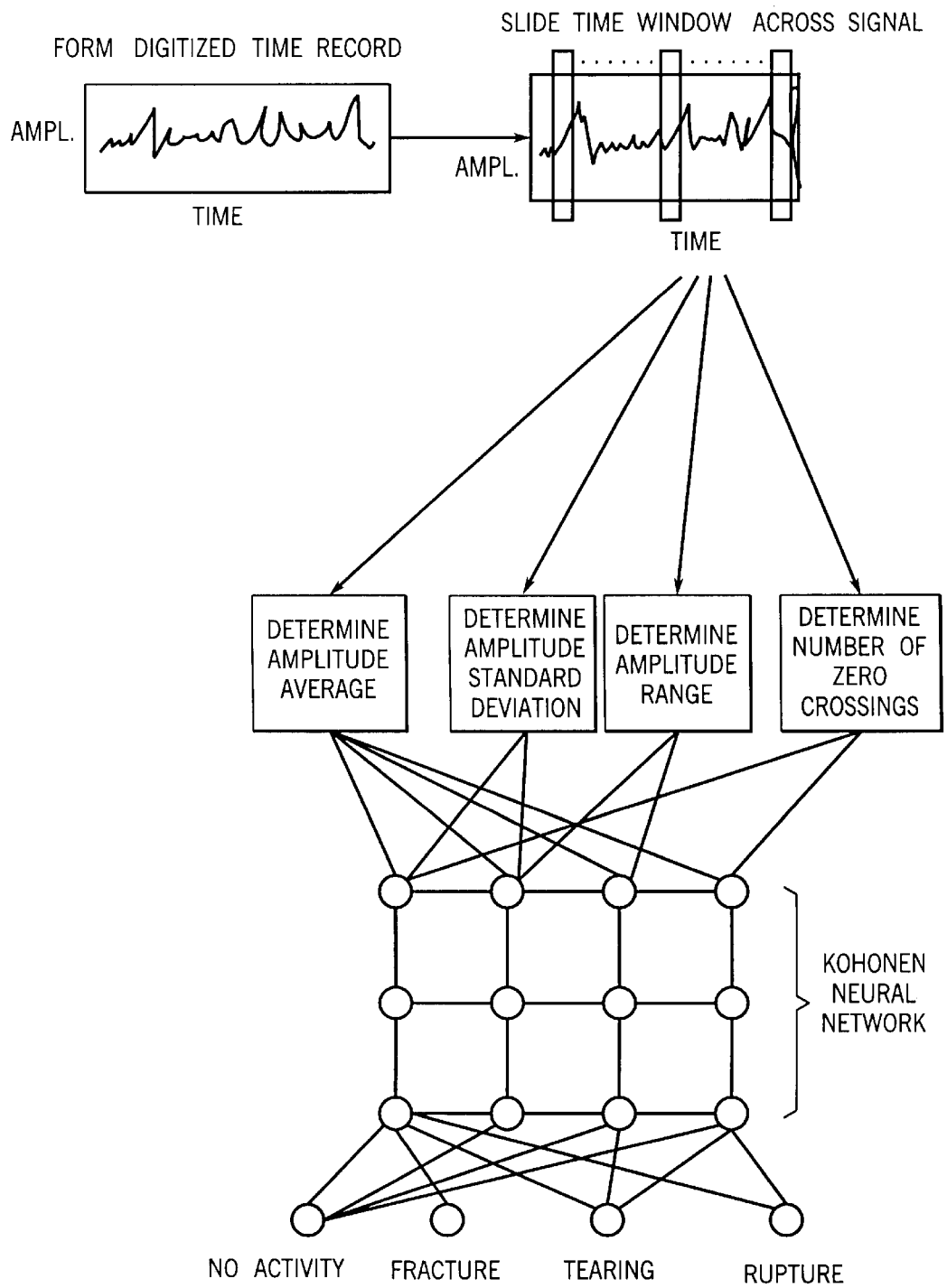
FIG. 30 shows a time record analysis of selected time function parameters by a probabilistic methodology.

In another approach to analysis of the acoustic emission signals, FIG. 30 shows a flow diagram of analysis of amplitude patterns in a time domain approach. The time domain amplitude spectra is characterized for a slice of the selected time record (dynamic ongoing real time or after treatment) by one of a variety of measures, such as zero crossings, the average amplitude, the standard deviation, the amplitude range, amplitude standard deviation and other conventional features. These variables can be determined by sliding a window segment across the time record (or collecting signal for a brief period). This can of course be done in real time as data is collected or after treatment for a user selected time period. The resulting values for each window segment are then input to each of the nodes of the Kohonen network. In turn, the network operates in the manner described hereinbefore to categorize the signal's variable data with the group to which positions of the data belong, such as plaque cracking, prerupture of vascular tissue and rupture of vascular tissue.

The following nonlimiting examples set forth various embodiments and experimental results obtained therefrom.

EXAMPLE I

A functional prototype of a BA system was constructed using 10 mm×31 mm×28 $\mu$m (thick) piece of PVDF film which was contact cemented to the external surface of a standard angioplasty balloon. Electrical connections were made to the sensor via adhesive-backed copper foil to which narrow gauge teflon-coated silver wires were soldered. The lead wires were routed distally over the surface of the balloon, into the distal pressure lumen aperture and back proximally through the body of the catheter to a female BBC connector. The prototype was electrically connected to the instrumentation system.

EXAMPLE II

The following lumen arterial specimens underwent BA procedures using the BA system of Example I: human peripheral arterial specimens (iliac and femoral arteries; 7–10 mm lumen diameter, 4–5 cm in length) exhibiting various amounts of disease were collected at autopsy, dissected free of extraneous tissue, cleaned in sterile normal saline, and flash frozen at −70° C. within 6–8 hours of death. Upon study, vessels were thawed to room temperature by immersion in normal saline, and sectioned into 1.0 cm rings.

The balloon diameter and arterial vessel lumen geometry were matched so that the inflated diameter of the balloon was between 1.0 and 1.3 times the estimated diameter of the non-diseased arterial lumen. 1.0 cm long arterial specimens (having appropriate lumen diameter) were individually positioned on the deflated balloon such that they covered the mid-section area containing the surface mounted piezoelectric sensor. A PVDF transducer was attached to a 10 mm angioplasty balloon with double-sided tape. The BA system (with mounted vascular specimen) was then rigidly mounted in an apparatus that eliminated spurious motion, and immersed into a temperature controlled (37°) normal saline bath. After allowing specimen temperature to equilibrate, BA treatment was conducted on the vascular segment according to standard methodology. During the entire procedure, acoustic emission information (i.e., audio recordings, analog strip chart tracings, and digital computer files sampled at about 25 KHz) was collected in real-time for subsequent analysis and display. The digital audio tape had a frequency response of 20–22 KHz. The digital audio tape recording was digitized with a PC sound card being sampled at 5510 Hz, and this digitized information was then available for analysis. In preliminary studies, the effects of several experimental variables were investigated in the following simple protocols:

1. The balloon was inflated from 0 Atm to 2 Atm until acoustic emission activity was observed to diminish. This was followed (without an intervening deflation) by an inflation to the maximum balloon pressure specified by the manufacturer. The balloon was then deflated, unloading the specimen (5 minutes duration), and re-inflated to 2 Atm while acoustic emission energy was recorded.

2. Step inflation from 0 Atm to 2 Atm was conducted with an unshielded (minimal electromagnetic interference protection) BA system with and without overlying vascular tissue.

3. An electromagnetic interference shielded BA system balloon was pre-inflated to 0.5 Atm (causing unfurling of the balloon), and then subjected to a step inflation from 0.5 Atm to 2 Atm with and without overlying vascular tissue.

FIGS. 31B and 31C depict typical in-vitro data collected according to the protocol shown in FIG. 31A and described above. Data is presented in a compressed format with FIG. 31B representing 57.93 seconds of information and FIG. 31C representing 125.96 seconds of data. Note that initial balloon inflation time was measured to be less than 1 second in duration. The beginning of these traces indicate a short period of baseline signal output (A). This period is followed shortly thereafter by initial balloon inflation (B), and prolonged vascular acoustic emission generation in response to a constant magnitude stress of 2 Atm (C). When acoustic emission activity diminished, balloon pressure was increased (D), resulting in a transient increase in acoustic emission activity (E) which rapidly decayed. The balloon was deflated for 5 minutes and then re-inflated to 2 Atm (F), producing low amplitude transient acoustic emission signals (G).

Figure 32A:
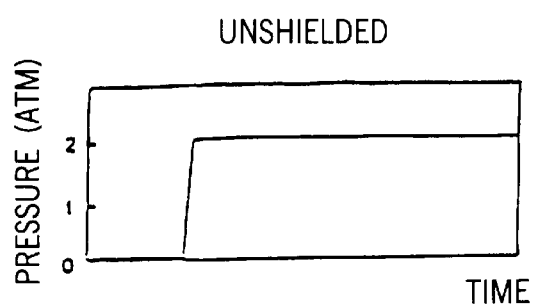
FIG. 32A shows a step inflation of a balloon.
Figure 32B:
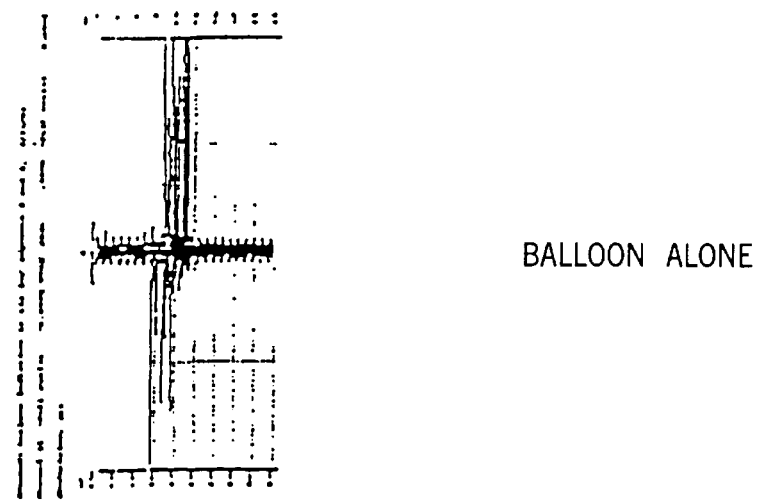
FIG. 32B shows acoustic emission for the balloon alone.
Figure 32C:
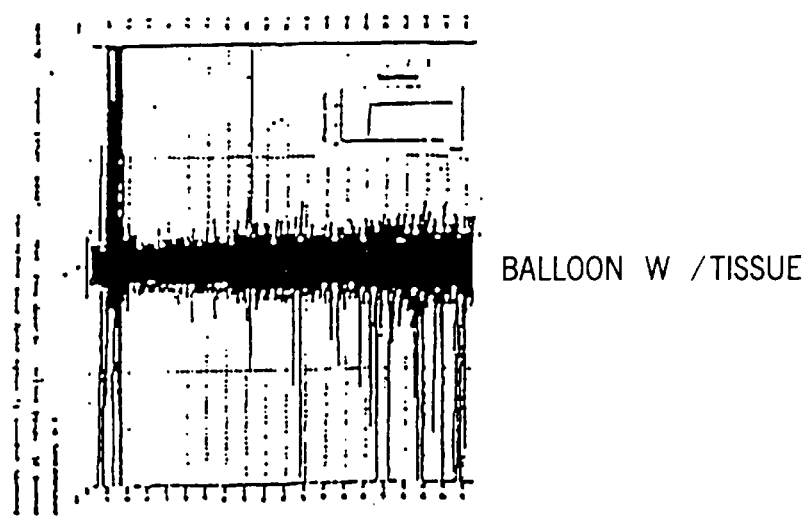
FIG. 32C shows acoustic information for both the balloon and tissue.

FIGS. 32B and 32C show the effects of a step inflation (0–2 Atm) of FIG. 32A performed with an unshielded prototype per protocol 2. Inflation of the balloon without an overlying tissue specimen reveals a fairly large baseline noise component at 0 Atm. Actual balloon inflation is accompanied by large acoustic emission artifacts created by the balloon unfurling, and a barely perceptible change in the noise content at 2.0 Atm. Balloon inflation duration is seen to be approximately 0.5 seconds. With the presence of overlying vascular tissue, step inflation invokes immediate, large amplitude acoustic emissions during the first 1.5 seconds (presumably contaminated by unfurling artifacts during the first 0.5 seconds), followed by lower amplitude, continuous-type acoustic emissions superimposed upon electromagnetic interference artifacts.

Figure 33A:
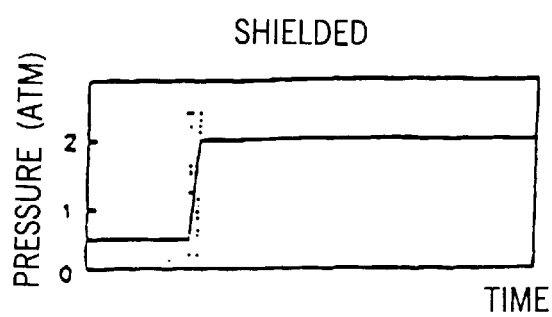
FIG. 33A shows a modified step inflation of a balloon.
Figure 33B:
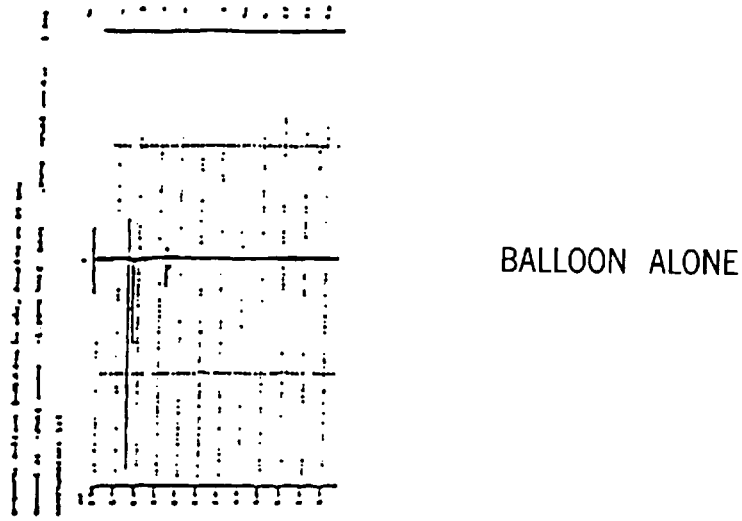
FIG. 33B shows acoustic emission for the balloon alone.
Figure 33C:
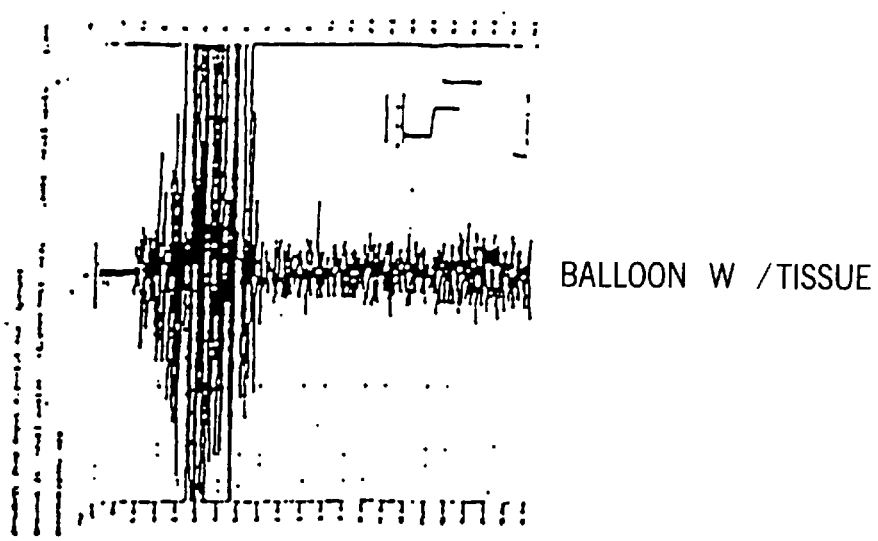
FIG. 33C shows acoustic information for the balloon and tissue together.

FIGS. 33B and 33C depicts the results of a modified step inflation performed with an electromagnetic interference shielded prototype per protocol 3 shown in FIG. 33A. Pre-inflation to 0.5 Atm caused the balloon to unfurl. Without the presence of overlying tissue, relatively low amplitude electromagnetic interference is detected on the baseline signal. Pressurization of the balloon from 0.5 to 2.0 Atm is accompanied by minimal acoustic emission activity, presumably due to the reduction of balloon unfurling artifacts. With overlying vascular tissue, acoustic emission gradually increase and then dissipate over a 5.5 second period upon pressurization from 0.5 to 2.0 Atm. Continuous-type acoustic emission activity of lower amplitude is evident during the elevated pressure plateau.

EXAMPLE III

Figure 34A:
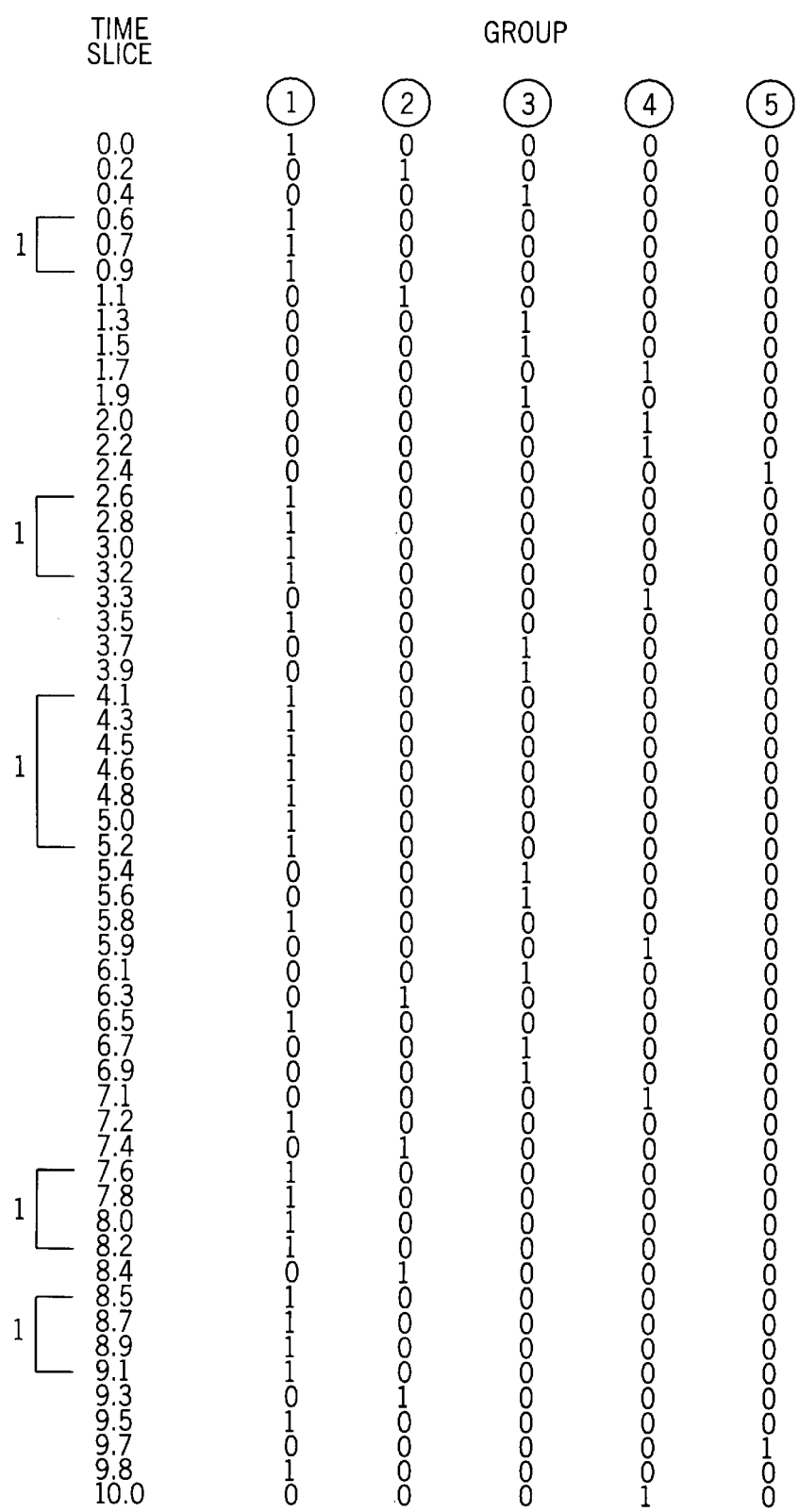

A Kohonen neural network analysis was applied to evaluation of Fourier transformed frequency amplitude data collected in the manner illustrated in FIG. 8 with some of that frequency information shown in FIGS. 9A–9N. The network was set up for five output categories and 1045 inputs, the 1045 frequencies of the spectrogram. The outputs of the network are the memberships of the five categories for each of the 1045 time sample. Category 1 corresponds to places in the sound file where there are no notable sounds, and category 5 corresponds to sounds associated with prerupture and rupture of vascular tissue. The results of that categorization are illustrated in FIGS. 34A to 34C.

While preferred embodiments of the invention have been shown and described, it will be clear to those of skill in the art that various changes and modifications can be made without departing from the invention in its broader aspects as set forth in the claims provided hereinafter.

What is claimed is:

1. A system for performing angioplasty treatment on a patient, comprising:
    a catheter for insertion into and through an artery of the patient;
    means consisting solely of a mechanical device coupled to the catheter for applying mechanical energy to atherosclerotic plaque lesions deposited on and within said vascular tissue of the artery and also for creating acoustic emission signals arising solely from mechanical displacement of the lesions and said vascular tissue, said device expandable by fluid passed through the catheter in order to apply mechanical pressure to plaque lesions coupled to said vascular tissue of the artery and to cause at least one of (a) deformation of the plaque lesions, (b) cracking of the plaque lesions, (c) stretching of said vascular tissue and (d) rupture of said vascular tissue;
    a transducer for sensing acoustic emission signals arising solely from expansion of the device to cause at least one of (a) deformation of the plaque lesions, (b) cracking of the plaque lesions, (c) stretching of said vascular tissue and (d) rupture of said vascular tissue; and
    means for evaluating the acoustic emission signals arising solely from the mechanical device coupled to the catheter applying mechanical pressure to the plaque lesions and the artery to determine which of the categories (a), (b), (c), and (d) said acoustic emission signals belong.

2. The system as defined in claim 1 wherein said transducer comprises a PVDF film included with said mechanical device.

3. The system as defined in claim 1 wherein said mechanical device is comprised at least in part of PVDF.

4. The system as defined in claim 1 wherein said transducer is disposed between an overlying metal layer and an underlying metal layer coupled to an exterior surface of said mechanical device.

5. The system as defined in claim 1 wherein said transducer is disposed between an overlying metal layer and an underlying metal layer coupled to an interior surface of said mechanical device.

6. The system as defined in claim 1 wherein said transducer comprises a matrix of piezoelectric material bands included with said balloon.

7. The system as defined in claim 1 wherein said transducer is disposed within said balloon and at least one of (a) on an interior surface of said catheter, (b) and an exterior surface of said catheter, and (c) integrally part of said catheter.

8. The system as defined in claim 1 further including at least one transducer coupled to said catheter for differential analysis of the acoustic emission signals in conjunction with said piezoelectric transducer included with said balloon.

9. The system as defined in claim 1 wherein said transducer comprises a non-invasive transducer adapted to be disposed on the chest wall of the patient.

10. The system as defined in claim 1 further including indicator means for informing a physician who is implementing the angioplasty treatment that an angioplasty event has occurred, thereby enabling the physician to selectively modify the balloon angioplasty treatment.

11. The system as defined in claim 10 wherein the means for informing comprises at least one of a speaker for outputting a sound spectrum characteristic of said angioplasty event and a display for showing the acoustic emission signals characteristic of said angioplasty event.

12. The system as defined in claim 1 further including means for automatically terminating the angioplasty treatment upon onset of vascular rupture.

13. The system as defined in claim 12 wherein said means for automatically terminating comprises an automatic pressure relief component for the fluid passed through said catheter.

14. The system as defined in claim 1 wherein said means for evaluating includes computer means for executing a Fourier transform computer program to convert a time varying form of said acoustic emission signals to a frequency amplitude spectrum for analysis of the balloon angioplasty treatment.

15. The system as defined in claim 14 further including a display for generating at least a two dimensional image of said frequency amplitude spectrum for analysis of the angioplasty treatment.

16. A system for performing angioplasty treatment on a patient, comprising:
    a catheter for insertion into and through an artery of the patient;
    a mechanical device coupled to said catheter, said mechanical device expandable by fluid passed through said catheter in order to apply pressure to atherosclerotic plaque lesions coupled to vascular tissue of the artery;
    said system including a transducer for sensing acoustic emissions signals generated by said mechanical device causing at least one of (a) deformation, of the plaque lesions, (b) cracking of the plaque lesions, (c) stretching of the vascular tissue and (d) rupture of the vascular tissue; and
    computer means for executing a computer program for analyzing said acoustic emissions signals arising solely from the mechanical device expansion causing at least one of (a) deformation of the plaque lesions, (b) cracking of the plaque lesions, (c) stretching of the vascular tissue and (d) rupture of the vascular tissue, said computer program operating on said acoustic emission signals to determine which of the categories (a), (b), (c) and (d) said acoustic emission signals belong.

17. The system as defined in claim 16 further including an A/D converter for generating a digitized data form of said acoustic emission signals and wherein said computer means comprises means responsive to said digitized data form for forming an overlapping series of Fourier transformed acoustic emission signals for input to a neural network computer program for analysis of the category in which said acoustic emission signals belong.

18. The system as defined in claim 16 further including means for automatically varying the pressure applied to the vascular tissue responsive to the analysis of said acoustic emission signals.

19. A method for performing angioplasty treatment on a patient, comprising the steps of:
    inserting a catheter into and through an artery of the patient, said catheter including a balloon positioned in a region of the artery having atherosclerotic plaque lesions coupled to interior walls of the artery;
    inflating said balloon to apply pressure to the plaque lesions causing at least one of (a) deformation of the plaque lesions, (b) cracking of the plaque lesions, (c) stretching of the artery and (d) rupture of the artery and further causing generation of acoustic emission signals arising solely from inflating said balloon to cause at least one of (a) deformation of the plaque lesions, (b) cracking of the plaque lesions, (c) stretching of the artery and (d) rupture of the artery;
    sensing said acoustic emissions signals using sensors;
    outputting said sensed acoustic emission signals to a computer; and
    executing computer programs to analyze said acoustic emission signals to carry out analysis of the angioplasty treatment.

20. The method as defined in claim 19 further including the step of performing Fourier transformations of said acoustic emission signals before performing analysis of said acoustic emissions signals.

21. The method as defined in claim 19 further including the step of performing frequency filtration of said acoustic emission signals to generate wavelets for analysis by a step of performing a neural network analysis.

22. A method for performing angioplasty treatment and deploying a stent in an artery of a patient, comprising the steps of: inserting a catheter into and through an artery of the patient, said catheter including a balloon and an attached deployable stent positioned in a region of the artery having atherosclerotic plaque lesions coupled to interior walls of the artery;
    inflating said balloon and deploying said stent to be in full apposition to the interior walls of the artery, said balloon applying pressure to the plaque lesions causing at least one of (a) deformation of the plaque lesions, (b) cracking of the plaque lesions, (c) stretching of the artery and (d) rupture of the artery and further causing generation of acoustic emission signals associated with (a) deformation of the plaque lesions, (b) cracking of the plaque lesions, (c) stretching of the vascular tissue of the artery and (d) rupture of vascular tissue of the artery and characterizing position of the stent relative to the walls of the artery;
    sensing said acoustic emission signals using a sensor;
    outputting said sensed acoustic emission signals to a computer; and
    executing a computer program using said computer to analyze said acoustic emission signals arising solely from the step of inflating the balloon which causes at least one of (a) deformation of the plaque lesions, (b) cracking of the plaque lesions, (c) stretching of the artery and (d) rupture of the artery to carry out analysis of the balloon angioplasty treatment and to help determine the position of said stent relative to the walls of the artery.

* * * * *

UNITED STATES PATENT AND TRADEMARK OFFICE
CERTIFICATE OF CORRECTION

PATENT NO. : 5,957,950
DATED : September 28, 1999
INVENTOR(S) : Mockros et al.

It is certified that error appears in the above-identified patent and that said Letters Patent is hereby corrected as shown below:

Column 6,
Line 15, delete "and a power of the spectrum" and insert -- power spectrum -- therefor;

Column 8,
Line 33, delete "restinosis" and insert -- restenosis -- therefor;

Column 13,
Line 15, delete "Example m" and isert -- Example III -- therefor;

Claim 7, column 17,
Line 2, delete "balloon" and insert -- mechanical device -- therefor;

Claim 8, column 17,
Line 9, delete "balloon"
\ and insert -- mechanical device -- therefor;
Line 9, delete "piezoelectric";

Claim 10, column 17,
Line 16, delete "balloon";

Claim 14, column 17,
Line 32, delete "balloon";

Signed and Sealed this

Eleventh Day of September, 2001

Attest:

NICHOLAS P. GODICI
*Attesting Officer*     *Acting Director of the United States Patent and Trademark Office*